United States Patent
Gill et al.

(10) Patent No.: US 12,157,728 B2
(45) Date of Patent: Dec. 3, 2024

(54) TARGETING OF ENDOPLASMIC RETICULUM DYSFUNCTION AND PROTEIN FOLDING STRESS TO TREAT NEUROLOGICAL CONDITIONS

(71) Applicant: ALS Therapy Development Institute, Cambridge, MA (US)

(72) Inventors: Alan Gill, Reading, MA (US); Steven Perrin, Newbury, MA (US)

(73) Assignee: ALS Therapy Development Institute, Cambridge, MA (US)

(*) Notice: Subject to any disclaimer, the term of this patent is extended or adjusted under 35 U.S.C. 154(b) by 0 days.

(21) Appl. No.: 18/213,557

(22) Filed: Jun. 23, 2023

(65) Prior Publication Data

US 2023/0382890 A1 Nov. 30, 2023

Related U.S. Application Data

(63) Continuation of application No. 16/982,923, filed as application No. PCT/US2019/018161 on Feb. 15, 2019, now Pat. No. 11,708,349.

(60) Provisional application No. 62/646,112, filed on Mar. 21, 2018.

(51) Int. Cl.
*C07D 401/14* (2006.01)
*A61K 9/00* (2006.01)
*A61K 31/7072* (2006.01)

(52) U.S. Cl.
CPC .......... *C07D 401/14* (2013.01); *A61K 9/0053* (2013.01); *A61K 31/7072* (2013.01)

(58) Field of Classification Search
CPC .......................... A61K 9/0053; C07D 401/14
See application file for complete search history.

(56) References Cited

U.S. PATENT DOCUMENTS

| | | |
|---|---|---|
| 8,859,587 B2 | 10/2014 | He et al. |
| 11,708,349 B2 | 7/2023 | Gill et al. |
| 2009/0203605 A1 | 8/2009 | Segatori et al. |
| 2010/0015653 A1 | 1/2010 | Kroemer et al. |
| 2013/0143917 A1 | 6/2013 | He et al. |
| 2015/0166472 A1 | 6/2015 | Kim et al. |
| 2016/0038571 A1 | 2/2016 | Peti et al. |
| 2021/0009558 A1 | 1/2021 | Gill et al. |

OTHER PUBLICATIONS

International Search Report and Written Opinion, PCT/US2019/018161, dated Apr. 24, 2019, 8 pages.
International Preliminary Report on Patentability, PCT/US2019/018161, dated Oct. 10, 2020, 7 pages.

*Primary Examiner* — Golam M Shameem
(74) *Attorney, Agent, or Firm* — Nelson Mullins Riley & Scarborough LLP; Jeanne M. DiGiorgio

(57) ABSTRACT

Methods and therapeutic compositions are disclosed for treating neurological disorders, such as Amyotrophic Lateral Sclerosis (ALS), Alzheimer's disease, Parkinson's disease and/or Huntington's disease, using Salubrinal analogs, or pharmaceutically acceptable salts, hydrates, or solvates thereof.

15 Claims, 25 Drawing Sheets

| Cpd ID | | Q1 | Q3 | RT (min) | Cpd ID | | Q1 | Q3 | RT (min) |
|---|---|---|---|---|---|---|---|---|---|
| 1- | Salubrinal | 479.10 | 187.10 | 2.21 | 26- | PPI-1924 | 609.10 | 187.10 | 3.24 |
| 2- | PPI-1901 | 551.00 | 187.10 | 2.38 | 27- | PPI-1925 | 609.10 | 187.00 | 3.33 |
| 3- | PPI-1902 | 593.10 | 57.10 | 2.72 | 28- | PPI-1926 | 675.20 | 187.10 | 4.00 and 4.10 |
| 4- | PPI-1903 | 535.00 | 187.00 | 2.38 | 29- | PPI-1927 | 656.10 | 187.10 | 2.49 |
| 5- | PPI-1904 | 589.10 | 187.10 | 2.68 | 30- | PPI-1928 | 661.10 | 187.00 | 3.87 and 3.89 |
| 6- | PPI-1905 | 563.10 | 187.00 | 2.68 | 31- | PPI-1929 | 635.10 | 563.10 | 3.57 and 3.77 |
| 7- | PPI-1906 | 565.10 | 187.00 | 2.53 | 32- | PPI-1930 | 649.10 | 187.10 | 3.84 and 3.94 |
| 8- | PPI-1907 | 619.10 | 187.00 | 2.87 | 33- | PPI-1931 | 606.00 | 187.10 | 2.25 |
| 9- | PPI-1908 | 687.10 | 105.00 | 2.77 | 34- | PPI-1932 | 708.10 | 187.10 | 2.68 and 2.72 |
| 10- | PPI-1909 | 583.10 | 105.10 | 2.47 | 35- | PPI-1933 | 651.10 | 187.00 | 3.37 |
| 11- | PPI-1910 | 579.10 | 187.10 | 2.64 | 36- | PPI-1934 | 637.10 | 187.00 | 3.05 |
| 12- | PPI-1911 | 613.10 | 105.10 | 2.69 | 37- | PPI-1935 | 623.10 | 187.00 | 2.99 |
| 13- | PPI-1912 | 581.10 | 231.00 | 2.9 | 38- | PPI-1936 | 665.10 | 187.00 | 3.39 |
| 14- | PPI-1913 | 633.10 | 187.10 | 2.94 and 3.02 | 39- | PPI-1937 | 722.20 | 187.10 | 2.82 and 2.86 |
| 15- | PPI-1914 | 673.10 | 187.00 | 2.70 | 40- | PPI-1938 | 706.10 | 198.10 | 2.59 |
| 16- | PPI-1915 | 563.10 | 187.00 | 2.62 | 41- | PPI-1939 | 756.2 | 202.1 | 2.76 and 2.79 |
| 17- | PPI-1916 | 551.00 | 217.20 | 2.21 | 42- | PPI-1940 | 679.2 | 187 | 3.40 |
| 18- | PPI-1917 | 603.10 | 187.00 | 2.82 | 43- | PPI-1941 | 665.1 | 166.9 | 3.26 |
| 19- | PPI-1912 | 581.10 | 231.00 | 2.90 | 44- | PPI-1942 | 493.1 | 201 | 2.76 |
| 20- | PPI-1918 | 621.10 | 187.00 | 3.00 | 45- | PPI-1943 | 625.1 | 59.1 | 2.86 |
| 21- | PPI-1919 | 608.10 | 187.10 | 2.34 | 46- | PPI-1944 | 579.1 | 101.1 | 2.88 |
| 22- | PPI-1920 | 622.10 | 187.10 | 2.46 | 47- | PPI-1945 | 693.2 | 143.1 | 3.49 |
| 23- | PPI-1921 | 607.10 | 187.10 | 3.48 and 3.58 | 48- | PPI-1946 | 665.1 | 187.1 | 3.22 |
| 24- | PPI-1922 | 567.00 | 275.00 | 2.89 | 49- | PPI-1947 | 707.2 | 187.1 | 3.62 |
| 25- | PPI-1923 | 595.10 | 187.10 | 3.14 | 50- | PPI-1948 | 750.3 | 196.1 | 2.91 |

FIG. 3

| Cpd ID | Incubation (1 h) in phosphate buffer pH 7.4 | | Incubation (1h) in mouse plasma | |
|---|---|---|---|---|
| | Mean parent loss (%) | % total of Salubrinal formation | Mean parent loss (%) | % total of Salubrinal formation |
| PPI-1901 | 47.1 | 2.0 | 98.9 | 32.5 |
| PPI-1902 | 1.2 | 0.9 | 92.3 | 22.6 |
| PPI-1903 | 12.8 | 21.0 | 86.4 | 72.7 |
| PPI-1904 | -3.8 | 7.4 | 81.2 | 48.8 |
| PPI-1905 | 100.0 | 60.5 | 100.0 | 55.3 |
| PPI-1906 | 30.8 | 1.5 | 100.0 | 28.6 |
| PPI-1907 | 22.1 | 0.7 | 98.5 | 40.9 |
| PPI-1908 | 50.5 | 6.3 | 100.0 | 17.7 |
| PPI-1909 | 57.1 | 14.9 | 39.4 | 20.5 |
| PPI-1910 | 28.3 | 1.3 | 88.8 | 43.3 |
| PPI-1911 | 17.9 | 0.4 | 39.9 | 33.2 |
| PPI-1912 | 78.4 | 6.8 | 100.0 | 55.6 |
| PPI-1913 | -19.3 | 1.6 | 55.8 | 30.6 |
| PPI-1914 | 2.0 | 8.8 | 100.0 | 71.0 |
| PPI-1915 | 6.4 | 9.0 | 88.9 | 71.3 |
| PPI-1916 | 86.3 | 67.9 | 100.0 | 66.6 |
| PPI-1917 | -5.3 | 1.5 | 70.5 | 43.8 |
| PPI-1918 | 43.5 | 23.3 | 100.0 | 66.5 |
| PPI-1919 | 53.4 | 19.9 | 100.0 | 79.6 |
| PPI-1920 | 70.5 | 37.6 | 100.0 | 81.2 |
| PPI-1921 | 6.5 | 2.2 | 35.3 | 10.2 |
| PPI-1922 | 80.3 | 2.1 | 100.0 | 13.5 |
| PPI-1923 | 60.6 | 2.1 | 100.0 | 4.7 |
| PPI-1924 | 47.0 | 0.7 | 91.5 | 0.9 |
| PPI-1925 | 51.3 | 3.4 | 100.0 | 5.3 |
| PPI-1926 | 12.3 | 1.0 | 50.2 | 17.0 |
| PPI-1927 | 60.0 | 23.8 | 99.8 | 70.4 |
| PPI-1928 | -0.2 | 1.0 | 37.2 | 3.4 |
| PPI-1929 | 1.8 | 4.6 | 31.4 | 4.8 |
| PPI-1930 | 55.7 | 0.7 | 38.2 | 4.2 |
| PPI-1931 | 90.3 | 68.1 | 100.0 | 92.9 |

FIG. 4A

| Cpd ID | Incubation (1 h) in phosphate buffer pH 7.4 | | Incubation (1 h) in mouse plasma | |
|---|---|---|---|---|
| | Mean parent loss (%) | % total Salubrinal formation | Mean parent loss (%) | % total Salubrinal formation |
| PPI-1932 | 40.2 | 1.5 | 99.9 | 77.4 |
| PPI-1933 | 20.2 | 1.9 | 100.0 | 61.0 |
| PPI-1934 | 38.3 | 3.8 | 100.0 | 25.1 |
| PPI-1935 | 40.9 | 5.6 | 99.7 | 33.1 |
| PPI-1936 | 12.7 | 1.7 | 99.8 | 48.8 |
| PPI-1937 | 28.0 | 23.6 | 100.0 | 73.2 |
| PPI-1938 | 37.0 | 1.6 | 99.8 | 82.3 |
| PPI-1939 | 20.6 | 2.8 | 100.0 | 121.4 |
| PPI-1940 | 20.4 | 0.9 | 100.0 | 11.1 |
| PPI-1941 | 31.3 | 1.6 | 100.0 | 9.1 |
| PPI-1942 | 5.7 | 0.0 | 28.2 | 0.0 |
| PPI-1943 | 58.7 | 9.2 | 100.0 | 68.2 |
| PPI-1944 | 1.8 | 1.1 | 100.0 | 1.2 |
| PPI-1945 | 9.9 | 6.1 | 99.3 | 28.4 |
| PPI-1946 | 17.6 | 2.2 | 96.8 | 7.3 |
| PPI-1947 | 4.0 | 0.3 | 99.5 | 15.9 |
| PPI-1948 | 26.6 | 4.0 | 63.2 | 11.1 |

FIG. 4B

| Ref Cpd | Buffer % loss | Mouse Plasma % loss |
|---|---|---|
| Salubrinal | 11.5 ± 2.5 | 23.8 ± 12.3 |
| Diltiazem | 3.2 ± 3.3 | 19.9 ± 25.7 |

FIG. 4C

| Cpd ID | Mean parent loss (%) in the presence of MsLM | | Comment |
|---|---|---|---|
| | w/o NADPH | with NADPH | |
| PPI-1901 | 43.5 | 3.7 | |
| PPI-1902 | - | - | Not soluble |
| PPI-1903 | 17.5 | 64.9 | |
| PPI-1904 | 8.2 | 13.6 | |
| PPI-1905 | 100.0 | 100.0 | Not stable in the matrix |
| PPI-1906 | 50.6 | 90.8 | |
| PPI-1907 | 15.4 | 78.5 | |
| PPI-1908 | 0.0 | 41.0 | |
| PPI-1909 | 64.7 | 92.2 | |
| PPI-1910 | 0.0 | 55.3 | |
| PPI-1911 | 12.3 | 42.7 | |
| PPI-1912 | 82.0 | 80.7 | Not stable in the matrix |
| PPI-1913 | 14.6 | -49.0 | |
| PPI-1914 | -43.0 | -275.6 | Solubility issues |
| PPI-1915 | -63.4 | 33.9 | |
| PPI-1916 | 100.0 | 100.0 | Not stable in the matrix |
| PPI-1917 | -9.3 | 13.2 | |
| PPI-1918 | 30.8 | 44.9 | |
| PPI-1919 | 44.3 | 59.6 | |
| PPI-1920 | 71.2 | 75.6 | |
| PPI-1921 | 19.3 | 20.7 | |
| PPI-1922 | 54.9 | 93.3 | |
| PPI-1923 | 51.2 | 85.8 | |
| PPI-1924 | 55.4 | 85.8 | |
| PPI-1925 | 18.7 | -4.5 | |
| PPI-1926 | 4.0 | -35.5 | |
| PPI-1927 | 83.6 | 90.3 | Not stable in the matrix |
| PPI-1928 | 8.0 | 16.9 | |
| PPI-1929 | 8.8 | 14.7 | |
| PPI-1930 | 8.7 | 20.1 | |
| PPI-1931 | 100.0 | 69.9 | Not stable in the matrix |

FIG. 5A

| Cpd ID | Mean parent loss (%) in the presence of MsLM | | Comment |
|---|---|---|---|
| | W/O NADPH | With NADPH | |
| PPL-1932 | 100.0 | 100.0 | Not stable in the matrix |
| PPL-1933 | 49.7 | 35.5 | |
| PPL-1934 | 49.2 | 57.4 | |
| PPL-1935 | 66.5 | 52.9 | |
| PPL-1936 | 40.2 | 16.7 | |
| PPL-1937 | 100.0 | 100.0 | Not stable in the matrix |
| PPL-1938 | 98.6 | 99.5 | Not stable in the matrix |
| PPL-1939 | 99.0 | 100.0 | Not stable in the matrix |
| PPL-1940 | 14.8 | 14.1 | |
| PPL-1941 | -29.5 | 24.3 | |
| PPL-1942 | 3.4 | 83.0 | |
| PPL-1943 | 56.3 | 64.7 | |
| PPL-1944 | 38.4 | 45.9 | |
| PPL-1945 | 12.6 | 26.4 | |
| PPL-1946 | 30.7 | 40.4 | |
| PPL-1947 | 25.7 | 21.6 | |
| PPL-1948 | 21.6 | 96.5 | |

FIG. 5B

| Ref Cpd | Buffer % loss | Mouse Plasma % loss |
|---|---|---|
| Salubrinal | 7.5 ± 7.3 | 99.8 ± 0.2 |
| Verapamil | -0.8 ± 23.3 | 87.6 ± 4.8 |
| Diphenhydramine | 1.0 ± 12.6 | 88.6 ± 3.7 | n = 10

FIG. 5C

| Cmpd | Dose (μM) | TUN (μM) | Viability Measure | N | Mean | Fold Cmpd=0 | Area Change | Total Area Change |
|---|---|---|---|---|---|---|---|---|
| 1934 | 0 | 0 | A450 | 3 | 2.601 | | | |
| 1934 | 1 | 0 | A450 | 3 | 2.929 | 1.126 | +0.126 | |
| 1934 | 10 | 0 | A450 | 3 | 1.773 | 0.681 | -0.319 | |
| 1934 | 30 | 0 | A450 | 3 | 0.805 | 0.310 | -0.690 | -0.883 |

| Cmpd | Dose (μM) | TUN (μM) | Viability Measure | N | Mean | Fold Cmpd=0 | Area Increase | Total Area Increase |
|---|---|---|---|---|---|---|---|---|
| 1934 | 0 | 0.03 | A450 | 3 | 0.528 | | | |
| 1934 | 0 | 0.1 | A450 | 3 | 0.491 | | | |
| 1934 | 0 | 1 | A450 | 3 | 0.468 | | | |
| 1934 | 1 | 0.03 | A450 | 3 | 0.558 | 1.057 | | |
| 1934 | 1 | 0.1 | A450 | 3 | 0.507 | 1.033 | | |
| 1934 | 1 | 1 | A450 | 3 | 0.477 | 1.020 | 0.111 | |
| 1934 | 10 | 0.03 | A450 | 3 | 0.788 | 1.492 | | |
| 1934 | 10 | 0.1 | A450 | 3 | 0.579 | 1.181 | | |
| 1934 | 10 | 1 | A450 | 3 | 0.559 | 1.195 | 0.868 | |
| 1934 | 30 | 0.03 | A450 | 3 | 0.830 | 1.571 | | |
| 1934 | 30 | 0.1 | A450 | 3 | 0.790 | 1.611 | | |
| 1934 | 30 | 1 | A450 | 3 | 0.747 | 1.598 | 1.780 | 2.759 |

FIG. 25

| Cmpd ID | Structure | Viability AUC | | Buffer | | Plasma | | Liver Microsomes | |
|---|---|---|---|---|---|---|---|---|---|
| | | Total Increase vs. TUN | Change, Cmpd Only | Parent Loss | Salubrinal Gain | Parent Loss | Salubrinal Gain | − | + |
| 1901 | | 8.300 | 0.083 | 47 | 2 | 99 | 33 | 44 | 4 |
| 1903 | | 3.535 | -0.173 | 13 | 21 | 86 | 73 | 18 | 65 |
| 1905 | | 8.307 | 0.097 | 100 | 61 | 100 | 55 | 100 | 100 |
| 1906 | | 4.530 | 0.249 | 31 | 2 | 100 | 29 | 61 | 91 |
| 1912 | | 6.335 | -0.347 | 78 | 7 | 100 | 56 | 82 | 81 |
| 1913 | | 2.946 | 0.581 | 0 | 2 | 56 | 31 | 15 | 0 |
| 1914 | | 6.032 | 0.037 | 2 | 9 | 100 | 71 | 0 | 0 |
| 1918 | | 6.149 | -0.175 | 44 | 23 | 100 | 67 | 31 | 45 |
| 1924 | | 6.187 | 0.439 | 47 | 1 | 92 | 1 | 55 | 86 |
| 1946 | | 4.464 | -0.012 | 18 | 2 | 97 | 7 | 31 | 40 |

TARGETING OF ENDOPLASMIC RETICULUM DYSFUNCTION AND PROTEIN FOLDING STRESS TO TREAT NEUROLOGICAL CONDITIONS

CROSS-REFERENCE TO RELATED APPLICATIONS

This application is a continuation of U.S. patent application Ser. No. 16/982,923, filed on Sep. 21, 2020, which is a 35 U.S.C. 371 national stage filing of International Application No. PCT/US2019/018161, filed on Feb. 15, 2019, and claims priority to U.S. Provisional Application No. 62/646,112, filed on Mar. 21, 2018. The contents of the aforementioned applications are hereby incorporated by reference.

BACKGROUND OF THE INVENTION

The technical field of this invention is the treatment of neurodegenerative or neuromuscular disorders such as Amyotrophic Lateral Sclerosis (ALS), Alzheimer's disease, Parkinson's disease and/or Huntington's disease.

ALS is a progressive neurological disorder characterized by muscle fiber atrophy resulting from the degeneration of motor neurons in the spinal column and brain. ALS affects approximately 30,000 US citizens, with only about 10% of cases being classified as the familial form of ALS. In a subset of familial patients with mutations in the metabolic enzyme superoxide dismutase 1 (SOD1), the pathological progression may be attributed to unknown factors associated with a mutant form of the SOD1 enzyme. However, in the majority of ALS cases the SOD1 gene contains no mutations and the mechanism of disease pathology is even less clear. Therefore, the remaining 90% of ALS cases are classified as sporadic cases, with no well-characterized genetic component or causal agent.

Alzheimer's disease is another progressive neurodegenerative disease. Early symptoms include difficulty in remembering recent events and in many instances Alzheimer's disease progresses to dementia. The disease process is associated with plaque deposits of the β-amyloid peptide and neurofibrillary tangles of the microtubule binding protein tau in the brain.

Amyloid protein accumulations have also been implicated in Parkinson's and Huntington's diseases. In Parkinson's disease, misfolding of the α-synuclein protein has been associated with disease manifestation. In Huntington's disease, alterations in Huntingtin protein appear to play a role in disruption of nerve cell functions.

Recently, it has been suggested that endoplasmic reticulum (ER) stress and the unfolded protein response (UPR) are involved in these and other neurological diseases. The endoplasmic reticulum is a membrane system within the cytoplasm of eukaryotic cells and serves various functions, including the synthesis, folding, modification, and transport of proteins. A number of stress conditions can interfere with ER function and cause abnormal protein folding, resulting in a cellular condition termed "ER stress." The unfolded protein response (UPR) is related to ER stress and is generally understood to be triggered by an accumulation of unfolded or misfolded proteins within the cell.

Studies have identified several signaling branches of UPR, including, for example, increased phosphorylation of eukaryotic initiation factor 2-alpha (eIF2-alpha). Eukaryotic translation initiation factor 2-alpha kinase 3, also known as protein kinase R (PKR)-like endoplasmic reticulum kinase (PERK), is an enzyme that phosphorylates eIF2-alpha. Over phosphorylation of eIF2-alpha has also been demonstrated in post-mortem spinal cord of ALS patients. Additionally, increased expression of X-box binding protein 1 (XBP1), activated transcription factor 4 (ATF4), and transcription factor C/EBP homologous protein (CHOP) expression is often observed in human ALS spinal cord analyses and these factors may also be implicated in ER stress and UPR.

Activation of the UPR can also be modeled in transgenic mice that over express mutant human SOD1 genes. Genetic modulation of the UPR in transgenic mice over-expressing mutant human SOD1 significantly influences motor neuron disease symptom onset and lifespan. Mice over-expressing G85R mutant human SOD1 in the context of PERK haploinsufficiency have earlier disease onset and reduced lifespans compared to G85R-SOD1 mice on a PERK+/+ background. On the other hand, the same G85R-SOD1 mice crossed to mice with a mutated GADD34 gene on one allele have delayed onset and significantly prolonged survival.

Salubrinal (N-(2,2,2-trichloro-1-(3-(quinolin-8-yl)thioureido)ethyl)cinnamamide) is a small molecule identified as protective of ER stress in a cell based assay from a library of 19,000 compounds See, Boyce et al., A selective inhibitor of eIF2alpha dephosphorylation protects cells from ER stress, *Science,* 307:935-939, (2005). Specifically, Salubrinal has been shown to inhibit ER stress-mediated apoptosis that is induced by tunicamycin, a protein glycosylation inhibitor.

At least one study suggests that salubrinal, as an inhibitor of ER stress, slowed motor neuron degeneration and extended survival of SOD1 mice. See, Walker et al. *PloS One* 8 (11) e81170 (2013).

Salubrinal has also been reported to attenuate β-amyloid-induced neuronal death and microglial activation associated with Alzheimer's disease. See, Huang et al., *Neurobiol. Aging, May* 33(5) 1007 (2012). Salubrinal has further been reported to protected PC12 cells from cell death induced by α-synuclein, a component of Lewy bodies seen in Parkinson's disease. See, Smith et al., *Human Molecular Genetics* 14(24) 3801-11 (2005).

The chemical structure of Salubrinal is shown below in Formula (I):

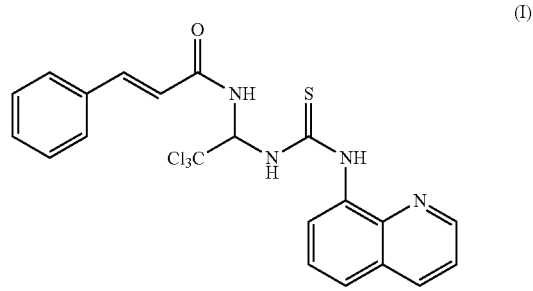

Despite its use as a research tool, use of Salubrinal as a therapeutic agent is limited because of its low solubility in aqueous solutions, rapid clearance and relatively high toxicity in animals (EC50~15 μM). New chemical compounds with better properties such as, for example and without limitation, higher solubility in biological fluids, slower clearance rates, and lower toxicity are required.

SUMMARY OF THE INVENTION

Methods and compositions are disclosed that relate to the treatment of neurological (neurodegenerative or neuromuscular) disorders characterized by endoplasmic reticulum stress or unfolded protein response.

In one aspect, methods and therapeutic compositions for treating neurological disorders by administering a compound are disclosed. Preferred compounds belong to a class of Salubrinal analogs (excluding Salubrinal itself) and can be defined by the general Formula (II):

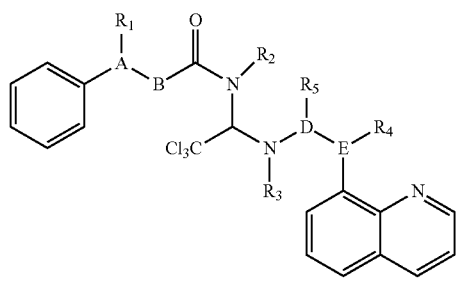

(II)

In certain embodiments, $R^1$ can be H, $C_{3-6}$ cycloheteroalkyl, or $N(CH_3)_2$, $R^2$ can be H, $C_{3-6}$ cycloheteroalkyl, or when combined with $R^4$ is together —CH($C_{1-10}$-alkyl)— or —CH($_{1-5}$-heteroalkyl)—, $R^3$ can be H, $CH_2(C_{3-6}$ cycloheteroalkyl), $C_{3-6}$ cycloheteroalkyl, amino acid, amino acid derivative, $C_{1-20}$ alkyl, or $C_{1-20}$ heteroalkyl, $R^4$ can be null, H, $CH_2(C_{3-6}$ cycloheteroalkyl), $C_{3-6}$ cycloheteroalkyl, amino acid, amino acid derivative, $C_{1-20}$ alkyl, or $C_{1-20}$ heteroalkyl, $R^5$ can be =S or $SR^6$, $R^6$ can be $CH_2(C_{3-6}$ cycloheteroalkyl), $C_{3-6}$ cycloheteroalkyl, acid, amino acid derivative, $C_{1-20}$ alkyl, or $C_{1-20}$ heteroalkyl, A-B can be CH—$CH_2$ or C=CH, and D-E can be C—N, CH—N, or C=N.

In one aspect of the invention the salubrinal analogs are designed to decompose in plasma over time to release salubrinal. Thus, the compositions are novel prodrug versions of salubrinal.

In other embodiments, the compound can be a pharmaceutically acceptable salt, hydrate, or solvate thereof. For example, the compound can be a chloride salt, hydrochloride salt, or a phosphate salt.

In one exemplary embodiment, the compound can have the structure of Formula (III), as shown below,

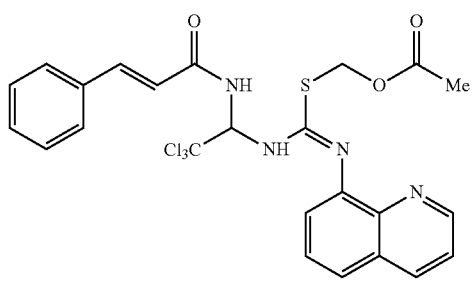

(III)

or a pharmaceutically acceptable salt, hydrate, or solvate thereof.

In another exemplary embodiment, the compound can have the structure of Formula (IV), as shown below,

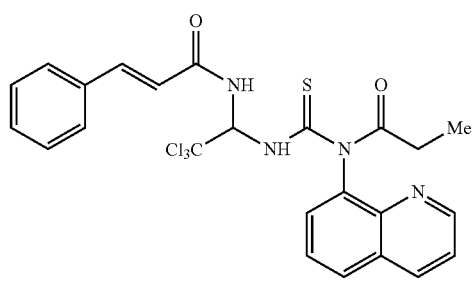

(IV)

or a pharmaceutically acceptable salt, hydrate, or solvate thereof.

In another exemplary embodiment, the compound can have the structure of Formula (V), as shown below,

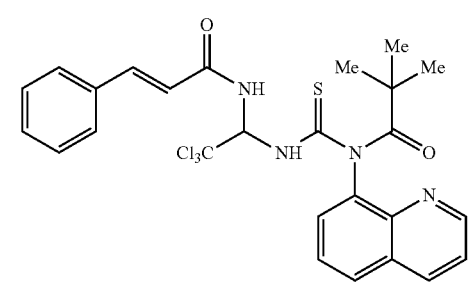

(V)

or a pharmaceutically acceptable salt, hydrate, or solvate thereof.

In another exemplary embodiment, the compound can have the structure of Formula (VI), as shown below,

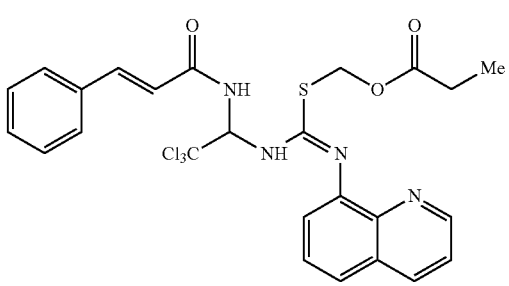

(VI)

or a pharmaceutically acceptable salt, hydrate, or solvate thereof.

In another exemplary embodiment, the compound can have the structure of Formula (VII), as shown below,

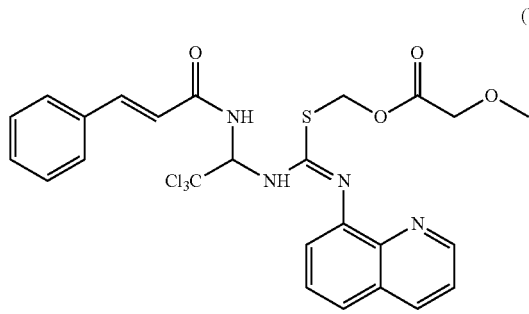

(VII)

or a pharmaceutically acceptable salt, hydrate, or solvate thereof.

In another exemplary embodiment, the compound can have the structure of Formula (VIII), as shown below,

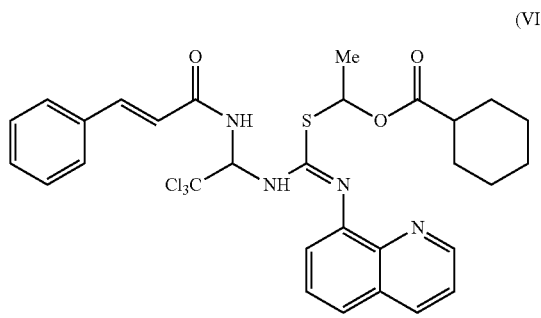

(VIII)

or a pharmaceutically acceptable salt, hydrate, or solvate thereof.

In another exemplary embodiment, the compound can have the structure of Formula (IX), as shown below,

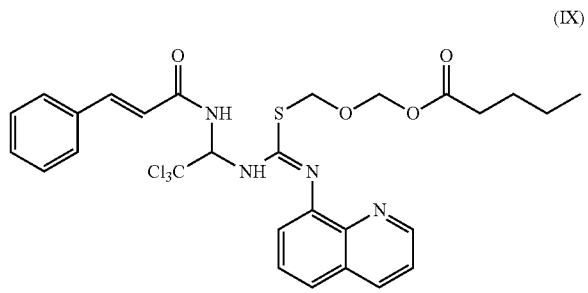

(IX)

or a pharmaceutically acceptable salt, hydrate, or solvate thereof.

In another exemplary embodiment, the compound can have the structure of Formula (X), as shown below,

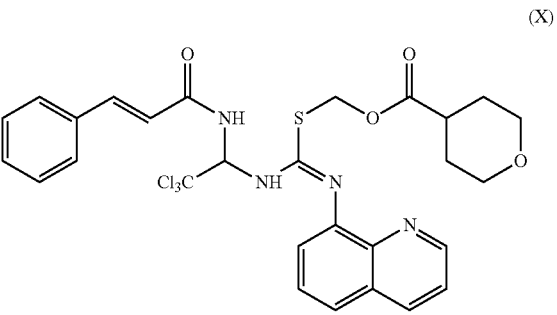

(X)

or a pharmaceutically acceptable salt, hydrate, or solvate thereof.

In another exemplary embodiment, the compound can have the structure of Formula (XI), as shown below,

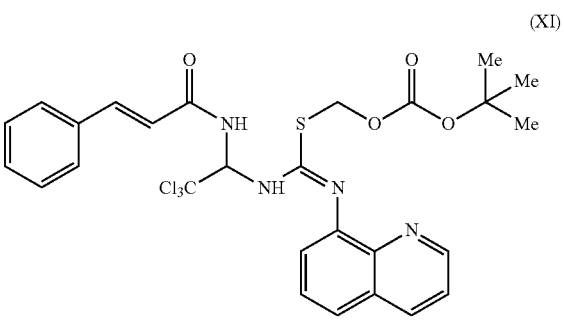

(XI)

or a pharmaceutically acceptable salt, hydrate, or solvate thereof.

In another exemplary embodiment, the compound can have the structure of Formula (XII), as shown below,

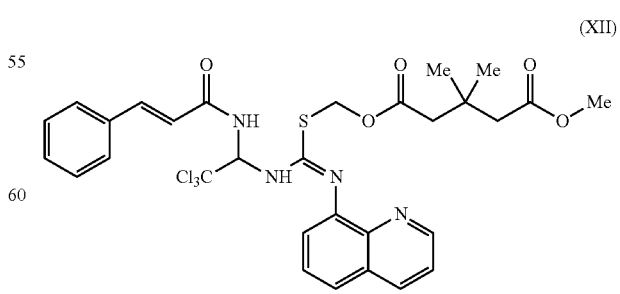

(XII)

or a pharmaceutically acceptable salt, hydrate, or solvate thereof.

In another exemplary embodiment, the compound can have the structure of Formula (XIII), as shown below, (XIII)

or a pharmaceutically acceptable salt, hydrate, or solvate thereof.

Methods and therapeutic compositions are also disclosed for modulating or ameliorating endoplasmic reticulum stress in neurodegenerative or neuromuscular disorders, and particularly Amyotrophic Lateral Sclerosis (ALS), Alzheimer's disease, Parkinson's disease and/or Huntington's disease. In one aspect, administration of the compound can inhibit endoplasmic reticulum stress-mediated apoptosis.

In one embodiment, this can be achieved through preventing dephosphorylation of the eukaryotic translation initiation factor 2 alpha (eIF2-alpha) by administering an inhibitor of eIF2-alpha, such as the salubrinal analogs described herein above as formula (II).

In another embodiments, the compound can be formulated with a pharmaceutically acceptable diluent, adjuvant, or carrier. The compound can be formulated for intraperitoneal administration, intravenous administration, anal administration, or any combination thereof. The compound can be formulated for oral administration, a single daily dose, and/or a dosage between 0.01 to 1 mg/kg/day or between 0.1 to 0.5 mg/kg/day. The compositions can be administered as a single dose or in multiple doses and can further include a pharmaceutically acceptable carrier. Examples of carrier include, but are not limited to, lipid, lipid derivative, liposome, protein, albumin, synthetic and/or natural polymer, synthetic and/or natural oligomer, cyclodextrin, cyclodextrin derivative, cellulose, and cellulose derivatives. The carrier can be selected from the group consisting of sulfobutylether beta cyclodextrin, methylcellulose, or a combination thereof. The formulation can have from about 0.1% to about 10% of carrier, from about 0.1% to about 5% of carrier, from about 0.1% to about 1.0% of carrier, or from about 0.5% to about 1.0% of carrier. In other embodiments, methods to protect cells or animals from target cell damage induced by the exposure to xenotoxicants known to induce endoplasmic reticulum stress and the subsequent unfolded protein are disclosed. The xenotoxicants include but are not limited to chemicals and pollutants (e.g., cadmium, arsenic, paraquat, rotenone, epoxides, dioxins, cigarette smoke, etc.) and drugs (e.g., cisplatin, cyclosporine, etcetera).

BRIEF DESCRIPTION OF THE DRAWINGS

A detailed description of various embodiments is provided herein below with reference, by way of example, to the following drawings. The skilled person in the art will understand that the drawings, described below, are for illustration purposes only. The drawings are not intended to limit the scope of the applicant's teachings in any way.

FIG. 3 is a table showing the MS/MS analysis of compound IDs 1901-1948;

FIG. 4A is a table showing the stability of compound IDs 1901-1931 in phosphate buffer and mouse plasma;

FIG. 4B is a table showing the stability of compound IDs 1932-1948 in phosphate buffer and mouse plasma;

FIG. 4C is a table showing the stability of two reference compounds (salubrinal and diltiazem) in phosphate buffer and mouse plasma;

FIG. 5A is a table showing the stability of compound IDs 1901-1931 in mouse liver microsomes;

FIG. 5B is a table showing the stability of compound IDs 1932-1948 in mouse liver microsomes;

FIG. 5C is a table showing the stability of three reference compounds (salubrinal, verapamil, and diphenhydramine) in mouse liver microsomes;

FIG. 25 is a drawing showing a summary of the properties of compound IDs 1901, 1903, 1905, 1906, 1912, 1913, 1914, 1918, 1924, and 1946.

DETAILED DESCRIPTION

Figure 1:
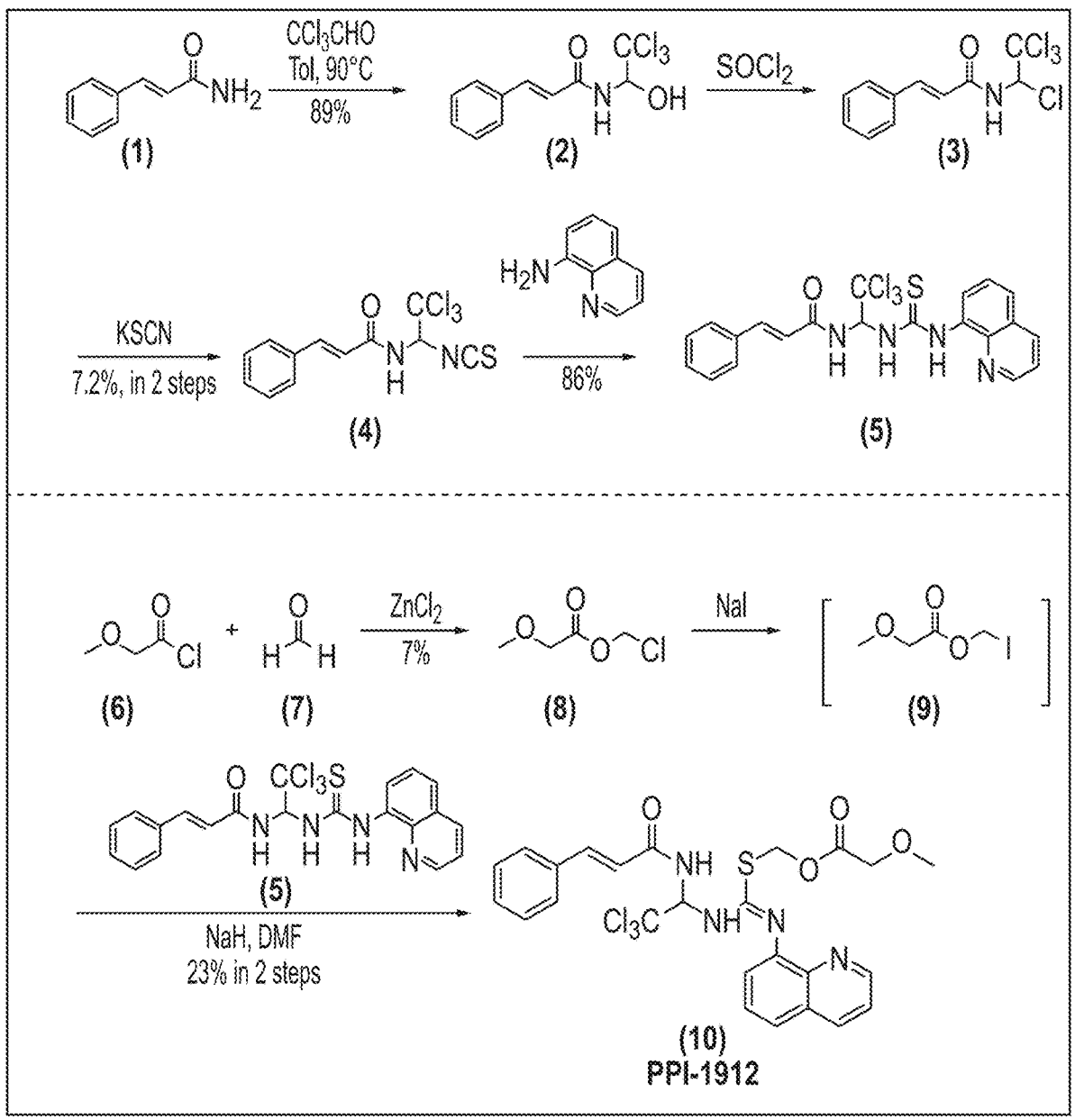
FIG. 1 is a diagram showing the synthesis of compound ID 1912.

The following abbreviations are used throughout the specifications and known to those skilled in the art: Amyotrophic Lateral Sclerosis (ALS); super oxide dismutase-1 (SOD1); endoplasmic reticulum (ER), unfolded protein response (UPR), eukaryotic initiation factor 2-alpha (eIF2-alpha), eukaryotic translation initiation factor 2-alpha kinase 3, also known as protein kinase R (PKR)-like endoplasmic reticulum kinase (PERK), X-box binding protein 1 (XBP1), activated transcription factor 4 (ATF4), and transcription factor C/EBP homologous protein (CHOP).

In the description that follows, and in documents incorporated by reference, a number of terms are used extensively. The following definitions are provided to facilitate understanding of the methods and compositions disclosed herein.

As used herein, the term "subject" is a human or other animal, having a neurological disorder. In some embodiments, the subjects are mammals. Examples of subjects can include, but are not limited to, humans, horses, monkeys, dogs, cats, mice, rates, cows, pigs, goats and sheep. In some embodiments, "subjects" are generally human patients having ALS.

As used herein, the term "alkyl" includes straight chain alkyl group, branched alkyl group, cyclic alkyl group, or any combinations thereof. The alkyl group may be fully saturated, monounsaturated or polyunsaturated, the alkyl group may be unsubstituted, monosubstituted or polysubstituted, and the alkyl group may include divalent or multivalent radicals having the number of carbon atoms designated (i.e., $C_{3-6}$ means three to six carbons). In some embodiments, the alkyl group is a $C_{1-20}$ alkyl group, more preferably a $C_{1-15}$ alkyl group, more preferably still a $C_{1-12}$ alkyl group, more preferably still, a $C_{1-6}$ alkyl group, or more preferably a $C_{1-3}$ alkyl group. In other embodiments, the alkyl group is a cyclic alkyl group and has at least three elements. Examples of saturated alkyl groups include, but are not limited to, groups such as methyl, ethyl, propyl, isopropyl, n-butyl, isobutyl, s-butyl, tert-butyl, homologs and isomers of, for example, n-pentyl and n-hexyl, and the like. An unsaturated alkyl group is one having one or more double bonds (also referred to herein as "alkenyl" group) or triple bonds (also referred to herein as "alkynyl" group). Examples of unsaturated alkyl groups include, but are not limited to, vinyl, 2-propenyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl" and "heterocycle."

As used herein, the term "alkenyl," by itself of in combination with another term, means, unless otherwise stated, a group containing one or more carbon-carbon double bonds. Preferably the alkenyl group is a $C_{2-20}$ alkenyl group, more preferably a $C_{2-15}$ alkenyl group, more preferably a $C_{2-12}$ alkenyl group, more preferably a $C_{2-6}$ alkenyl group, or more preferably a $C_{2-3}$ alkenyl group. The alkenyl group can be optionally substituted.

As used herein, the term "alkynyl," by itself of in combination with another term, means, unless otherwise stated, a group containing one or more carbon-carbon triple bonds. Preferably the alkynyl group is a $C_{2-20}$ alkynyl group, more preferably a $C_{2-15}$ alkynyl group, more preferably a $C_{2-12}$ alkynyl group, more preferably a $C_{2-6}$ alkynyl group, or more preferably a $C_{2-3}$ alkynyl group. The alkynyl group can be optionally substituted.

The term "heteroalkyl," by itself or in combination with another term, means, unless otherwise stated, an alkyl group consisting of the stated number of carbon atoms and at least one heteroatom selected from the group consisting of oxygen (O), nitrogen (N), silicon (Si), sulfur (S), and phosphorus (P), and wherein the O, N, S, Si, and P atoms may optionally be oxidized and the nitrogen heteroatom may optionally be a primary, secondary, tertiary, quaternary amine. The heteroatom(s) O, N, S, Si, and P may be placed at any interior position of the heteroalkyl or at the position at which the alkyl group is attached to the remainder of the molecule. The heteroalkyl group can be optionally substituted.

The term "aryl," by itself or in combination with another term, means, unless otherwise stated, a monovalent aromatic hydrocarbon radical of 6-20 carbon atoms derived by the removal of one hydrogen atom from a single carbon atom of a parent aromatic ring system. Aryl includes bicyclic radicals comprising an aromatic ring fused to a saturated, partially unsaturated ring, or aromatic carbocyclic or heterocyclic ring. Exemplary aryl groups include, but are not limited to, radicals derived from benzene, naphthalene, anthracene, biphenyl, indene, indane, 1,2-dihydronapthalene, 1,2,3,4-tetrahydronapthalene, and the like. Aryl groups may be optionally substituted independently with one or more substituents described herein.

As used herein, the term "heteroaryl," by itself or in combination with another term, means, unless otherwise stated, an aryl group that contain the stated number of carbon atoms and at least one heteroatom selected form nitrogen (N), oxygen (O), sulfur (S), and silicon (Si). The heteroatom(s) O, N, S, and Si may be placed at any position of the heteroaryl or at the position at which the aryl group is attached to the remainder of the molecule. Examples of heteroaryl groups include, but are not limited to, pyrrole, pyrazole, pyrimidine, pyrazine, pyridine, quinoline, thiophene, 1,2,3-triazole, 1,2,4-triazole, thiazole, oxazole, isothiazole, iso-oxazole, imidazole, furan and the like. The heteroaryl group can be optionally substituted.

As used herein, the term "halo" or "halogen," by themselves or as part of another substituent, mean, unless otherwise stated, a fluorine, chlorine, bromine, or iodine atom.

The term "substituted" refers to a chemical group, such as alkyl, cycloalkyl aryl, and the like, wherein at least one hydrogen is replaced with a substituent as described herein, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, $-CF_3$, $-CN$, or the like. The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms. This disclosure is not intended to be limited in any manner by the permissible substituents of organic compounds. In many embodiments, however, any single substituent has fewer than the 100 total atoms. In many embodiments, however, any single substituent has fewer than the 10 total atoms.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

As used herein, the neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

The term "treatment" or "treating" as used herein is intended to encompass preventing the onset, slowing the progression, reversing or otherwise ameliorating a neurological (neurodegenerative and neuromuscular) disorder. In one exemplary embodiment, the neurological disorder being treated is ALS.

The term "therapeutically effective amount" refers to an amount effective, at dosages and for periods of time necessary, to achieve the desired therapeutic result. A therapeutically effective amount of the composition may vary according to factors such as the disease state, age, sex, and weight of the individual, and the ability of the pharmacological agent to elicit a desired response in the individual. A therapeutically effective amount is also one in which any toxic or detrimental effects of the pharmacological agent are outweighed by the therapeutically beneficial effects.

The term "ViaIncTot" refers to the total increase in cell viability (AUC) in the presence of tunicamycin dose-response-induced proteostasis.

The term "CmpViaTot" refers to the total change in cell viability (AUC) caused by compound alone in the absence of tunicamycin.

The term "PlossBuff" refers to the percent of parent compound lost when incubated in phosphate buffer.

The term "SgainBuff" refers to the percent of parent compound converted to salubrinal when incubated in phosphate buffer.

The term "PlossPlas" refers to the percent of parent compound lost when incubated in mouse plasma.

The term "SgainPlas" refers to percent of parent compound converted to salubrinal when incubated in mouse plasma.

The term "Liver–" refers to the percent of parent compound lost when incubated in mouse liver microsomes without NADPH cofactor.

The term "Liver+" refers to the percent of parent compound lost when incubated in mouse liver microsomes with NADPH cofactor present.

The term "about" or "approximately" means within an acceptable error range for the particular value as determined by one of ordinary skill in the art, which will depend in part on how the value is measured or determined—e.g., the limitations of the measurement system, or the degree of precision required for a particular purpose. For example, "about" can mean within 1 or more than 1 standard deviations, as per the practice in the art. Alternatively, "about" can mean a range of up to 20%, preferably up to 10%, more preferably up to 5%, and more preferably still up to 1% of a given value. Where particular values are described in the application and claims, unless otherwise stated, the term "about" meaning within an acceptable error range for the particular value should be assumed.

As used herein and in the appended claims, the singular forms "a," "an," and "the," include plural referents unless the context clearly indicates otherwise. Thus, for example, reference to "a molecule" includes one or more of such molecules and reference to "the method" includes reference to equivalent steps and methods known to those of ordinary skill in the art that could be modified or substituted for the methods described herein.

Amyotrophic Lateral Sclerosis

Amyotrophic Lateral Sclerosis (ALS) is a neurodegenerative condition in which patients progressively lose all motor function. Evidence is accumulating that as a result of the aging process the body increasingly loses the ability to adequately degrade mutated or misfolded proteins. The proteasome is the piece of biological machinery responsible for most normal degradation of proteins inside cells. Age related loss of function or change of function of the proteasome is now thought to be at the heart of many neurodegenerative conditions, including Alzheimer's disease, Parkinson's disease, Huntington's disease, and ALS.

ALS, also called Lou Gehrig's disease, affects the motor neurons of the cortex, brain stem and spinal cord. (Hirano, A., "Neuropathology of ALS: an overview," *Neurology*, 47(4 Suppl. 2): S63-6 (1996)). ALS affects approximately 30,000 Americans with nearly 8,000 deaths reported in the US each year. ALS remains one of the most devastating diseases and advances in treatment are desperately needed.

The cardinal feature of ALS is the loss of spinal motor neurons, which causes the muscles under their control to weaken and waste away leading to paralysis. ALS has both familial (5-10%) and sporadic forms and the familial forms have now been linked to several distinct genetic loci (Deng, H. X., et al., "Two novel SOD1 mutations in patients with familial amyotrophic lateral sclerosis," *Hum. Mol. Genet.*, 4(6): 1113-16 (1995); Siddique, T. and A. Hentati, "Familial amyotrophic lateral sclerosis," *Clin. Neurosci.*, 3(6): 338-47(1995); Siddique, T., et al., "Familial amyotrophic lateral sclerosis," *J. Neural Transco. Suppl.*, 49: 219-33(1997); Ben Hamida, et al., "Hereditary motor system diseases (chronic juvenile amyotrophic lateral sclerosis). Conditions combining a bilateral pyramidal syndrome with limb and bulbar amyotrophy," *Brain*, 113(2): 347-63 (1990); Yang, Y., et al., "The gene encoding alsin, a protein with three guanine-nucleotide exchange factor domains, is mutated in a form of recessive amyotrophic lateral sclerosis," *Nat. Genet.*, 29(2): 160-65 (2001); Hadano, S., et al., "A gene encoding a putative GTPase regulator is mutated in familial amyotrophic lateral sclerosis 2," *Nat. Genet.*, 29(2): 166-73 (2001)). About 15-20% of familial cases are due to mutations in the gene encoding Cu/Zn superoxide dismutase 1 (SOD1) (Siddique, T., et al., "Linkage of a gene causing familial amyotrophic lateral sclerosis to chromosome 21 and evidence of genetic-locus heterogeneity," *N. Engl. J. Med.*, 324(20): 1381-84 (1991); Rosen, D. R., et al., "Mutations in Cu/Zn superoxide dismutase gene are associated with familial amyotrophic lateral sclerosis." Nature, 362(6415): 59-62 (1993)).

Although ALS is characterized by loss of motor neurons in the spinal cord resulting in muscle atrophy, the disease also manifests itself with changes in protein folding, protein aggregation, and mitochondrial dysfunction. Early symptoms of ALS include increasing muscle weakness, particularly in the arms and legs, and in the muscles associated with speech, swallowing and breathing. Symptoms of weakness and muscle atrophy usually begin asymmetrically and distally in one limb, and then spread within the neuroaxis to involve contiguous groups of motor neurons. Symptoms can begin either in bulbar or limb muscles. Clinical signs of both lower and upper motor neuron involvement are required for a definitive diagnosis of ALS. Respiration is usually affected late in limb onset patients, but occasionally can be an early manifestation in patients with bulbar onset symptoms.

Multiple Sclerosis

Multiple Sclerosis (MS) is a chronic disease that is characterized by "attacks," during which areas of white matter of the central nervous system, known as plaques, become inflamed. Inflammation of these areas of plaque is followed by destruction of myelin, the fatty substance that forms a sheath or covering that insulates nerve cell fibers in the brain and spinal cord. Myelin facilitates the smooth, high-speed transmission of electrochemical messages between the brain, spinal cord, and the rest of the body. Damage to the myelin sheath can slow or completely block the transmission of these electrochemical messages, which can result in diminished or lost bodily function.

The most common course of MS manifests itself as a series of attacks, which are followed by either complete or partial remission, during which the symptoms lessen only to return at some later point in time. This type of MS is commonly referred to as "relapsing-remitting MS." Another form of MS, called "primary-progressive MS," is characterized by a gradual decline into the disease state, with no distinct remissions and only temporary plateaus or minor relief from the symptoms. A third form of MS, known as "secondary-progressive MS," starts as a relapsing-remitting course, but later deteriorates into a primary-progressive course of MS.

The symptoms of MS can be mild or severe, acute or of a long duration, and may appear in various combinations. These symptoms can include vision problems such as blurred or double vision, red-green color distortion, or even blindness in one eye, muscle weakness in the extremities, coordination and balance problems, muscle spasticity, muscle fatigue, paresthesias, fleeting abnormal sensory feelings such as numbness, prickling, or "pins and needles" sensations, and in the worst cases, partial or complete paralysis. About half of the people suffering from MS also experience cognitive impairments, such as for example, poor concentration, attention, memory and/or judgment. These cognitive symptoms occur when lesions develop in those areas of the brain that are responsible for information processing.

Experimental autoimmune encephalomyelitis (EAE) is an experimental autoimmune disease of animals that is thought to model aspects of multiple sclerosis (Zamvil et al. (1990) Annu. Rev. Immunol. 8: 579-621). EAE can be induced in susceptible strains of rats, such as the Lewis rat, by immunization to myelin basic protein (MBP) in complete Freund's adjuvant (CFA), an emulsion of mineral oil containing killed Mycobacteria. The disease develops about 12 days after immunization and is characterized by paralysis of various degrees due to inflammation of the central nervous system. The paralysis can last up to 6 or 7 days and the rats usually recover unless they die during the peak of their acute paralysis. EAE is caused by T cells that recognize defined determinants of the MBP molecule. The major MBP determinant in the Lewis rat is composed of the peptide sequence 71-90 (Zamvil et al. Supra).

Alternatively, in vitro cell lines for MS can also be used. Such in vitro cell lines include, but are not limited to, the LM7PC and PLI-2 cell lines. These two continuous cell lines were derived from human choroid plexus cells originating from two different patients suffering from MS obtained by a culture method described in the document WO-A-9320188 and U.S. Pat. No. 6,342,383 to Perron et al.

Alzheimer's Disease

Alzheimer's disease is a progressive, neurodegenerative disease that affects the portions of the brain that control thought, memory and language. This disease is characterized by progressive dementia that eventually results in substantial impairment of both cognition and behavior. The disease manifests itself by the presence of abnormal extracellular protein deposits in brain tissue, known as "amyloid plaques," and tangled bundles of fibers accumulated within the neurons, known as "neurofibrillary tangles," and by the loss of neuronal cells. The areas of the brain affected by Alzheimer's disease can vary, but the areas most commonly affected include the association cortical and limbic regions. Symptoms of Alzheimer's disease include memory loss, deterioration of language skills, impaired visuospatial skills, and impaired judgment, yet those suffering from Alzheimer's retain motor function.

Alzheimer's disease is characterized by two hallmark pathological features that involve protein misfolding: Neurofibrillary tangles (NFTs) formed by paired helical filaments (PHFs) from abnormally modified Tau protein and senile plaques composed of beta-amyloid (A.beta.) (See Price, et al., (1998) Annu Rev Neurosci 21: 479-505). Mild cognitive impairment (MCI) is observed in Alzheimer's disease and is thought to represent the prodromal stage of Alzheimer's disease. MCI accompanies neuronal loss in Alzheimer's disease. Dementia and neuronal loss in Alzheimer's disease correlate significantly with levels of Tau pathology and resulting NFTs. Evidence for altered/reduced proteasomal activity in Alzheimer's disease has been found that may result from the defective ubiquination and/or breakdown of misfolded proteins such as PHF-Tau and beta amyloid by the 20S proteasome (Keck, et al. (2003) J Neurochem 85:115-22; Keller et al. (2000) J Neurochem 75: 436-9; and Lopez et al., (2003) Exp Neurol 180: 131-43). Additionally, a mutant form of ubiquitin (Ub+1), generated by molecular misreading, was observed in the brains of Alzheimer's disease patients including those with the non-familial Alzheimer's disease (van Leeuwen, et al. (1998) Science 279: 242-7; and Lam, et al., (2000) Proc Natl Acad Sci USA 97: 9902-6). Ub+1 capped polyUb chain was also able to inhibit proteasomal activity in vitro and may induce accumulation of misfolded proteins and contribute to both A.beta. and Tau pathology in Alzheimer's disease (Lam, et al., (2000) Supra).

Proteasomal dysregulation can lead to a variety of cellular alterations that can contribute to chronic neurodegeneration some of which include polyamine dysregulation and cell cycle dysregulation, inflammation and apoptosis (See e.g., Jesenberger, et al. (2002) Nat Rev Mol Cell Biol 3: 112-21; Li, et al. (2003) Int J Biochem Cell Biol 35: 547-52; Bernstein, et al. (1995) Neurosci Lett 186:123-6; and Trojanowski et al. (2000) Ann NY Acad Sci 924: 62-7). Expression of cell cycle regulating gene products and induction of DNA replication (clear indications of cell cycle re-entry) has been demonstrated in Alzheimer's disease and Parkinson's disease (Jordan-Sciutto, et al. (2002) J Neuropathol Exp Neurol 61: 358-67; Klein, et al. (2003) J Clin Invest 111: 785-93; Nouspikel, et al. (2003) Bioessays 25: 168-73; and Yang, et al. (2001) J Neurosci 21: 2661-8). Most recently Yang et al demonstrated that the cell cycle induction in Alzheimer's disease is observed during both the early prodromal stage (MCI) and in the advanced stages of Alzheimer's disease indicating that neurons dwell in an unproductive cell cycle for many months before finally committing to apoptosis (Yang, et al. (2003) J Neurosci 23: 2557-63). The protective effect of flavopiridol, a pan-CDK inhibitor, in a model of proteasome inhibition-induced neuronal death, together with the finding of cycling CDK induction in an in vitro A.beta. model of Alzheimer's disease demonstrate a link between proteasomal dysfunction and cell cycle dysregulation and neuronal death (Jordan-Sciutto, et al. (2001) Mech Ageing Dev 123: 11-20; and Rideout, et al. (2003) J Neurosci 23: 1237-45).

A suitable animal model for Alzheimer's disease that mimics the pathology of the disease in humans can be one in which a selective lesion is placed in a subcortical nucleus (nucleus basalis of Meynert) with a resultant cortical cholinergic deficiency, similar in magnitude to that seen in early to moderate stage Alzheimer's disease. Numerous behavioral deficits, including the inability to learn and retain new information, are characteristic of this lesion. Pharmacological agents that can normalize these abnormalities would have a reasonable expectation of efficacy in Alzheimer's disease (See e.g., Haroutunian, et al. (1985) Life Sciences, 37:945-952).

In addition to in vivo models, a number of in vitro cell lines can also be used to examine the effects of pharmacological agents on Alzheimer's disease such as apolipoprotein E uptake and low-density lipoprotein receptor-related protein expression by the NTera2/D1 cell line, a cell culture model for late-onset Alzheimer's disease (See e.g., Williams et al. (1997) Neurobiol. of Disease, 4:58-67). Alternatively, human melanocytes can be used as a model system for studies of Alzheimer's disease (See e.g., Yaar et al. (1997) Arch. Dermatol. 133:1287-291).

Parkinson's Disease

Parkinson's disease is a motor system disorder caused by the loss of nerve cells, or neurons, found in the substantia nigra region of the mid-brain. These neurons produce dopamine, a chemical messenger molecule that is found in the brain and helps control or direct muscle activity. Dopamine is used by the cells of the substantia nigra as a neurotransmitter to signal other nerve cells. Parkinson's disease occurs when these neurons die or become impaired, thereby decreasing dopamine levels within the brain. Loss of dopamine causes the neurons to fire uncontrollably, which leaves patients unable to direct or control their bodily movement in a normal manner. The four main symptoms of Parkinson's disease are trembling in the hands, arms, legs, jaw and face; stiffness of the limbs and/or trunk; a slowness of movement, referred to as bradykinesia; and impaired balance and/or coordination. Parkinson's disease is both chronic, i.e., it persists over a long period of time, and progressive, i.e., the symptoms grow worse over time.

Animal models of Parkinson's disease are well established, such as the primate model of Parkinson's Disease described by Zamir et al. (1984) Brain Res. 322, 356-60. Neurodegenerative disease-causing substance can be used to cause a neurodegenerative disease in a mammal. Examples of such substances include N-methyl-4-phenyl-1,2,3,6-tetrahydropyridine (MPTP), 1-methyl-4-henylpyridine (MPP-.sup.+) and manganese dust for Parkinson's disease; quinolinic acid for Huntington's chorea; and beta-N-methylamino-L-alanine for amyotrophic lateral sclerosis, Parkinson's disease and Alzheimer's disease. Due to their mimicry of effects of Parkinson's disease, treatment of animals with methamphetamine or MPTP has been used to generate models for Parkinson's disease. The end result of MPTP administration is the destruction of the striatum in the brain, an area in the neocortex limbic system in the subcortical area in the center of the brain, an area compromised in Parkinson's disease. The neurotransmitter dopamine is concentrated in the striatum Parkinson's disease is characterized by lesions in that area of the brain and by depleted dopamine levels. In some species (primates) the striatal degeneration has been reported to be accompanied by behavioral symptoms that mimic Parkinson's symptoms in humans (See e.g., Markey, et al. (1986) Medicinal Research Reviews 6:389-429).

Huntington's Disease

Huntington's disease is a hereditary disorder caused by the degeneration of neurons in certain areas of the brain. This degeneration is genetically programmed to occur in certain areas of the brain, including the cells of the basal ganglia, the structures that are responsible for coordinating movement. Within the basal ganglia, Huntington's disease specifically targets nerve cells in the striatum, as well as cells of the cortex, or outer surface of the brain, which control thought, perception and memory. Neuron degeneration due to Huntington's disease can result in uncontrolled movements, loss of intellectual capacity and faculties, and emotional disturbance, such as, for example, mood swings or uncharacteristic irritability or depression.

As discussed above, neuron degeneration due to Huntington's disease is genetically programmed to occur in certain areas of the brain. Studies have shown that Huntington's disease is caused by a genetic defect on chromosome 4, and in particular, people with Huntington's disease have an abnormal repetition of the genetic sequence CAG in the Huntington's disease gene, which has been termed IT15. The IT15 gene is located on the short arm of chromosome 4 and encodes a protein called huntingtin. Exon I of the IT15 gene contains a polymorphic stretch of consecutive glutamine residues, known as the polyglutamine tract (Rubinsztein, (2002) TRENDS in Genetics, 18: 202-9). Asymptomatic individuals typically contain fewer than 35 CAG repeats in the polyglutamine tract. Murine models for HD include that described by Hayden et al. in U.S. Pat. No. 5,849,995, as well as in vitro systems as described in U.S. Pat. No. 5,834,183 to Orr et al.

Prion-Associated Diseases

The prion protein (PrP) is closely associated with a group of fatal neurodegenerative diseases (Ma, et al. (2001) Proc. Natl. Acad Sci., 98:14955-14960). This group of disorders is characterized by vacuolation of the brain's gray matter, also known as spongioform change. These diseases can take a variety of forms. For example, these diseases can be sporadic, dominantly heritable, as well as transmissible disorders. In humans, the most prevalent form of prion disease is Creutzfeldt-Jakob disease, while in animals, the most common form is known as scrapie. Other disorders in this group include kuru, Gerstmann-Straussler-Scheinker disease and fetal familial insomnia. All disorders are invariably fatal.

In particular, the symptoms of Creutzfeldt-Jakob disease include a rapidly progressive deterioration of intellectual abilities (also known as dementia). The median duration of this illness, from on-set of symptoms to death is around four months. As the disease state progresses, the dementia is typically accompanied by other symptoms such as ataxia, muscular rigidity, and spontaneous and irregular limb jerks, also known as myoclonus.

Spinocerebellar Ataxia

Ataxias are diseases wherein a person loses the ability to coordinate muscle activity during voluntary muscle contraction, and therefore, loses the ability to coordinate smooth bodily movements. Spinocerebellar ataxia is the most common form of hereditary ataxia. Symptoms of the on-set of spinocerebellar ataxia include limb ataxia, nystagmus (rhythmical oscillation of the eyeballs, in either a pendular or jerky motion), kyphoscoliosis (a deformity of the spine characterized by extensive flexion), and pes cavus (a contracted foot, or exaggeration of the normal arch of the foot). The major pathological changes that occur with the disease state occur in the posterior columns of the spinal cord. Spinocerebellar ataxia is most often an autosomal recessive inherited disorder.

Among the adult-onset dominant spinocerebellar ataxias (SCAs), seven different loci have been mapped (Gispert et al. (1993) Nature Genet. 4, 295-299; Takiyama et al. (1993) Nature Genet. 4, 300-304; Gardner et al. (1994) Neurology, 44: A361; Nagafuchi et al. (1994) Nature Genet. 6: 14-18; Ranum et al. (1994) Nature Genet. 8, 280-284; Benomar et al. (1995) Nature Genet. 10: 84-88; Gouw et al. (1995) Nature Genet. 10: 89-93; Zhuchenko et al. (1997) Nature Genet. 15: 62-69). Approximately sixty percent of the dominant ataxias result from expansions in trinucleotide CAG repeats at the SCA1, 2, 3, 6 or 7 loci (Nagafuchi et al. (1994) Nature Genet. 6: 14-18; Zhuchenko et al. (1997) Nature Genet. 15: 62-69; Orr et al. (1993) Nature Genet. 4: 211-226; Kawaguchi et al. (1994) Nature Genet. 8: 221-228; Koide et al. (1994) Nature Genet. 6: 9-13; Imbert et al. (1996) Nature Genet. 14: 285-291; Pulst et al. (1996) Nature Genet. 14: 269-276; Sanpei et al. (1996) Nature Genet. 14: 277-284; David et al. (1997) Nature Genet. 17: 65-70; Koob et al. (1998) Nature Genet. 18: 72-75. The substantial clinical variability among the remaining 40% of the genetically undefined dominant families suggests that a number of additional ataxia coding sequences remain to be identified. Suitable models are, for example the SCA7 murine model displaying neurodegeneration with progressive ataxin-7 accumulation (See e.g. Yvert et al. (2001) Hum Mol Genet. 10:1679-92), as well as in vitro systems as described in U.S. Pat. No. 5,834,183 to Orr et al.

Spinal Muscular Atrophy

Spinomuscular atrophy (SMA) is a disease of the anterior horn cells of the spinal cord. There are several different types of SMA, including Type I or Acute (Severe) SMA, which is also known as Werdnig-Hoffmann Disease, Type II (Chronic) SMA, Type III (Mild) SMA, often referred to as Kugelberg-Welander or Juvenile SMA, Type IV (Adult Onset) SMA, and Adult Onset X-Linked SMA, also known as Kennedy's Syndrome or Bulbo-Spinal Muscular Atrophy, which occurs in males, but females may be carriers. SMA affects the voluntary muscles that are responsible for activities such as crawling, walking, head and neck control, and swallowing. SMA mainly affects the proximal muscles, or the muscles closes to the trunk of a person's body. Symptoms include weakness in the legs and arms, with weakness in the legs being greater than weakness in the arms. Other symptoms may include tongue fasciculations, or abnormal movements of the tongue. During the course of SMA, however, a person's senses, feelings and intellectual activity remain unaffected.

Suitable animal models of spinal muscular atrophy include, but are not limited to, the murine models described Fricker, (2000) Drug Discovery Today 5:220-221; Frugier, et al. (2000) Human Molecular Genetics 9:849-858; Hsieh-Li, et al. (2000) Natural Genetics 24:66-70; and Monani, et al. (2000) Human Molecular Genetics 9:333-339. In vitro systems of spinal muscular atrophy can be those described by Yoshida, et al. (1990) J. Biol. Chem. 265:17174-17179.

Endoplasmic Reticulum (ER) Stress

Endoplasmic reticulum is an organelle responsible for folding, post-translational modifications and transport of secretory, luminal and membrane proteins. This organelle, therefore, plays an important role in maintaining cellular homeostasis. Endoplasmic reticulum (ER) stress is a condition that is accelerated by accumulation of unfolded or misfolded proteins after the disturbance of the ER environment, which can be triggered by a variety of physiological and pathological factors, such as nutrient deprivation, altered glycosylation, calcium depletion, oxidative stress, DNA damage and energy disturbance. The ER stress may initiate the unfolded protein response (UPR) to restore cellular homeostasis or lead to apoptosis.

At the early stages of ER stress, the failure of molecular chaperones break the maintenance of proteostasis (Kelly et al., 2007; Naido et al., 2009). To overcome the deleterious effects of ER stress, a series of adaptive and protective strategies are initiated. For example, owing to the abundance of unfolded or misfolded proteins accumulated in the ER, new protein synthesis is inhibited. To clear the accumulated proteins, many chaperone genes are induced at the transcriptional level and activate the ER-associated degradation (ERAD) system, which can translocate and remove misfolded proteins through proteasomal degradation. These processes are identified as the unfolded protein response (UPR) (Meusser et al., 2005; Lynch et al., 2012). However, if unresolved, ER stress can be lethal to cells via what is recognized as ER stress induced apoptosis (Zeng et al., 2015).

The UPR is a concerted and complex cellular response that is mediated through three ER transmembrane receptor proteins, such as the double-stranded RNA-activated protein kinase like endoplasmic reticulum kinase (PERK), inositol-requiring enzyme 1 (IRE1, also called ERN1) and activating transcription factor 6 (ATF6) (Promlek et al., 2011; Teske et al., 2011).

The ER transmembrane receptor protein PERK is a member of the eukaryotic translation initiation factor 2α (eIF2α) kinase subfamily, together with RNA-dependent protein kinase (PKR), general control nondepressible 2 kinase (GCN2) and heme-regulated eIF2α kinase (HRI) (Hardin et al., 1999). PERK possesses a luminal domain like IRE1 and a cytoplasmic portion that manifests protein serine/threonine kinase activity, and it has a PKR-like catalytic domain, which most importantly phosphorylates eIF2α (Shi et al., 1998). eIF2 has three subunits, i.e., α, β, and γ, and eIF2α is a translation initiation factor that functions in the early steps of protein synthesis by forming a ternary complex with GTP and initiator tRNA. This complex binds to a 40S ribosomal subunit, followed by mRNA binding to constitute a 43S preinitiation complex. Junction of the 60S ribosomal subunit to form the 80S initiation complex is preceded by hydrolysis of the GTP bound to eIF2 and release of an eIF2-GDP binary complex. In order to make eIF2 recycle and then to catalyze another round of initiation, the GDP bound to eIF2 typically must exchange with GTP by way of the reaction catalyzed by eIF2β. Here, eIF2α phosphorylation is key to stabilize the eIF2/GDP/eIF2β complex and prevent the GDP/GTP exchange reaction. Therefore, eIF2α phosphorylation impairs the recycling of eIF2 between successive rounds of initiation and leads to global inhibition of translation at early stages of ERS.

Because ER stress plays an essential role in many diseases, such as neurodegenerative disease like amyotrophic lateral sclerosis, drugs targeting ER stress and its different actors are good candidates for possible cures. Several drugs and natural products have been proposed to hinder ER stress such as Salubrinal.

Dephosphorylation Inhibitors

Salubrinal, a cinnamamide derivative, has been shown to prevent eIF2α dephosphorylation by inhibiting the protein complex GADD34/protein phosphatase 1 (PP1), which consists of the general cellular serine/threonine phosphatase PP1 and the non-enzymatic cofactor GADD34 (Boyce et al., 2005; Long et al., 2005). As discussed above, the eIF2α phosphorylation appears to be cytoprotective during ER stress by inhibiting the translation initiation activity of eIF2α, which reduces global protein synthesis and results in a reduction of the ER workload (Hotamisligil et al., 2010). For instance, activating transcription factor 4 (ATF4), a transcription factor that induces the expression of UPR target genes, is produced through alternative translation and thus not inhibited by phosphorylation of eIF2α (Iniga et al., 2010; and Hotamisligil et al., 2010).

Salubrinal appears to be a candidate compound for cytoprotection against endoplasmic reticulum stress and the unfolded protein response that leads to numerous diseases. However, it is not an ideal candidate to prevent eIF2α dephosphorylation because of its low solubility in aqueous solutions, rapid clearance and relatively high toxicity in animals (EC50~15 μM).

Salubrinal Analogs

A class of dephosphorylation inhibitors of eIF2-alpha according to the invention can be defined by the compounds of Formula (II), Salubrinal analogs (excluding Salubrinal itself):

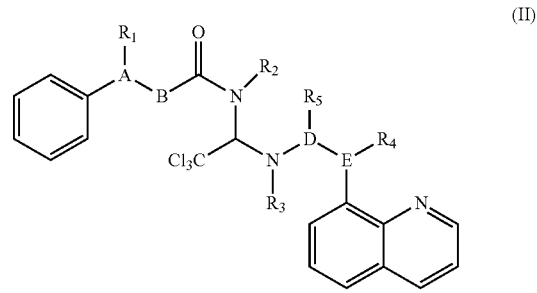

(II)

In some embodiments, $R^1$ is H, $C_{3-6}$ cycloheteroalkyl, or $N(CH_3)(CH_3)$, $R^2$ is H, $C_{3-6}$ cycloheteroalkyl, or when combined with $R^4$ is together —$CH(C_{1-5}heteroalkyl)$—, $R^3$ is H, $CH_2(C_{3-6}cycloheteroalkyl)$, $C_{3-6}$ cycloheteroalkyl, amino acid, amino acid derivative, or $C_{1-10}$heteroalkyl, $R^4$ is null, H, $CH_2(C_{3-6}$ cycloheteroalkyl), $C_{3-6}$ cycloheteroalkyl, amino acid, amino acid derivative, or $C_{1-10}$ heteroalkyl, $R^5$ is =S, $CH_2(C_{3-6}$ cycloheteroalkyl), $C_{3-6}$ cycloheteroalkyl, amino acid, amino acid derivative, or $C_{1-20}$ heteroalkyl, A-B is CH—$CH_2$ or CH=CH, and D-E is C—N, CH—N, or C=N.

Examples of compounds according to the Formula (II) are provided in tables I and II below. Each of the compounds in these table has a potency to inhibit, for example and without limitation, the dephosphorylation of eIF2-alpha.

TABLE 1

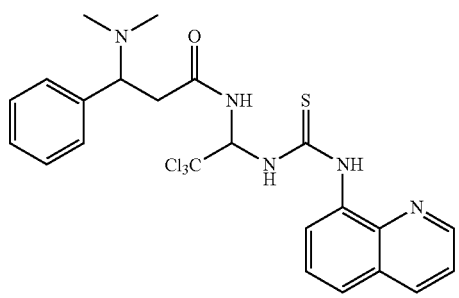

1

TABLE 1-continued
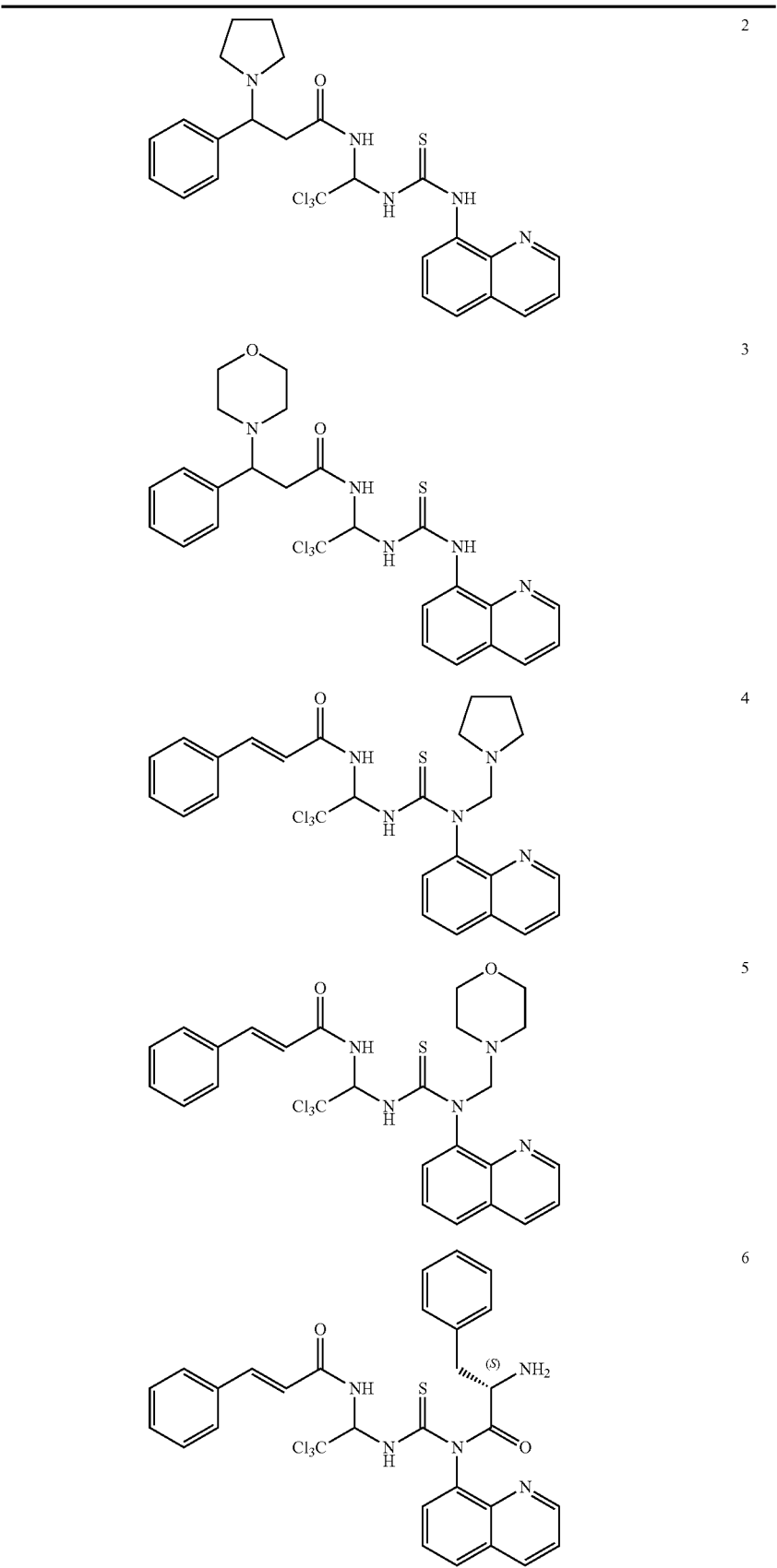

TABLE 1-continued
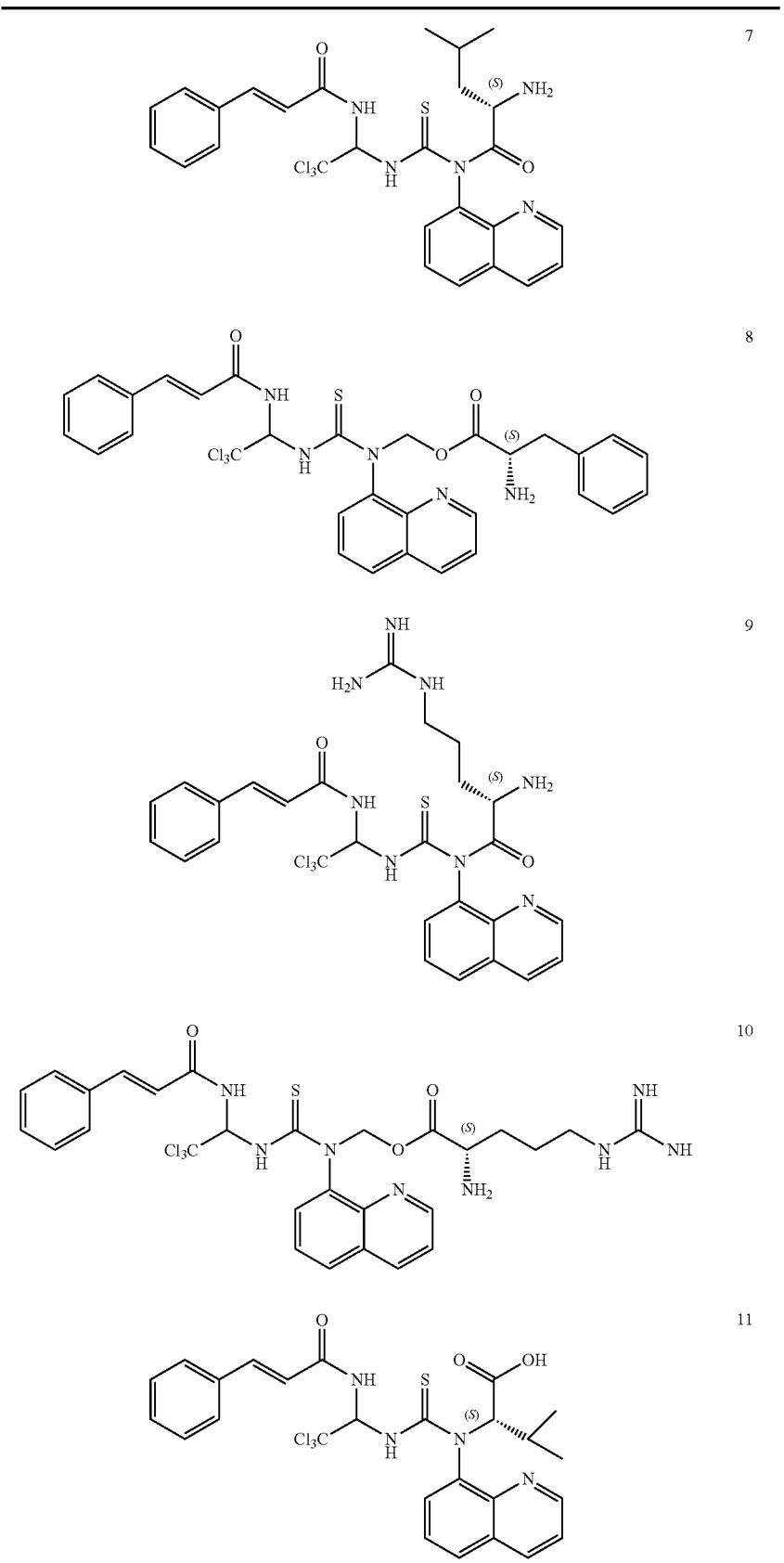

TABLE 1-continued
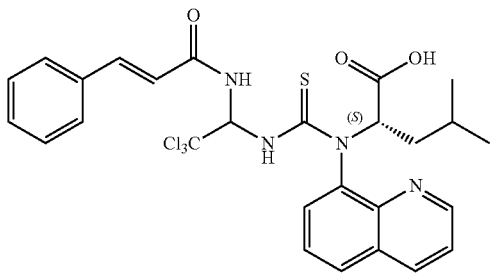
12
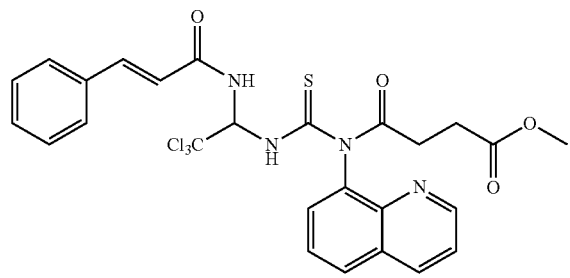
13
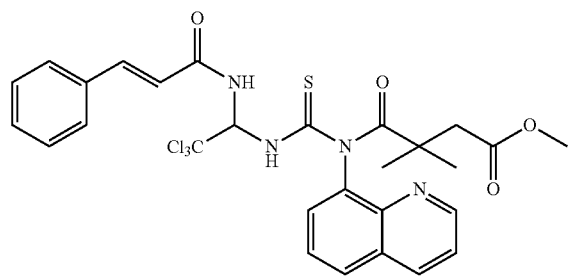
14
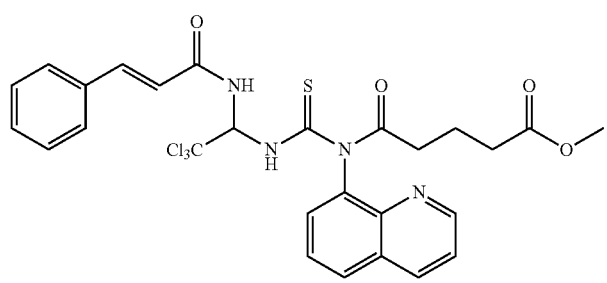
15
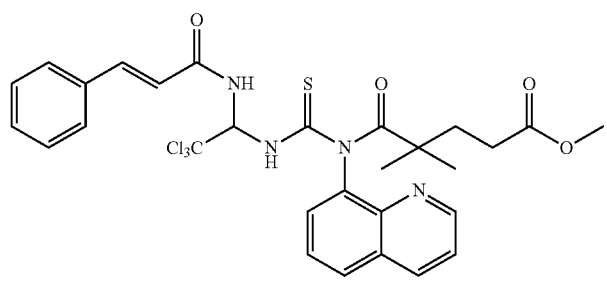
16

TABLE 1-continued
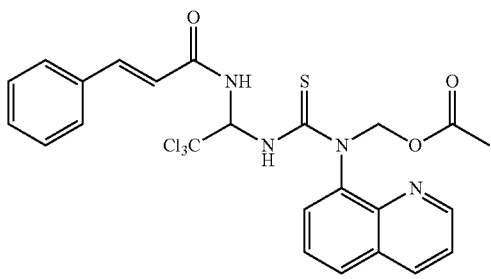
17
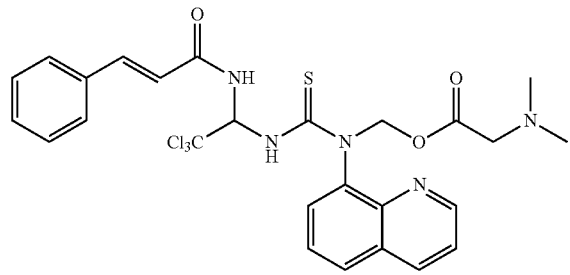
18
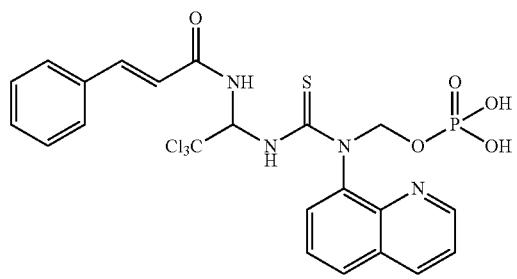
19
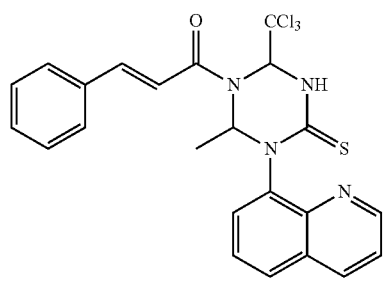
20
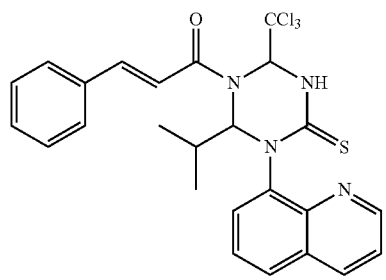
21

TABLE 1-continued
| | |
|---|---|
| 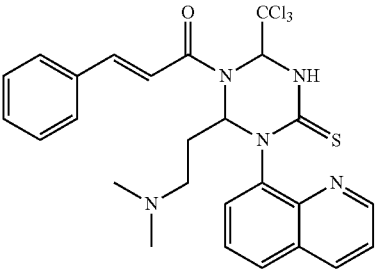 | 22 |
| 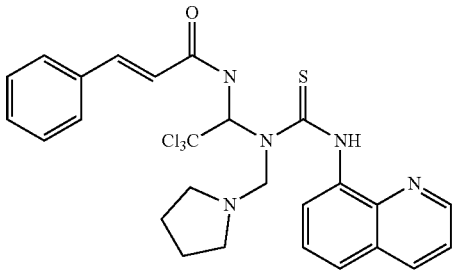 | 23 |
| 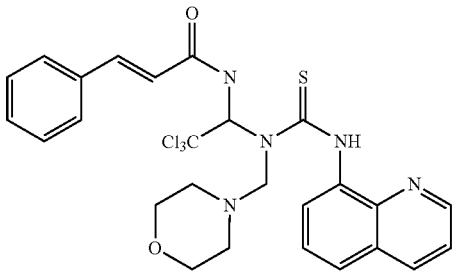 | 24 |
| 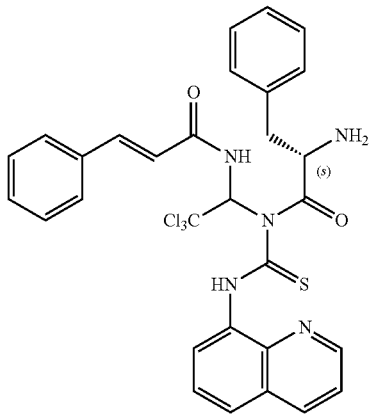 | 25 |
| 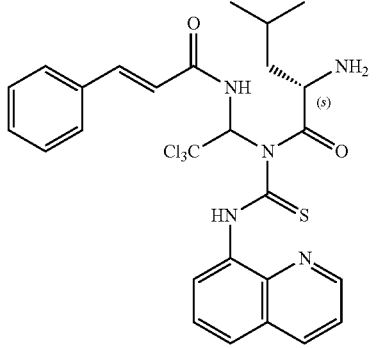 | 26 |

TABLE 1-continued
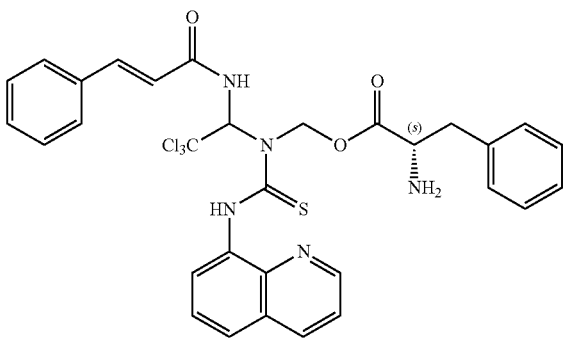
27
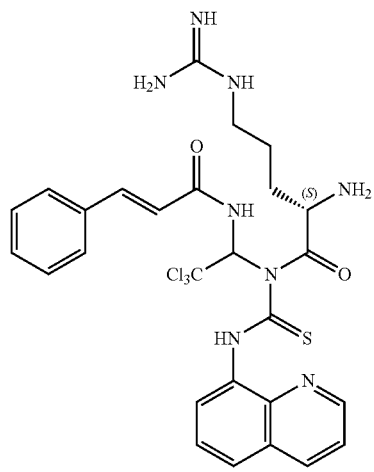
28
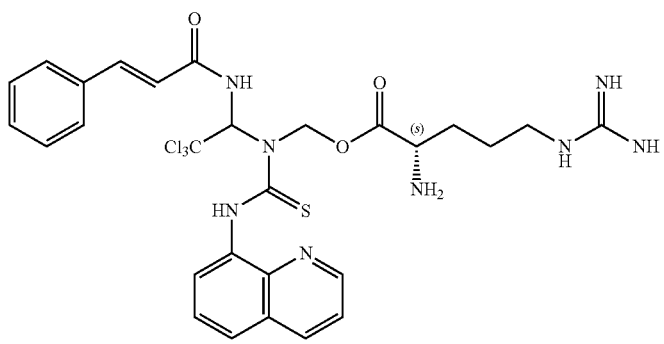
29
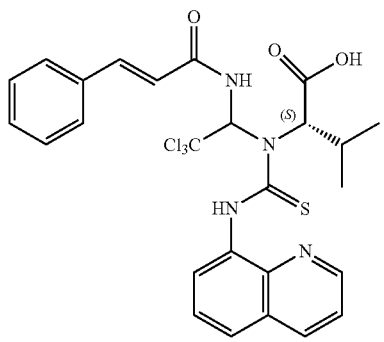
30

TABLE 1-continued
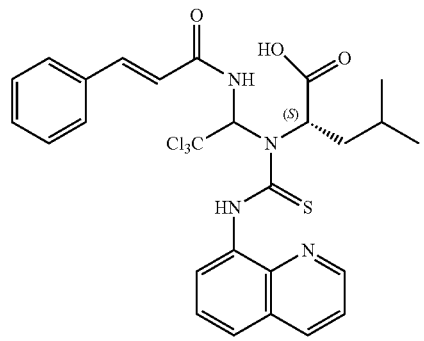 31
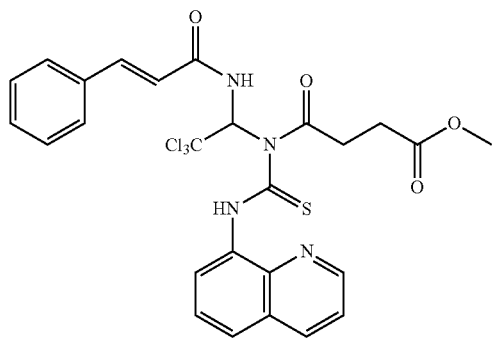 32
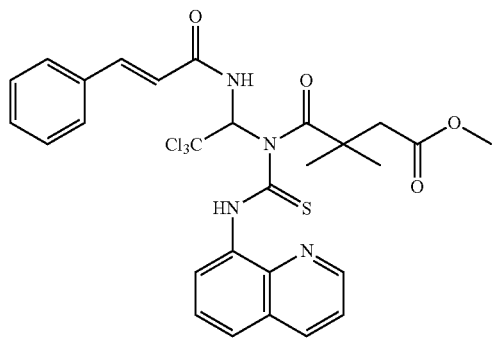 33
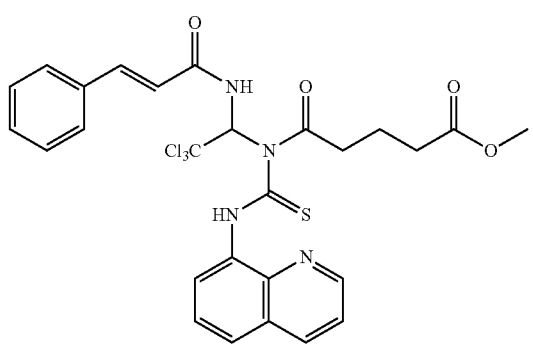 34

TABLE 1-continued
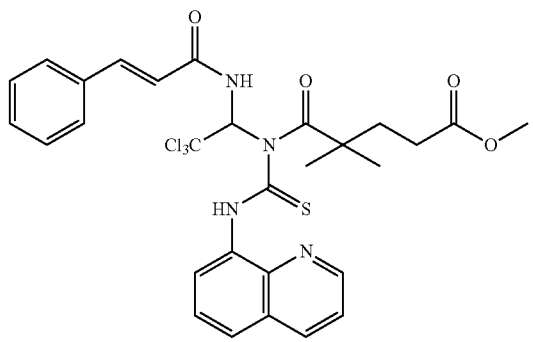
35
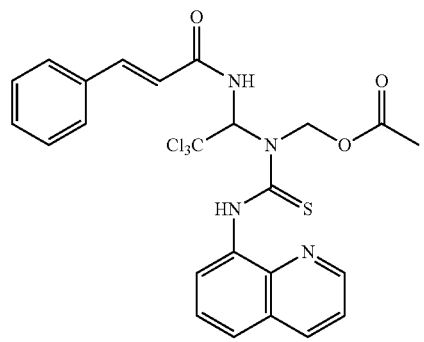
36
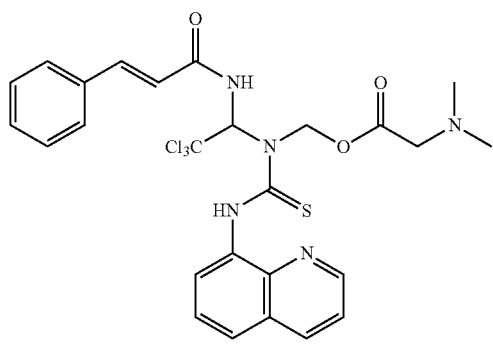
37
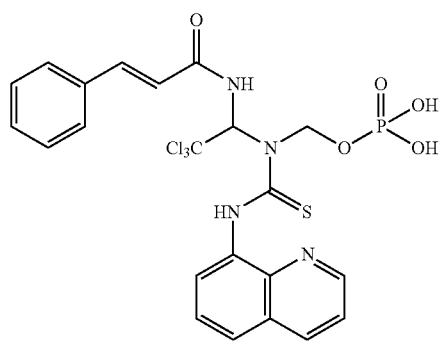
38

TABLE 2

| ID | Structure | Formula | M.W. |
|---|---|---|---|
| 1901 | 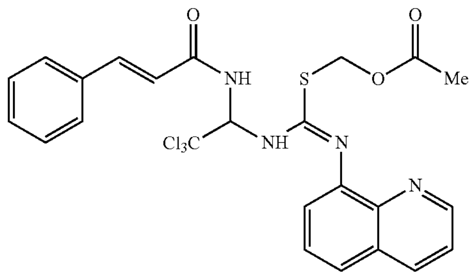 | C24H21Cl3N4O3S | 551.87 |
| 1902 | 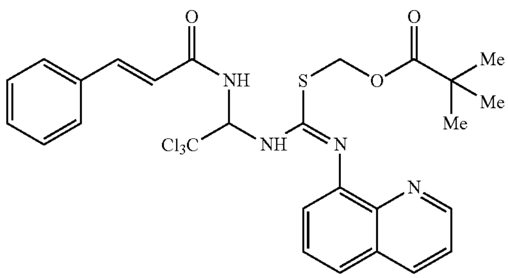 | C27H27Cl3N4O3S | 593.95 |
| 1903 | 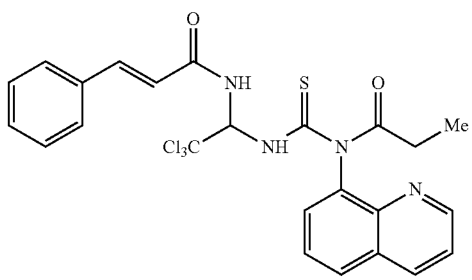 | C24H21Cl3N4O2S | 535.87 |
| 1904 | 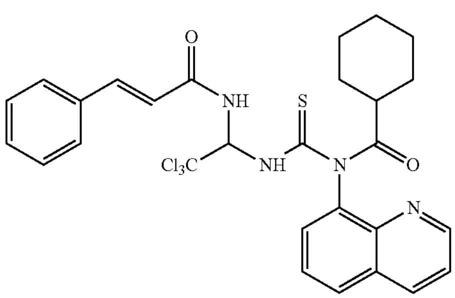 | C28H27Cl3N4O2S | 589.09 |
| 1905 | 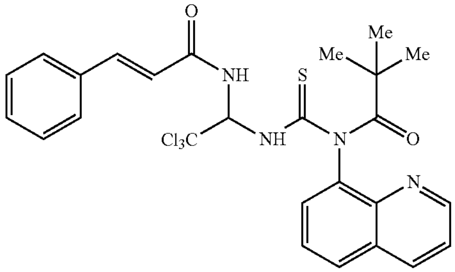 | C26H25Cl3N4O2S | 563.93 |

TABLE 2-continued

| ID | Structure | Formula | M.W. |
|---|---|---|---|
| 1906 | 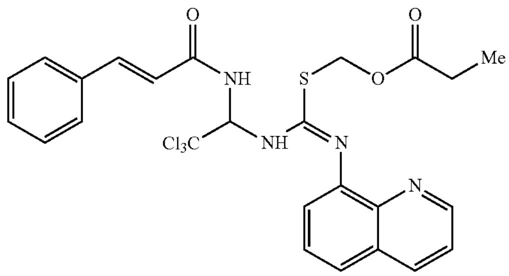 | C25H23Cl3N4O3S | 565.9 |
| 1907 | 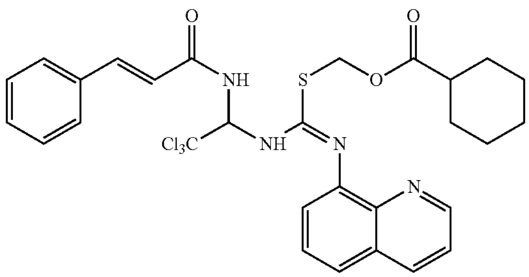 | C29H29Cl3N4O3S | 619.99 |
| 1908 | | C35H25Cl3N4O3S | 688.02 |
| 1909 | 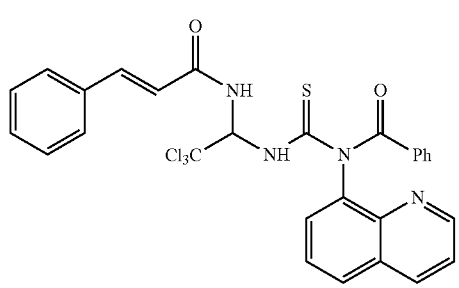 | C28H21Cl3N4O2S | 583.92 |

TABLE 2-continued

| ID | Structure | Formula | M.W. |
|---|---|---|---|
| 1910 | 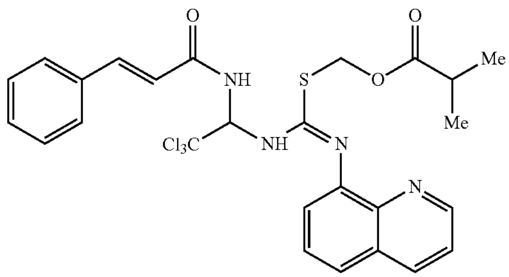 | C26H25Cl3N4O3S | 579.93 |
| 1911 | 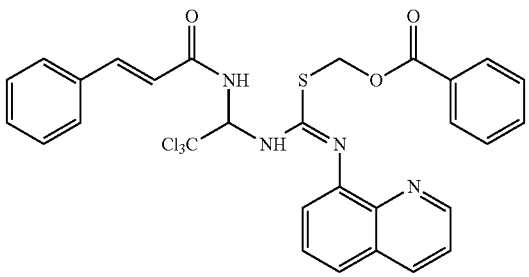 | C29H23Cl3N4O3S | 613.94 |
| 1912 | 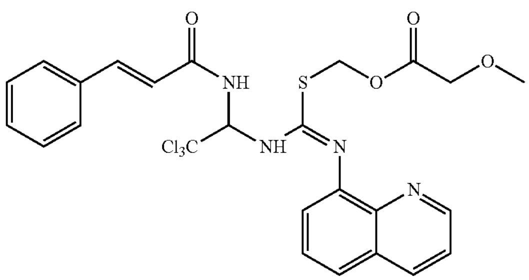 | C25H23Cl3N4O4S | 581.9 |
| 1913 | 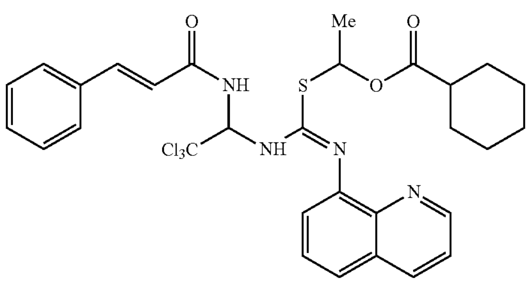 | C30H31Cl3N4O3S | 634.02 |
| 1914 | 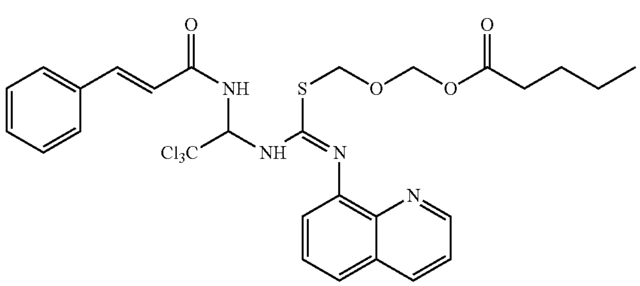 | C28H29Cl3N4O4S | 623.98 |

TABLE 2-continued

| ID | Structure | Formula | M.W. |
|---|---|---|---|
| 1915 | 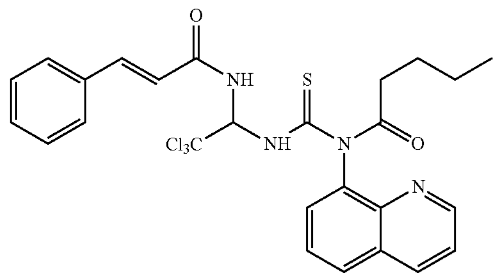 | C26H25Cl3N4O2S | 563.93 |
| 1916 | 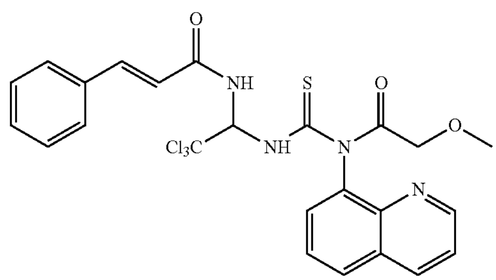 | C24H21Cl3N4O3S | 551.87 |
| 1917 | 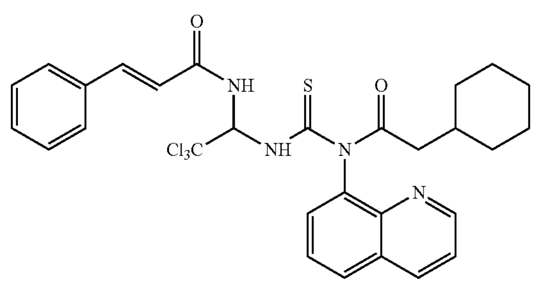 | C29H29Cl3N4O2S | 603.99 |
| 1918 | 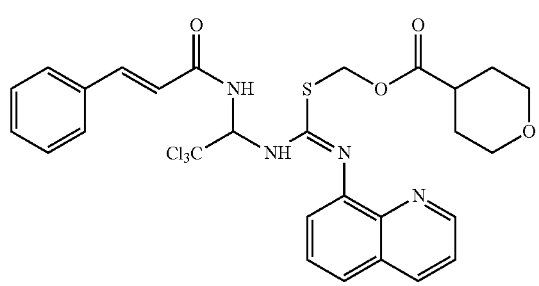 | C28H27Cl3N4O4S | 621.96 |
| 1919 | 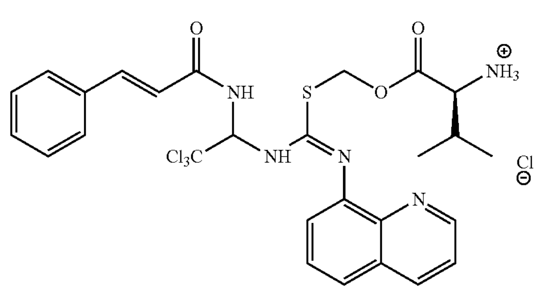 | C27H29Cl4N5O3S | 608.97 |

TABLE 2-continued
| ID | Structure | Formula | M.W. |
|---|---|---|---|
| 1920 | 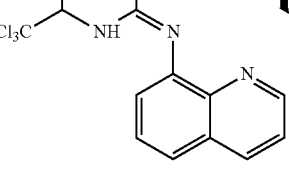 | C28H23Cl4N5O3S | 622.99 |
| 1921 | 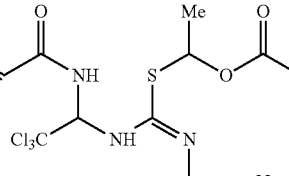 | C28H29Cl3N4O3S | 607.98 |
| 1922 | 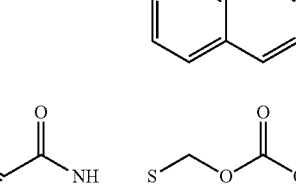 | C24H21Cl3N4O4S | 567.87 |
| 1923 | 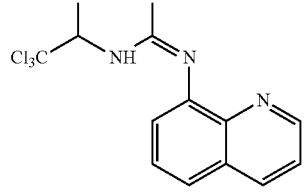 | C26H25Cl3N4O4S | 595.93 |
| 1924 | 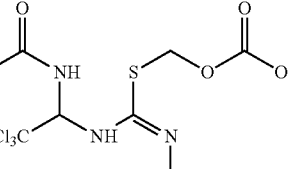 | C27H27Cl3N4O4S | 609.95 |

TABLE 2-continued

| ID | Structure | Formula | M.W. |
| --- | --- | --- | --- |
| 1925 | 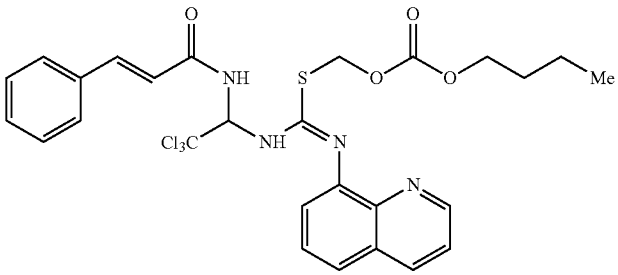 | C27H27Cl3N4O4S | 609.95 |
| 1926 | 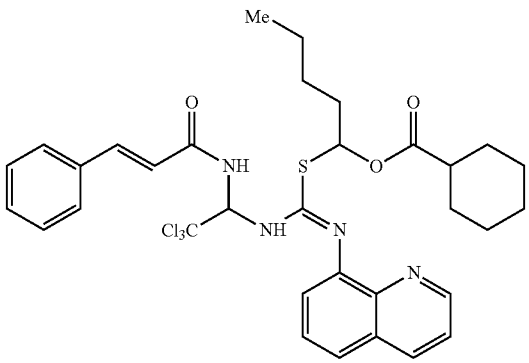 | C33H37Cl3N4O3S | 676.1 |
| 1927 | 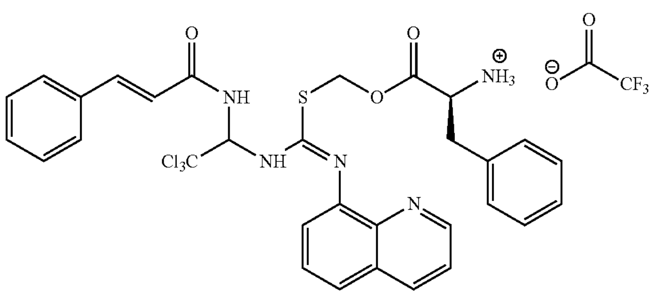 | C33H29Cl3F3N5O5S | 657.01 |
| 1928 | 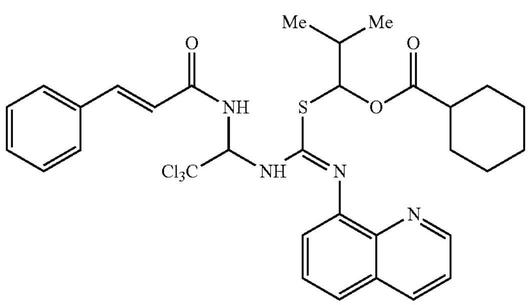 | C32H35Cl3N4O3S | 662.07 |
| 1929 | 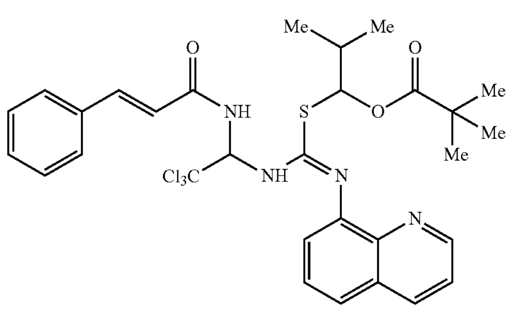 | C30H33Cl3N4O3S | 636.03 |

TABLE 2-continued

| ID | Structure | Formula | M.W. |
|---|---|---|---|
| 1930 | 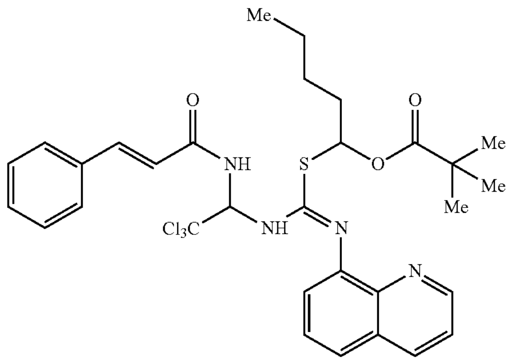 | C31H35Cl3N4O3S | 650.06 |
| 1931 | 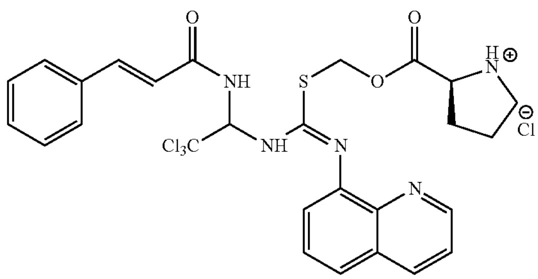 | C27H26Cl4N5O3S | 606.95 |
| 1932 | 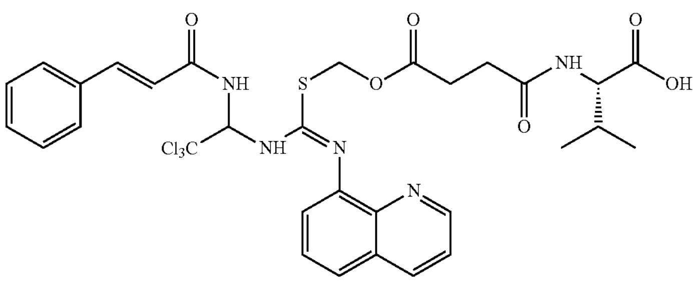 | C31H32Cl3N5O6S | 709.04 |
| 1933 | 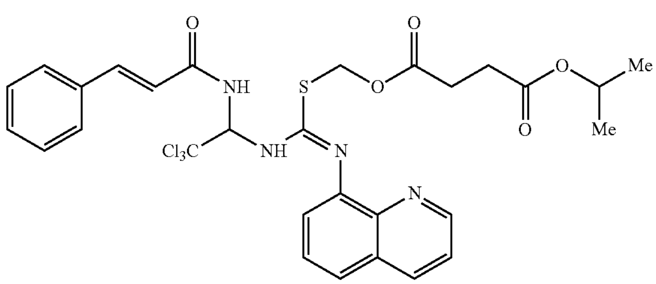 | C29H29Cl3N4O5S | 651.99 |
| 1934 | 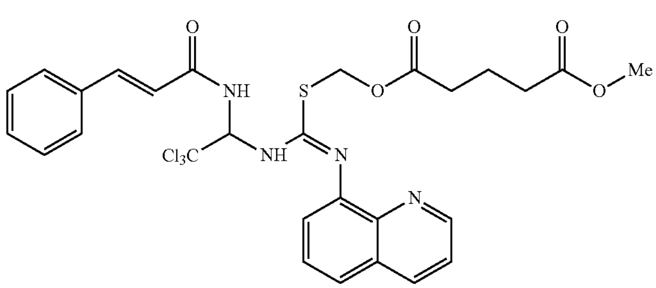 | C28H27Cl3N4O5S | 637.96 |

TABLE 2-continued

| ID | Structure | Formula | M.W. |
|---|---|---|---|
| 1935 | 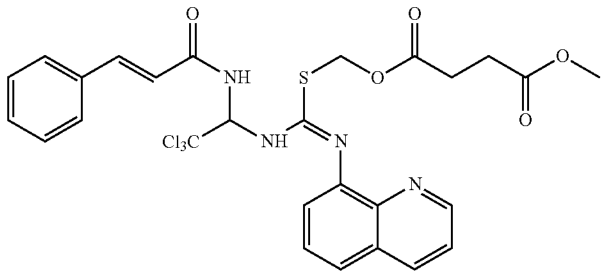 | C27H25Cl3N4O5S | 623.94 |
| 1936 | 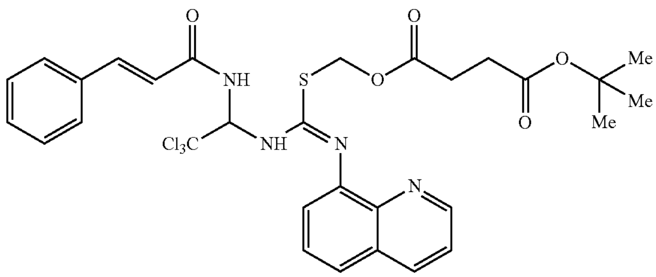 | C30H31Cl3N4O5S | 666.01 |
| 1937 | 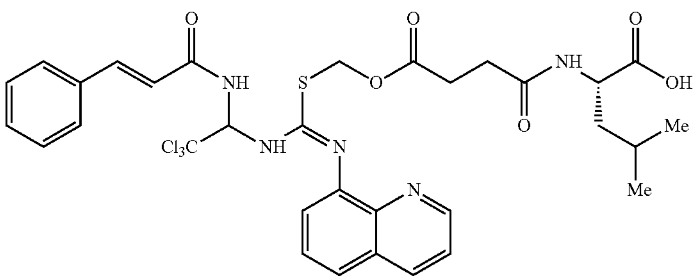 | C32H34Cl3N5O6S | 723.07 |
| 1938 | 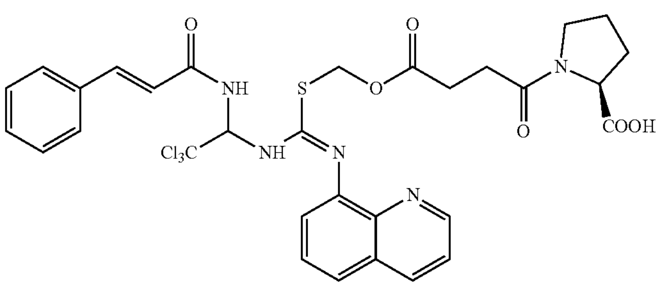 | C31H30Cl3N5O6S | 707.02 |
| 1939 | 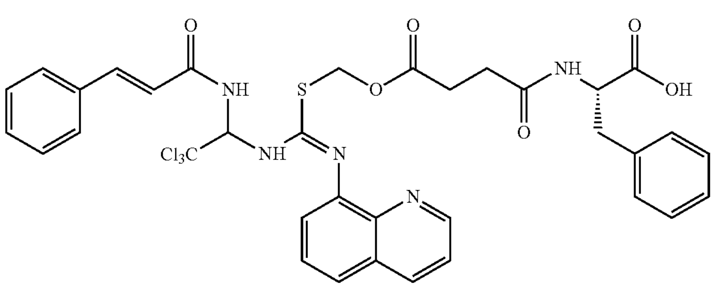 | C35H32Cl3N5O6S | 757.08 |

TABLE 2-continued

| ID | Structure | Formula | M.W. |
|----|-----------|---------|------|
| 1940 | 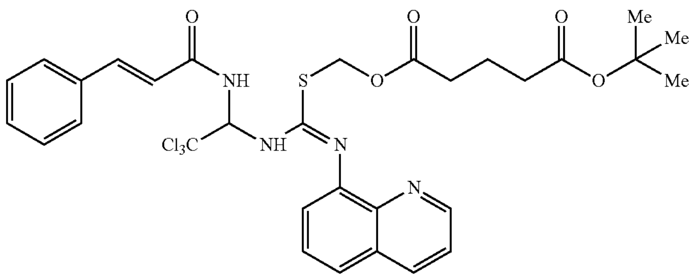 | C31H33Cl3N4O5S | 680.04 |
| 1941 | 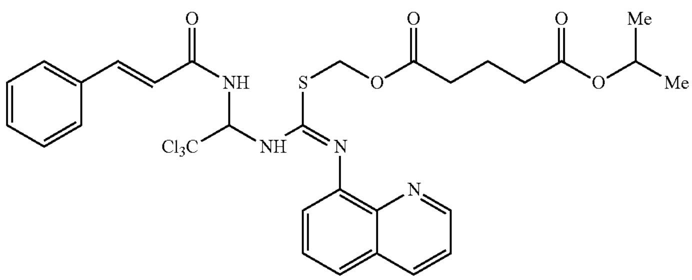 | C30H31Cl3N4O5S | 666.01 |
| 1942 | 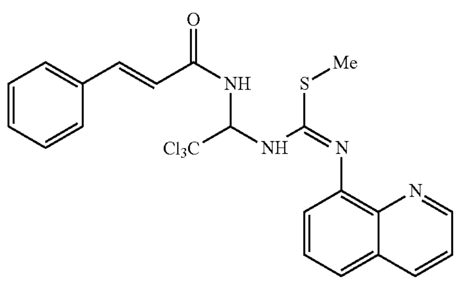 | C22H19Cl3N4OS | 493.84 |
| 1943 | 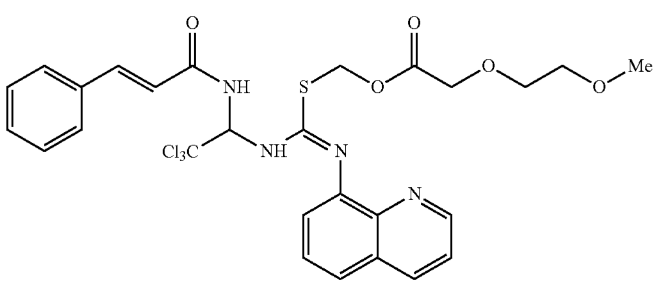 | C27H27Cl3N4O5S | 625.95 |
| 1944 | 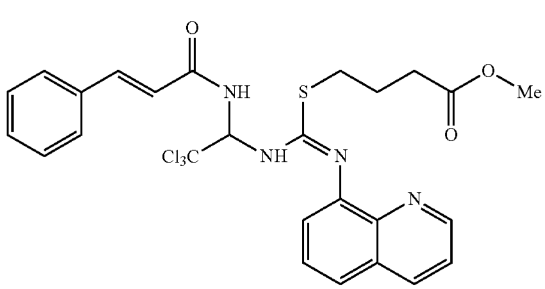 | C26H25Cl3N4O3S | 579.93 |

TABLE 2-continued

| ID | Structure | Formula | M.W. |
|---|---|---|---|
| 1945 | 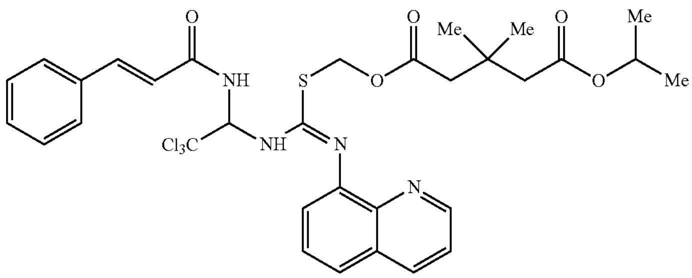 | C32H35Cl3N4O5S | 694.04 |
| 1946 | 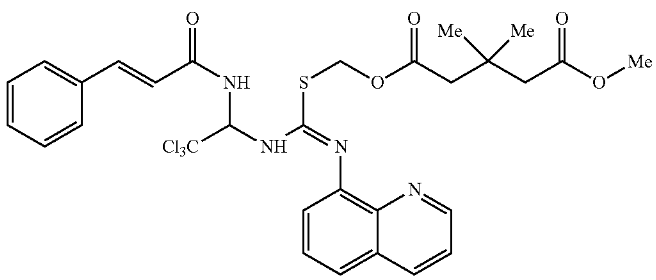 | C30H31Cl3N4O5S | 666.01 |
| 1947 | 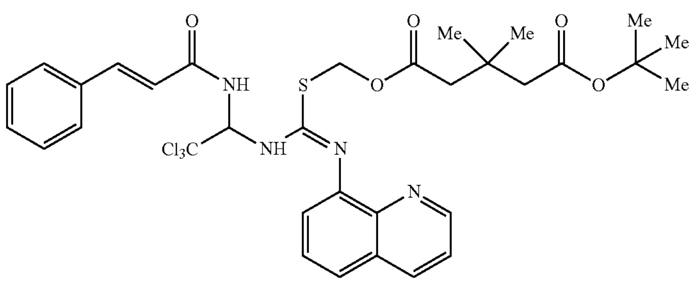 | C33H37Cl3N4O5S | 708.09 |
| 1948 | 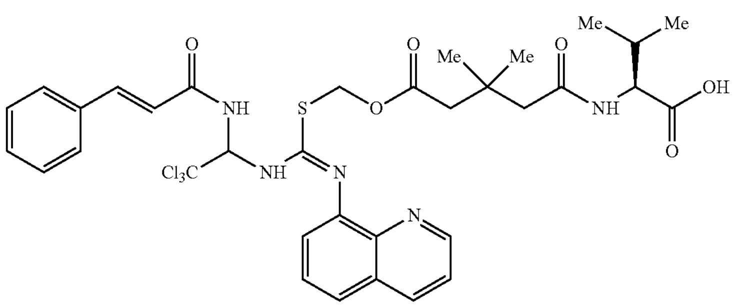 | C34H38Cl3N5O6S | 751.12 |
| 1949 | 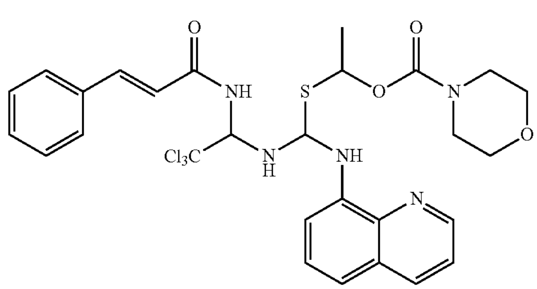 | C28H30Cl3N5O4S | 638.99 |

In one embodiment, a phosphorylation inhibitors of eIF2-alpha according to the invention has the Formula (III), as shown below,

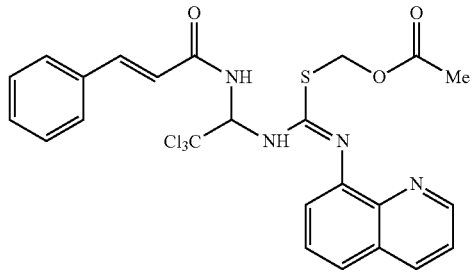

(III)

or a pharmaceutically acceptable salt, hydrate, or solvate thereof.

In one embodiment, a phosphorylation inhibitors of eIF2-alpha according to the invention has the Formula (IV), as shown below,

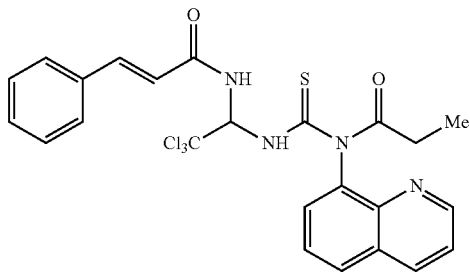

(IV)

or a pharmaceutically acceptable salt, hydrate, or solvate thereof.

In one embodiment, a phosphorylation inhibitors of eIF2-alpha according to the invention has the Formula (V), as shown below,

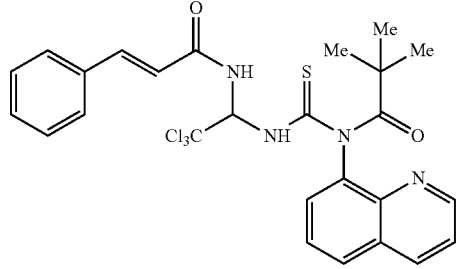

(V)

or a pharmaceutically acceptable salt, hydrate, or solvate thereof.

In one embodiment, a phosphorylation inhibitors of eIF2-alpha according to the invention has the Formula (VI), as shown below,

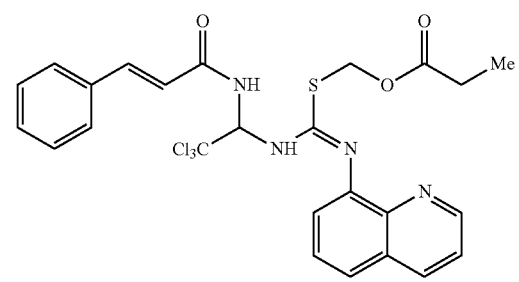

(VII)

or a pharmaceutically acceptable salt, hydrate, or solvate thereof.

In one embodiment, a phosphorylation inhibitors of eIF2-alpha according to the invention has the Formula (VII), as shown below,

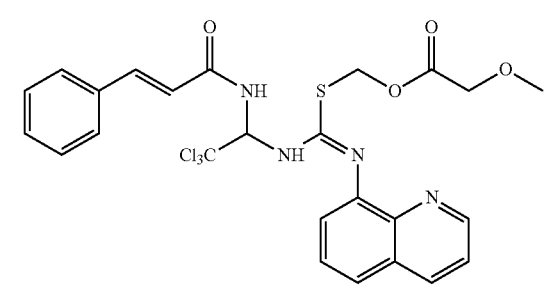

(VII)

or a pharmaceutically acceptable salt, hydrate, or solvate thereof.

In one embodiment, a phosphorylation inhibitors of eIF2-alpha according to the invention has the Formula (VIII), as shown below,

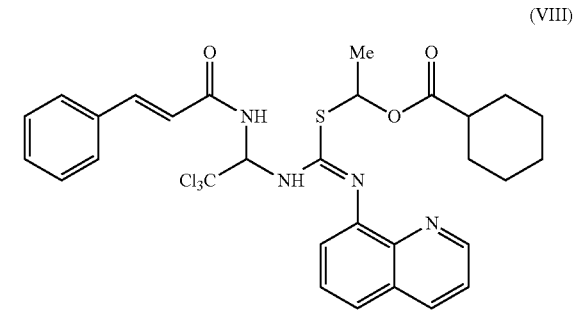

(VIII)

or a pharmaceutically acceptable salt, hydrate, or solvate thereof.

In one embodiment, a phosphorylation inhibitors of eIF2-alpha according to the invention has the Formula (IX), as shown below,

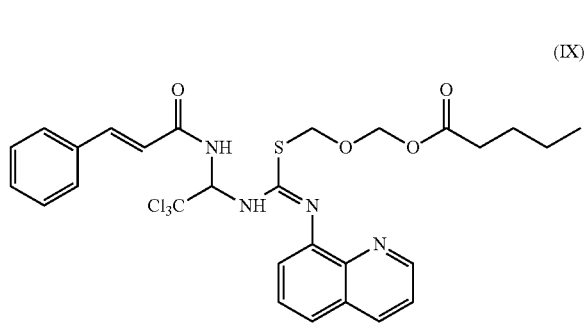

(IX)

or a pharmaceutically acceptable salt, hydrate, or solvate thereof.

In one embodiment, a phosphorylation inhibitors of eIF2-alpha according to the invention has the Formula (X), as shown below,

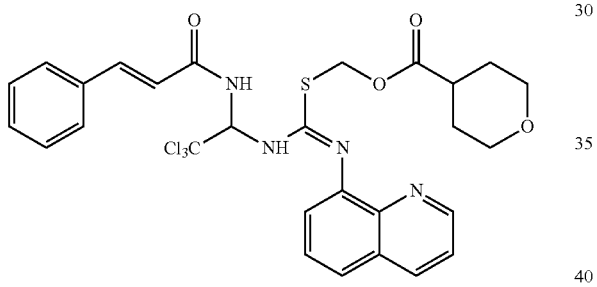

(X)

or a pharmaceutically acceptable salt, hydrate, or solvate thereof.

In one embodiment, a phosphorylation inhibitors of eIF2-alpha according to the invention has the Formula (XI), as shown below,

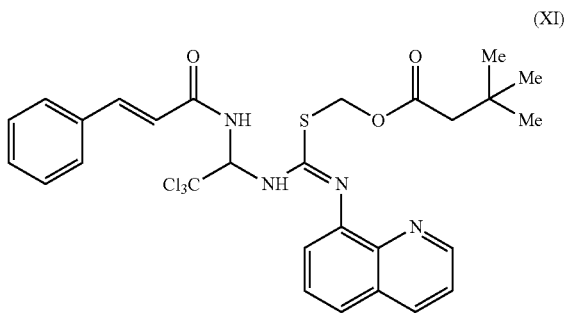

(XI)

or a pharmaceutically acceptable salt, hydrate, or solvate thereof.

In one embodiment, a phosphorylation inhibitors of eIF2-alpha according to the invention has the Formula (XII), as shown below,

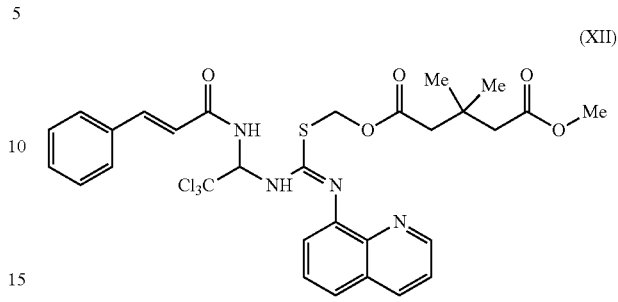

(XII)

or a pharmaceutically acceptable salt, hydrate, or solvate thereof.

In one embodiment, a phosphorylation inhibitors of eIF2-alpha according to the invention has the Formula (XIII), as shown below,

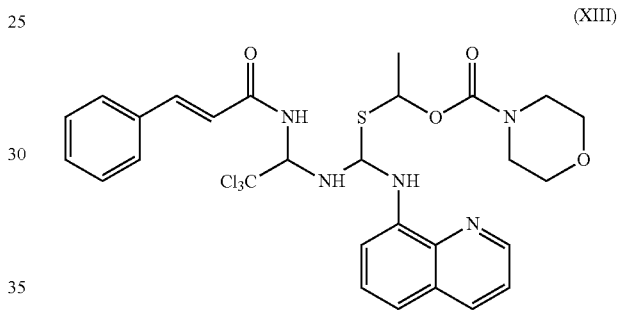

(XIII)

or a pharmaceutically acceptable salt, hydrate, or solvate thereof.

In some embodiments, groups $R^1$, $R^2$, $R^3$, $R^4$ and $R^5$ from Formula (II) correspond to sites available to link a functional group (e.g., a pro-drug group) and to generate a Salubrinal derivative. For example, without limitation, site $R^1$ can be linked to a functional group via a Michael addition/beta-elimination and sites $R^{2-5}$ can be linked to a functional group via an alkylation/regeneration through enzymatic or chemical cleavage. In another example, without limitation, site $R^3$ can be linked to a functional group by reacting a 1-chloro-amide with a nucleophile. In another example, without limitation, site $R^4$ can be linked to a functional group by reacting a thioisocyanate with a nucleophile. In another example, without limitation, site $R^4$ can be linked to a functional group by acylation of salubrinal with acylchloride. In another example, without limitation, site $R^5$ can be linked to a functional group by the alkylation of salubrinal with chloroacetals. In another example, without limitation, sites $R^3$ and $R^4$ can be linked to a functional group by using a hemi-aminal and the enzymatic cleavage of the hemi-aminal capping group.

In some embodiments, groups $R^1$, $R^2$, $R^3$, $R^4$, and $R^5$ from Formula (II) are amino acid or amino acid derivatives. The amino acid can be, for example, alanine (ala—A), arginine (arg—R), asparagine (asn—N), aspartic acid (asp—D), cysteine (cys—C), glutamine (gln—Q), glutamic acid (glu—E), glycine (gly—G), histidine (his—H), isoleucine (ile—I), leucine (leu—L), lysine (lys—K), methionine (met—M), phenylalanine (phe—F), proline (pro—P), serine (ser—S), threonine (thr—T), tryptophan (trp—W), tyrosine (tyr—Y), valine (val—V), or any combinations thereof.

A "derivative" or "analog" is defined as a eIF2-alpha phosphorylation inhibitor that has been subjected to chemical modification. Derivatization may include the substitution of certain chemical groups to Salubrinal. Such derivatizations are known from the state of the art. The derivatives and analogs maintain the biological activity of Salubrinal and function in a similar manner, but can offer advantages to the compound, such as a longer life, resistance to decomposition or increased activity. The term "analog" encompasses derivatives of salubrinal as well as chemically synthesized molecules sharing certain chemical similarities to salubrinal.

It should be understood that a reference to a salt includes the solvent addition forms or crystal forms thereof, particularly solvates or polymorphs. Solvates contain either stoichiometric or non-stoichiometric amounts of a solvent, and are often formed during the process of crystallization with pharmaceutically acceptable solvents such as water, ethanol, and the like. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate. Compounds described herein are optionally in various forms, including but not limited to, amorphous forms, milled forms and nano-particulate forms. In addition, compounds described herein include crystalline forms, also known as polymorphs. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate. The compounds described herein may be in crystalline or amorphous form, and may be in the form of a hydrate or a solvate. Several polymorphs of the crystalline form can be formulated and are also encompassed within the invention.

EXAMPLES

Aspects of the applicant's teachings may be further understood in light of the following examples, which should not be construed as limiting the scope of the applicant's teachings in any way or by necessarily indicative to the optimal ways that the invention can be practice.

Synthesis of Salubrinal Analog—Compound ID 1912

By way of example, a description of the synthesis for compound ID 1912 is presented in FIG. 1. The sequence of the synthesis consists of 7 distinct chemical product structures and involves chromatography. Compound ID 1912 was produced with a purity of 98.2% in 7 steps with an overall yield of 13% from cinnamamide as the starting material. All oxygen and/or moisture sensitive reactions were carried out under $N_2$ atmosphere. All reagents and solvents were purchases from commercial vendors and used as received. 1H NMR spectra were recorded on a 500 MHz spectrometer. HPLC conditions for all LCMS on Waters Alliance 2695 reported: Waters XTerra RP18 34.6×30 mm, 3.5 μm; hold 5% B for 0.2 minute, 5% to 100% B in 1.8 minutes, then hold 100% B for 1.0 minute, run time=3.0 min; Eluents: A 10 mM NH4COOH in water; B=MeCN.

Step 1.

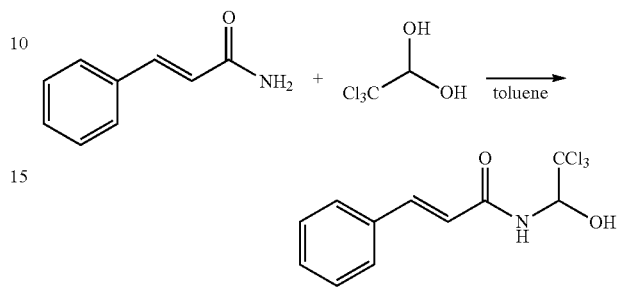

Cinnamamide and chloral hydrate were dissolved in toluene; the mixture was heated to 120° C. The RBF was left open for 20 min, to allow water and toluene co-evaporates. The condenser was applied and the reaction was stirred for 36 hrs. The mixture was concentrated, and the residue was dissolved in 50 mL EtOAc, and reflux for 2 hrs, the cool the mixture to room temperature, and filter, yielding 3.9052 g white crystal. 1H NMR: (500 MHz, CDCl3) δ 7.68 (d, J=15.6 Hz, 1H), 7.49-7.43 (m, 2H), 7.35-7.29 (m, 3H), 6.38 (d, J=15.6 Hz, 1H), 6.27 (d, J=8.8 Hz, 1H), 6.02 (dd, J=9.1, 5.1 Hz, 1H), 3.87 (s, 1H).

Step 2.

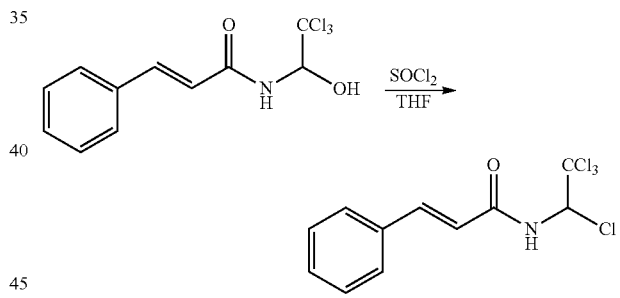

Alcohol was dissolved in 40 mL dry THF. To this solution, 4 mL SOCl2 was added, after the addition, the mixture was heated to 60° C. for 3 hrs. Then the solvent and excess SOCl2 was rotavapped, the residue was used as crude for the next step.

Step 3.

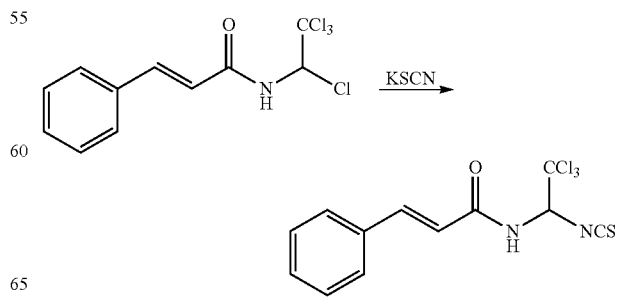

Crude residue from reaction 229-17 was dissolved in acetone, and to the solution was added 2.7 g KSCN. The mixture was stirred at reflux for 2 hrs. After cooling down to room temperature, the mixture was filtered to remove inorganic salt. Then the filtrate was concentrated, and EtOAc was added to precipitate the inorganic by-product, and the slurry was filtered again. Concentrated the filtrate, purified the residue by ISCO, 20-30% EtOAc/Hexane, 10% EtOAc/Hexane to load the solid, yielding light yellow solid 3.61 g.
Step 4.

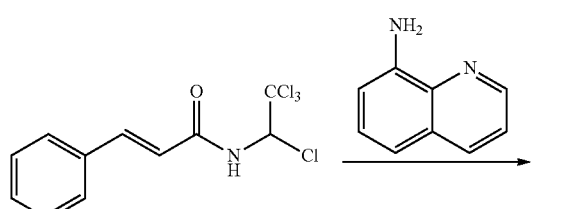

Isothiocynate and quinoline were dissolved in THF and heated up at 60° C. for 1 h. Then solvent was evaporated, and 50 mL DCM was added to precipitate the product. The slurry was filtered, yielding 4.8328 g gray product.
Step 5.

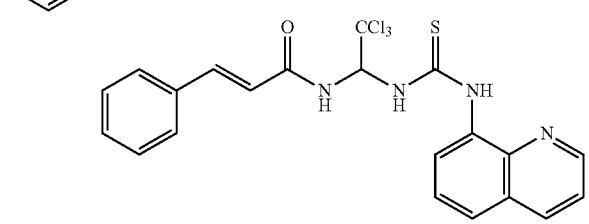

Add acyl chloride and paraformaldehyde to dry ZnCl2 in dry RBF. The reaction is stirred at 110° C. for 1.5 h and then diluted by water and extracted by Et2O. The combined organic layers were dried and concentrated. The resulting residue was distilled, and the product comes out at around 40-50° C. (normal pump, the pressure is not clear), yielding 0.92 g clear liquid. 1H NMR: (500 MHz, CDCl3) δ 5.79 (s, 2H), 4.13 (s, 2H), 3.50 (s, 3H).
Step 6.

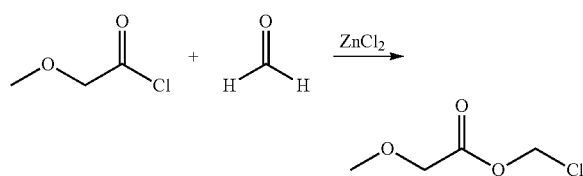

Chloride was dissolved in 8 mL acetone, and to the solution was added NaI. The reaction was stirred at room temperature for 2 hrs. Acetone was removed by rotavap, and 5 mL DCM was added to crash out the inorganic salt, and then filtered the mixture. The filtrate was rotavaped to remove DCM, the crude iodide was used in next step as crude.

Step 7.

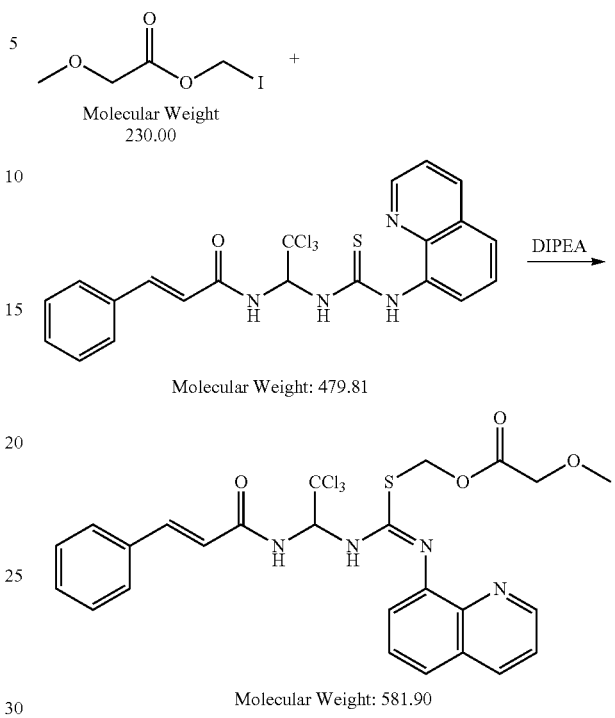

Salubrinal was suspended in 40 mL ACN (more dilute than 229-45). To the mixture was added DIPEA and iodide. The reaction was stirred at Room temperature. LCMS showed 29% product. The mixture was filtered to recover salubrinal, washed with ACN. The filtrate was concentrated and purified by reverse-combiflash (20% ACN/water 5 min, 20-55% ACN/water 5 min, 55-75% 15 min, the compound came out at 66%). The collected solution was concentrated and lyoed, yield 263.2 mg white product, 98.2% pure. 1H NMR: (500 MHz, DMSO) δ 9.74 (s, 1H), 9.05 (d, J=8.7 Hz, 1H), 8.95-8.91 (m, 2H), 8.45 (dd, J=8.3, 1.6 Hz, 1H), 7.70-7.64 (m, 2H), 7.61-7.55 (m, 4H), 7.46-7.38 (m, 3H), 6.88 (d, J=15.8 Hz, 1H), 6.34 (d, J=8.8 Hz, 1H), 5.85-5.74 (m, 2H), 4.36-4.24 (m, 2H), 3.35 (s, 3H).

Synthesis of Salubrinal Analog—Compound ID 1913

Figure 2:
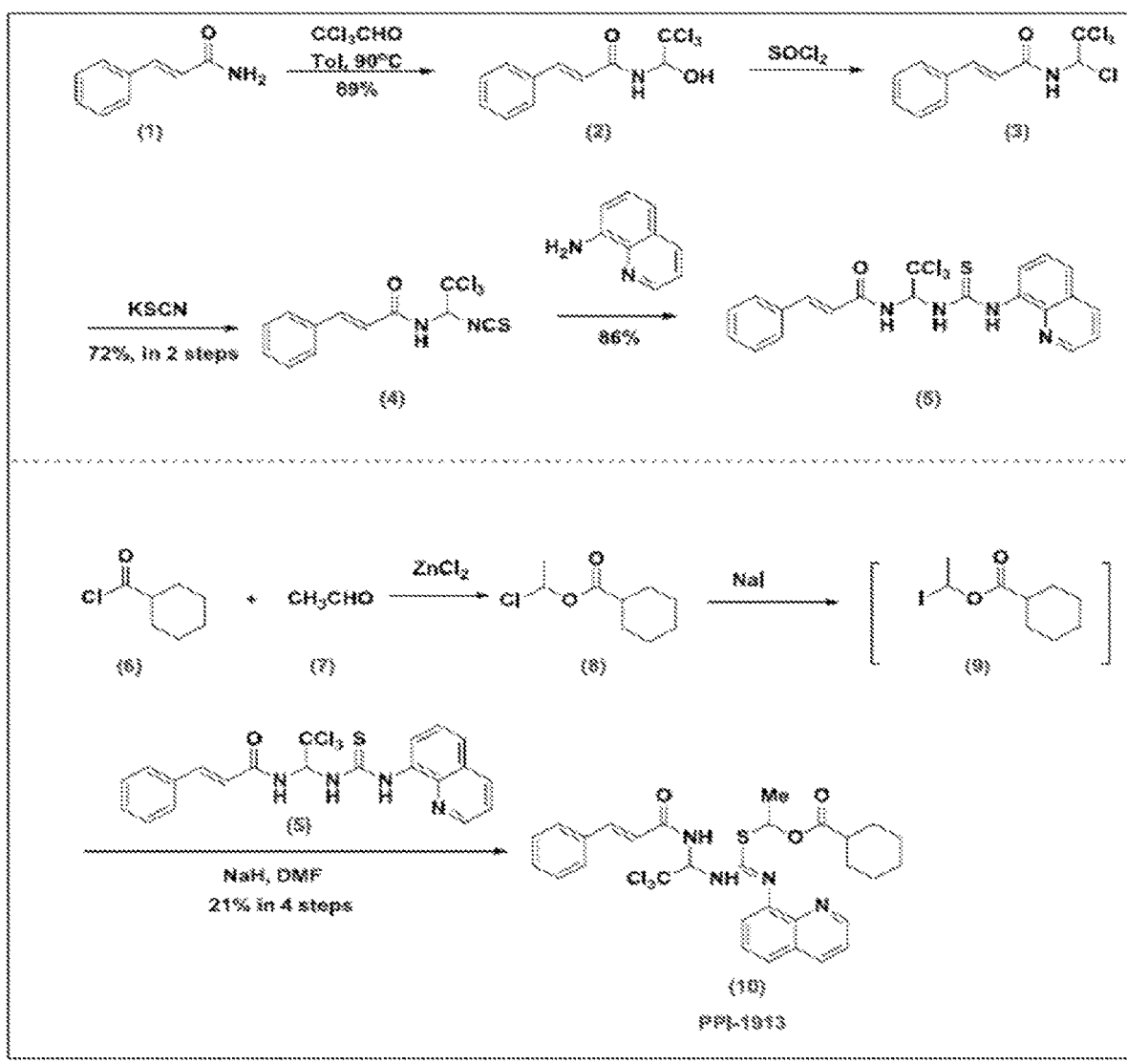
FIG. 2 is a diagram showing the synthesis of compound ID 1913.

By way of example, a description of the synthesis for compound ID 1913 is presented in FIG. 2. The sequence of the synthesis consists of 7 distinct chemical product structures and involves chromatography. Compound ID 1913 was produced with a purity >99% in 7 steps with an overall yield of 12% from cinnamamide as the starting material. All oxygen and/or moisture sensitive reactions were carried out under N2 atmosphere. All reagents and solvents were purchases from commercial vendors and used as received. 1H NMR spectra were recorded on a 500 MHz spectrometer. HPLC conditions for all LCMS on Waters Alliance 2695 reported: Waters XTerra RP18 34.6×30 mm, 3.5 μm; hold 5% B for 0.2 minute, 5% to 100% B in 1.8 minutes, then hold 100% B for 1.0 minute, run time=3.0 min; Eluents: A 10 mM NH4COOH in water; B=MeCN.

Step 1.

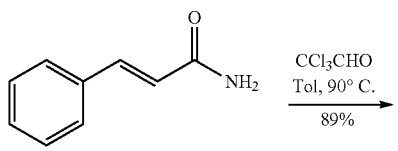

Chemical Formula: C₉H₉NO
Molecular Weight: 147.17
(1)

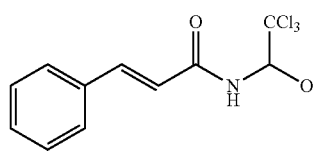

Chemical Formula: C₁₁H₁₀Cl₂NO₂
Molecular Weight: 294.56
(2)

Compound 1 (3.0 g, 20.4 mmol) and chloral hydrate (4.7 g, 28.5 mmol) were dissolved in toluene (150 mL) and the mixture was stirred at 120° C. overnight. The reaction was then concentrated in vacuum. T o the mixture was added EtOAc (50 mL) and refluxed for another 2 hours. Filter the precipitate and obtained compound 2 (5.3 g, 89% in yield).

StepS 2-3.

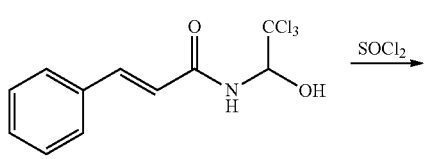

Chemical Formula: C₁₁H₁₀Cl₃NO₂
Molecular Weight: 294.56
(2)

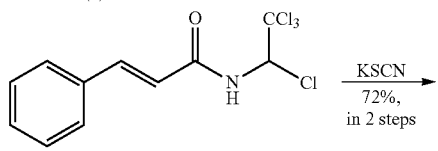

Chemical Formula: C₁₁H₁₀Cl₄NO
Molecular Weight: 313.01
(3)

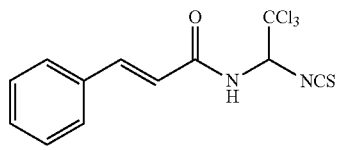

Chemical Formula: C₁₂H₉Cl₃N₂OS
Molecular Weight: 335.64
(4)

To a solution of compound 2 (5.3 g, 18.0 mmol) in THF (50 mL, dry) were added thionyl chloride (5.0 mL, 68.9 mmol). The resulting reaction mixture was stirred at 60° C. for 3 hrs under nitrogen atmosphere. The reaction mixture was concentrated in vacuum to give crude compound 3 which was dissolved in acetone (50 mL). To the mixture was added KSCN (3.5 g, 36.1 mmol). The resulting reaction mixture was refluxed for 2 hours and cooled to room temperature. Precipitate was filtered off and the filtrate was concentrated in vacuum. Dilute the crude was EtOAc (30 mL) and filter off the precipitate again. The filtrate was concentrated in vacuo and compound 4 (4.3 g, 72%) was obtained after flash column chromatography (0% EtOAc in hexanes to 50% EtOAc in hexanes).

Step 4.

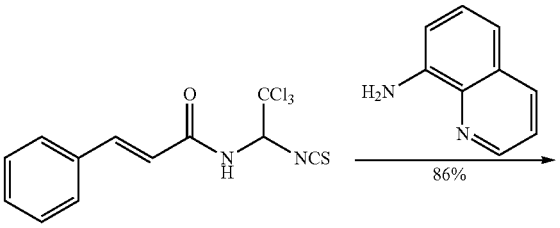

Chemical Formula: C₁₂H₉Cl₃N₂OS
Molecular Weight: 335.64
(4)

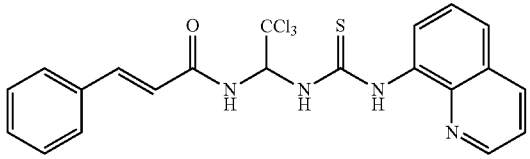

Chemical Formula: C₂₃H₁₇Cl₃N₄OS
Molecular Weight: 479.81
(5)

To THF (50 mL) was added compound 4 (4.3 g, 12.8 mmol) and 8-aminoquinoline sequentially. The mixture was stirred at 60° C. for 1 h. The solvent was removed in vacuUM and to the mixture as added DCM (50 mL) and stirred for 10 min. Filter the precipitate and Compound 5 (5.3 g, 86% in yield) was obtained.

Step 5.

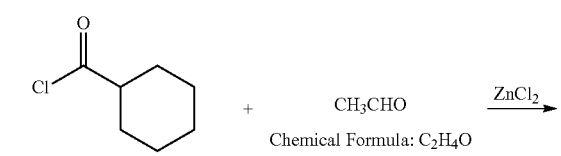

Chemical Formula: C₇H₁₁ClO
Molecular Weight: 146.61
(6)

Chemical Formula: C₂H₄O
Molecular Weight: 44.95
(7)

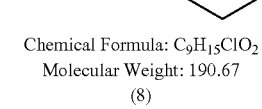

Chemical Formula: C₉H₁₅ClO₂
Molecular Weight: 190.67
(8)

Compound 6 (3.6 mL, 24.5 mmol) was dissolved in DCM (50 mL) and the mixture was cooled to 0° C. under N2 protection. To the mixture was added zinc chloride (0.4 g, 2.4 mol, anhydrous) followed by compound 7 (2.4 mL, 37.0 mmol). The reaction is stirred at room temperature for 4 hours and concentrated. The crude was diluted with Et2O/water (30 mL/30 mL). The organic layer was separated, dried over Na2SO4 and concentrated. Compound 8 (1.5 g, 29% in yield) was obtained after vacuum distillation.
StepS 6-7.

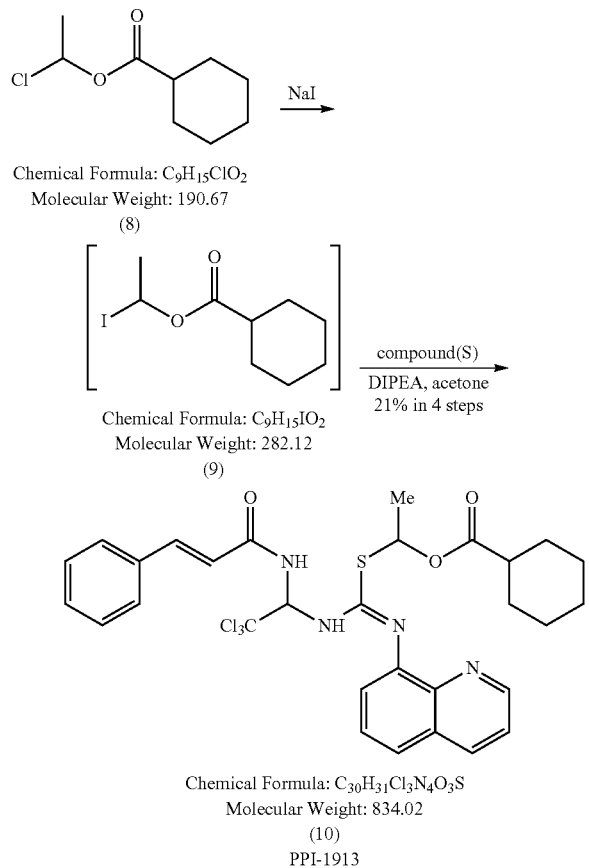

Compound 8 (800 mg, 4.2 mmol) was dissolved in acetone (10 mL) and to the solution was added NaI (784 mg, 5.2 mmol). The reaction is stirred at room temperature for 2 hours and the solvent in removed in vacuum. Then DCM (20 mL) was added and the precipitate was filtered off. The filtrate was concentrated in vacuo to give crude compound 9. Compound 9 was added to a pre-stirred solution of compound 5 (1.0 g, 2.1 mmol) and DIPEA (809 mg, 5.2 mmol) in MeCN (20 mL). The reaction mixture is stirred at 60° C. for 16 hours. The solvent was removed in vacuo and compound 10 (276 mg, 21% in yield) was obtained after flash column chromatography (two purification is required, 1st purification is normal phase with silica column, from 0% EtOAc in hexanes to 30% EtOAc in hexanes. 2nd purification is C18 column, from 50% MeCN in 10 mM AmF in water to 100% MeCN).

LC/MS/MS Characterization of Salubrinal Analogs

A description of the characterization of compound IDs 1901-1948 is presented in FIG. 3. Samples were analyzed by LC/MS/MS using a CTC PAL autosampler, Shimadzu Prominence HPLC and an AB SCIEX API 4000 QTRAP triple quadrupole mass spectrometer. The [M+H]+ adducts of the prodrugs, controls and internal standards were monitored using positive mode electrospray ionization in MRM (multiple reaction monitoring) mode. The analytes were injected onto a C18 column (HyPURITY 50×2.1 mm, 3µ) and chromatographed using a reverse phase gradient with 0.1% formic acid in water and 0.1% formic acid in acetonitrile mobile phases.

Stability of Salubrinal Analogs in Phosphate Buffer and Mouse Plasma

A description of the stability of compound IDs 1901-1931 in phosphate buffer and mouse plasma is presented in FIG. 4A. A description of the stability of compound IDs 1932-1948 in phosphate buffer and mouse plasma is presented in FIG. 4B. A description of the stability of two reference compounds, i.e., salubrinal and diltiazem, in phosphate buffer and mouse plasma is presented in FIG. 4C.

The test articles for the mouse plasma stability test were incubated in duplicate in mouse plasma at 370° C. for 60 minutes. Non-enzymatic degradation of the prodrug was assessed in parallel incubations (duplicates) in 100 mM potassium phosphate buffer (pH 7.4). At the end of the incubation period, reactions were stopped by the addition of 4 volumes of ice-cold stop solution (1 µM glyburide in acetonitrile) into each assay tube. Tubes were mixed thoroughly and centrifuged to remove precipitated proteins. Resulting supernatants were collected (100 µL) and diluted (1:1) with LC/MS/MS mobile phase. The samples were analyzed by LC/MS/MS to determine the remaining parent and appearing drug (salubrinal).

Initial concentration of each prodrug in plasma and phosphate buffer was determined in a separated well. Prodrug was added to premixed matrix and stop solution and processed as described above. Data are reported as mean % of parent (or prodrug) loss and % of total salubrinal (or drug) appearance.

The experimental conditions for the mouse plasma stability test were the following:

TABLE 3

Mouse Plasma Stability Experimental Conditions

Test Conc.
1 µM
Matrices
100 mM Phosphate buffer, pH 7.4 and female CD1 mice plasma
Incubation
60 minutes at 37° C.
Reference Compounds
Salubrinal and Diltiazem For the compounds salubrinal and diltiazem, the results were assessed in duplicate as reference compounds.

Stability of Salubrinal Analogs in Mouse Liver Microsomes

A description of the stability of compound IDs 1901-1931 in mouse liver microsomes is presented in FIG. 5A. A description of the stability of compound IDs 1932-1948 in mouse liver microsomes is presented in FIG. 5B. A description of the stability of three reference compounds, i.e., salubrinal, verapamit, and diltiazem, in mouse liver microsomes is presented in FIG. 5C.

The article for the mouse liver microsomes stability test was incubated in duplicate with microsomes at 370° C. for 0 and 45 minutes. The reaction contained mouse liver microsomal protein (0.5 mg/mL) in 100 mM potassium phosphate buffer with 1 mM NADPH at pH 7.4. Control incubations (duplicates) were run for each test compound omitting NADPH to detect NADPH-free degradation. At the indicated time points, an aliquot (40 uL) was removed from each experimental and control reaction and mixed 1:4 with ice-cold stop solution (1 µM labetalol in acetonitrile). The samples were centrifuged to remove precipitated protein, and the supernatants were further diluted with 1 volume of LC/MS/MS mobile phase. The samples were analyzed by LC/MS/MS to determine the remaining parent. Data are reported as mean % of parent loss.

The experimental conditions for the mouse liver microsomal stability test was the following:

TABLE 4

Mouse Liver Microsomal Stability Experimental Conditions

Test Conc.
1 µM
Matrices
100 mM Phosphate buffer, pH 7.4 and female CD1 mouse LC
Protein Concentration
0.5 mg/mL
Incubation
45 minutes at 37° C.
Reference Compounds
Diphenhydramine, Verapamil and Salubrinal For the compounds salubrinal, verapamil, and diphenhydramine, the results were assessed in duplicate as reference compounds.

Effect of Salubrinal Analogs on Cell Viability

Figures 6A, 6B:
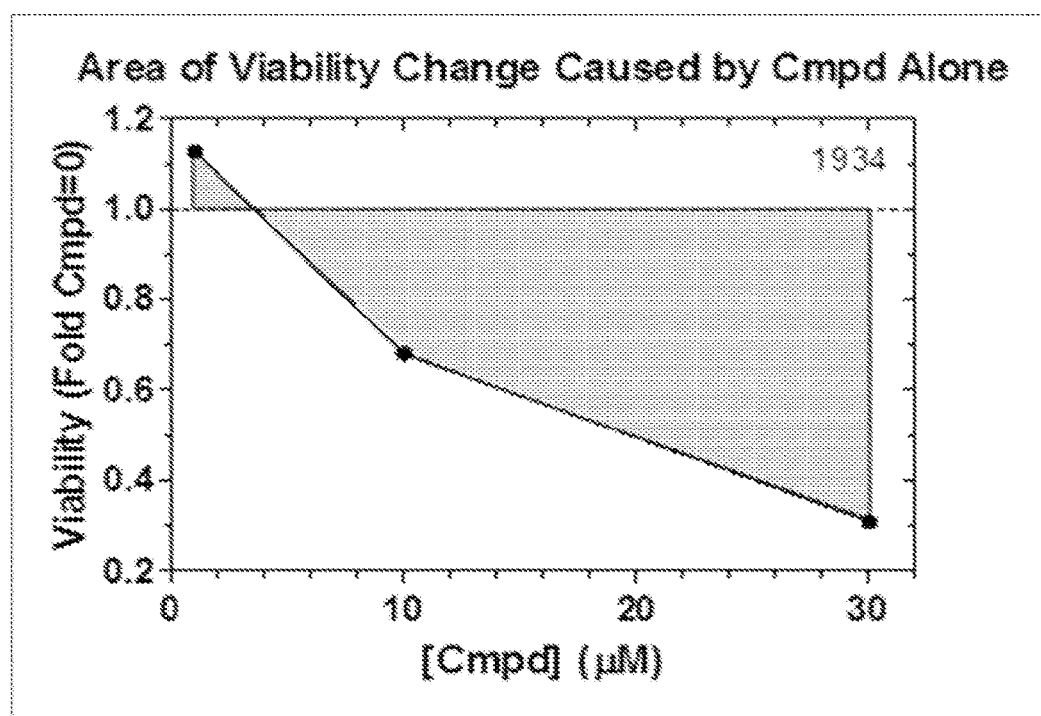
FIG. 6A is a table showing the cell viability in the absence of tunicamycin for compound ID 1934 at 0 µM, 1 µM, 10 µM, and 30 µM doses.
FIG. 6B is a drawing showing the area of cell viability change in the absence of tunicamycin for compound ID 1934.

A description of the cell viability in the absence of tunicamycin for compound ID 1934 is presented in FIG. 6A. The dose of the compound ID 1934 is varied between 0 µM and 30 µM, for each dose the test is done in triplicate, the mean viability is reported, the relative viability is reported, and area change is reported, and the total area change is reported. The area change can be plotted by compound dose, or summed over all tested doses, to compare compounds.

A description of the cell viability in function of the concentration of compound ID 1934 in the absence of tunicamycin is presented in FIG. 6B. The area of the curve is highlighted in gray.

Figure 7:
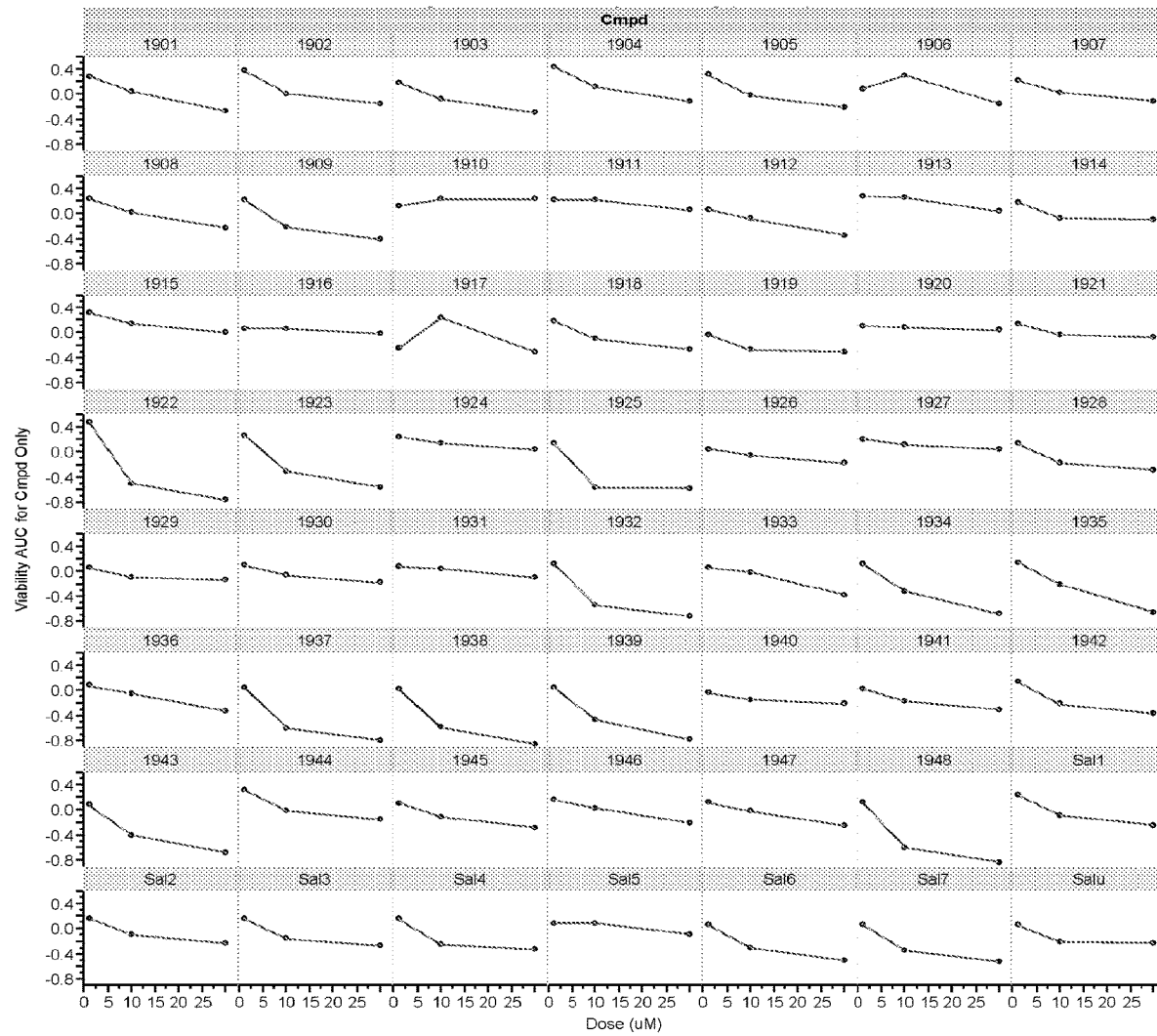
FIG. 7 is a drawing showing the cell viability area in the absence of tunicamycin for compound IDs 1901-1948 and salubrinal controls Sal 1-7 and Salu.

A description of the cell viability area in function of the concentration of compound IDs 1901-1948 and salubrinal controls Sal 1-7 and Salu in the absence of tunicamycin is presented in FIG. 7. The dose of the compounds and standards are varied between 0 µM and 30 µM.

Figure 8:
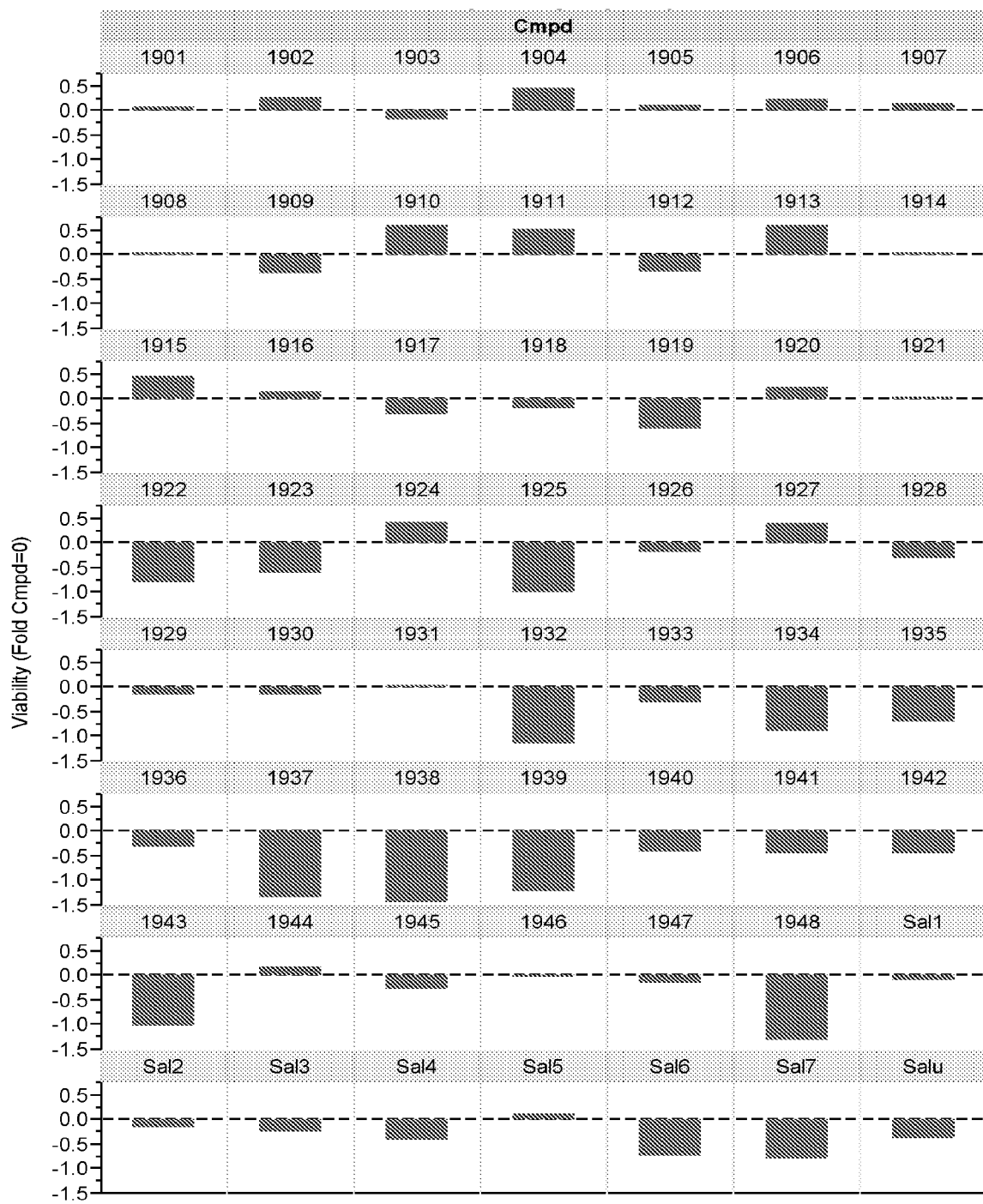
FIG. 8 is a drawing showing the total cell viability area change in the absence of tunicamycin for compound IDs 1901-1948 and salubrinal controls Sal 1-7 and Salu.

A description of the total cell viability area change for compound IDs 1901-1948 and salubrinal controls Sal 1-7 and Salu in the absence of tunicamycin is presented in FIG. 8.

Figures 9A, 9B:
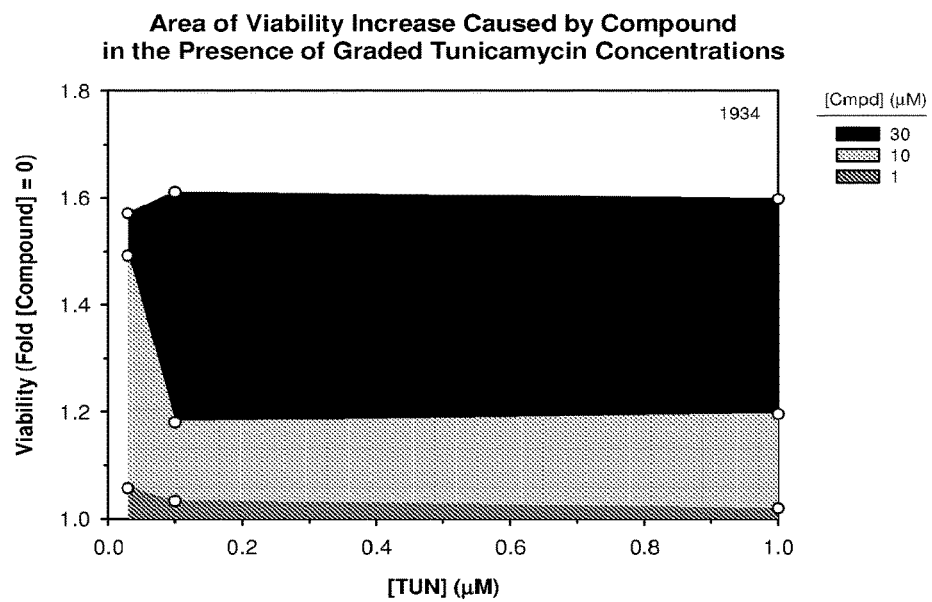
FIG. 9A is a table showing the cell viability in the presence of tunicamycin for compound ID 1934 at 0 µM, 1 µM, 10 µM, and 30 µM doses.
FIG. 9B is a drawing showing the area of cell viability change in the presence of tunicamycin for compound ID 1934.

A description of the cell viability in the presence of tunicamycin for compound ID 1934 is presented in FIG. 9A. The dose of the compound ID 1934 is varied between 0 µM and 30 µM, the dose of the tunicamycin (TUN) is varied between 0 µM and 1 µM, for each dose the test is done in triplicate, the mean viability is reported, the relative viability is reported, and area change is reported, and the total area change is reported. The area change can be plotted by compound dose, or summed over all tested doses, to compare compounds.

A description of the cell viability in function of the concentration of compound ID 1934 in the presence of tunicamycin is presented in FIG. 9B. The area of the curve for each concentration of the compound is highlighted in gray or black.

Figure 10:
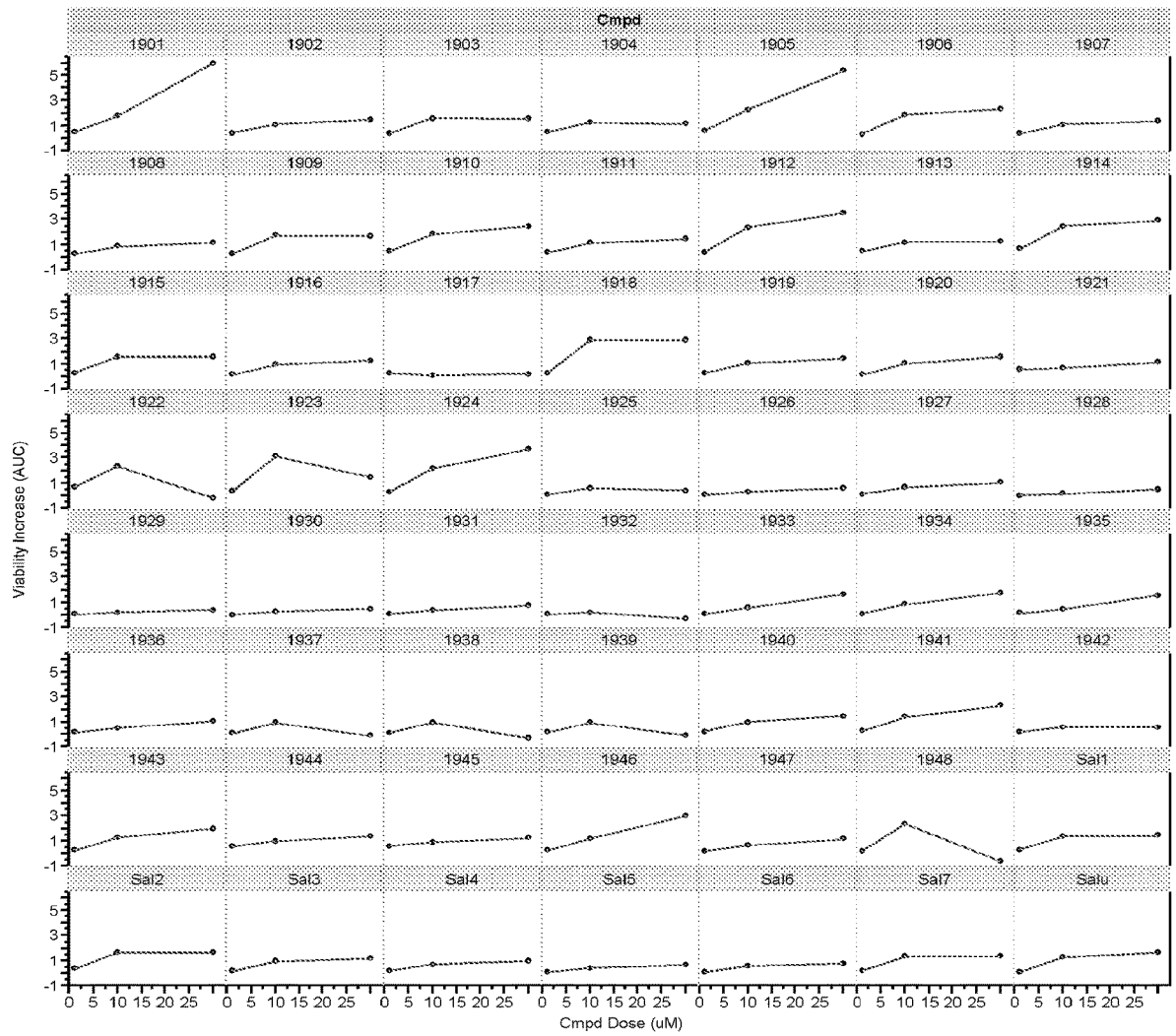
FIG. 10 is a drawing showing the cell viability area in the presence of tunicamycin for compound IDs 1901-1948 and salubrinal controls Sal 1-7 and Salu.

A description of the cell viability area in the presence of tunicamycin for compound IDs 1901-1948 and salubrinal controls Sal 1-7 and Salu is presented in FIG. 10. The dose of the compounds and control samples are varied between 0 µM and 30 µM.

Figure 11:
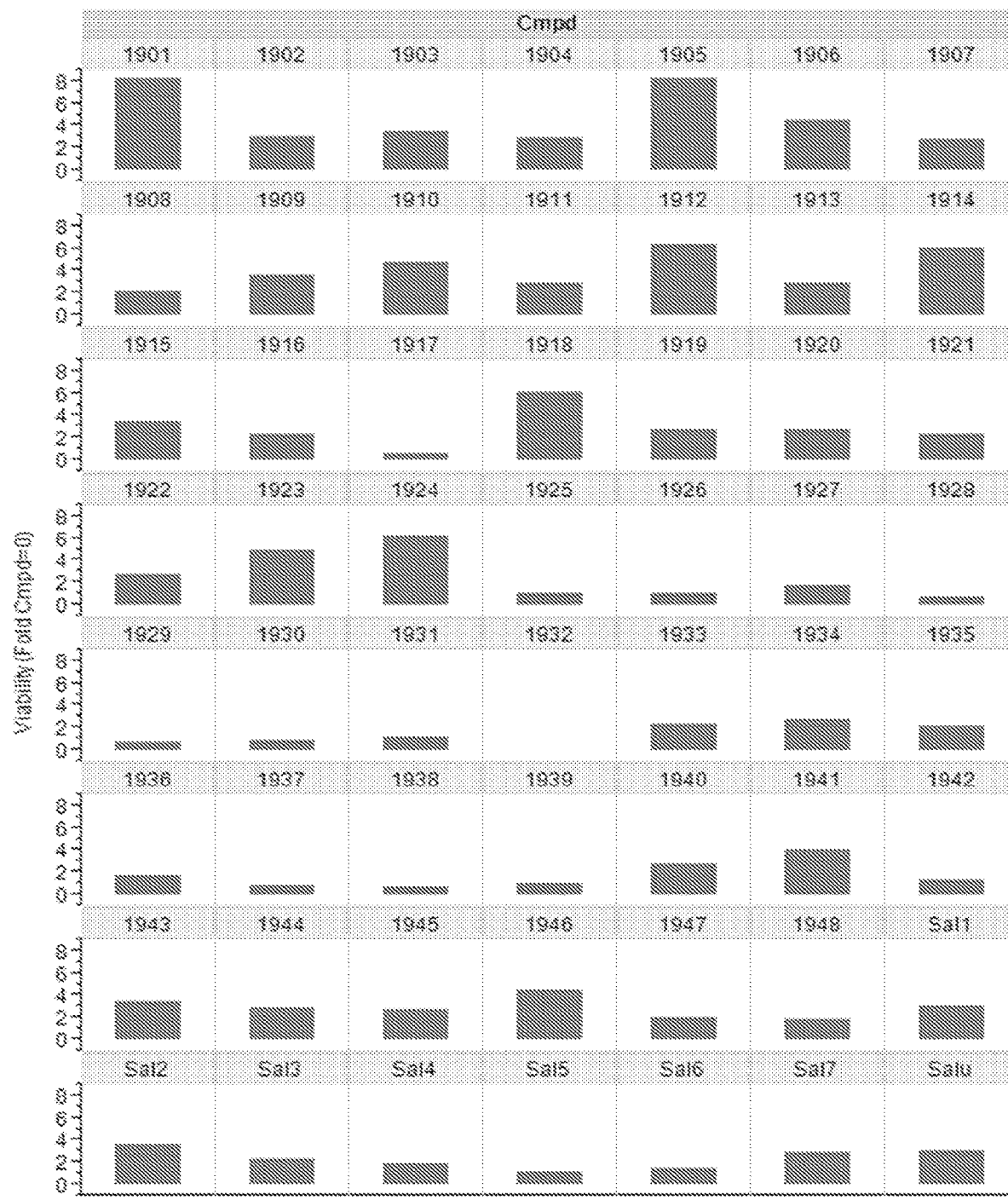
FIG. 11 is a drawing showing the total cell viability area change in the presence of tunicamycin for compound IDs 1901-1948 and salubrinal controls Sal 1-7 and Salu.

A description of the total cell viability area change in the presence of tunicamycin for compound IDs 1901-1948 and salubrinal controls Sal 1-7 and Salu is presented in FIG. 11.

Figure 12:
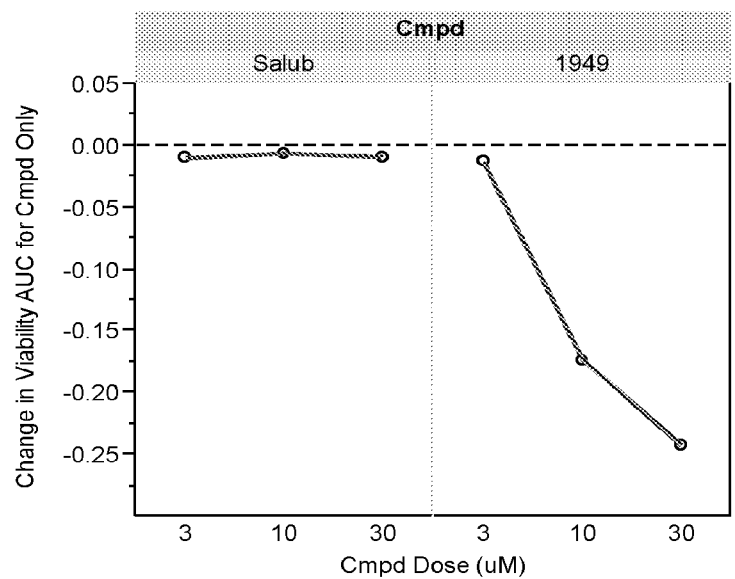
FIG. 12 is a drawing showing the dose-related change in cell viability area in the absence of tunicamycin for compound ID 1949 and salubrinal control Salub.

A description of the cell viability area in the absence of tunicamycin for compound ID 1949 and salubrinal control Salub is presented in FIG. 12.

Figure 13:
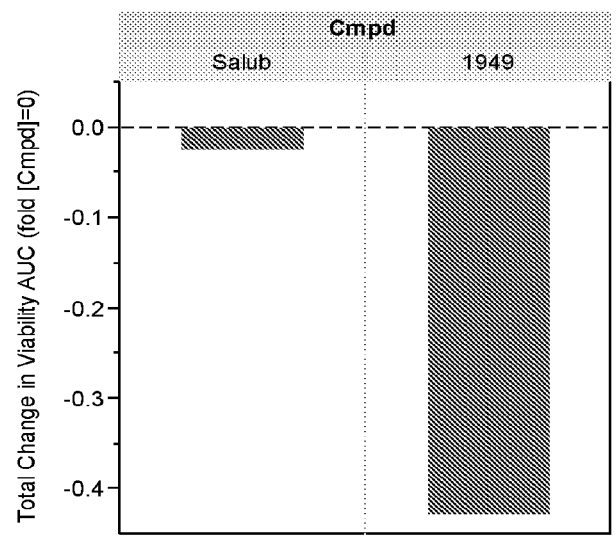
FIG. 13 is a drawing showing the total cell viability area change in the absence of tunicamycin for compound ID 1949 and salubrinal control Salub.

A description of the total cell viability area change in the absence of tunicamycin for compound ID 1949 and salubrinal control Salub is presented in FIG. 13.

Figure 14:
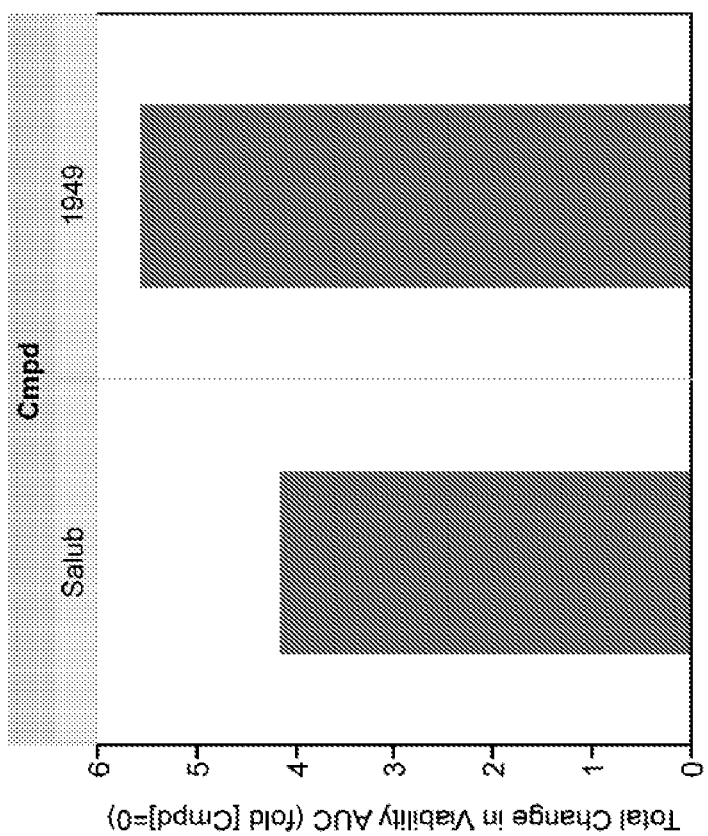
FIG. 14 is a drawing showing the dose-related change in cell viability area in the presence of tunicamycin for compound ID 1949 and salubrinal control Salub.

A description of the cell viability area in the presence of tunicamycin for compound ID 1949 and salubrinal control Salub is presented in FIG. 14.

Figure 15:
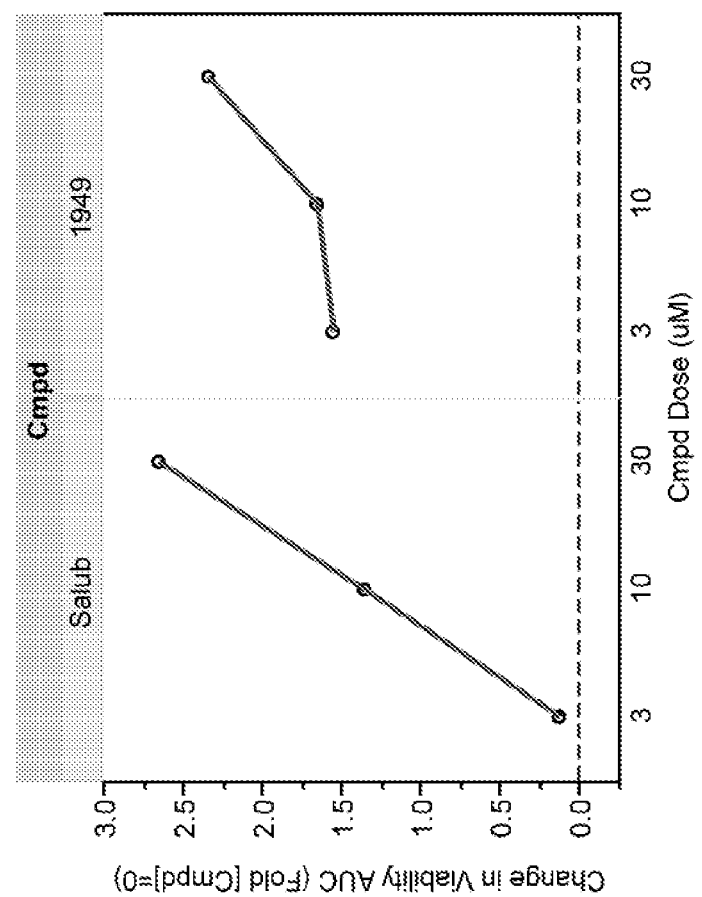
FIG. 15 is a drawing showing the total cell viability area change in the presence of tunicamycin for compound ID 1949 and salubrinal control Salub.

A description of the total cell viability area change in the presence of tunicamycin for compound ID 1949 and salubrinal control Salub is presented in FIG. 15.

Figure 16:
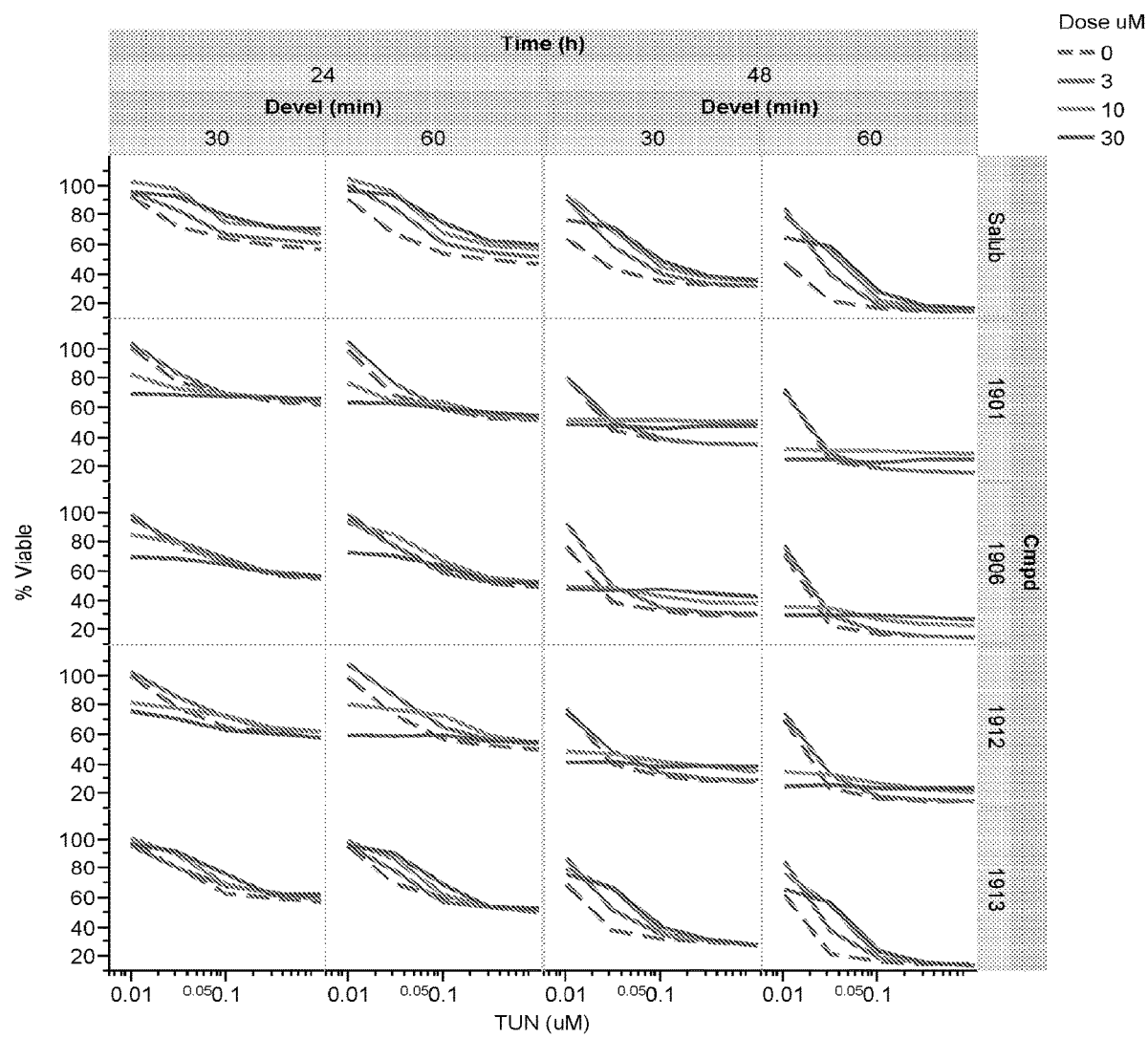
FIG. 16 is a drawing showing the cell viability at different concentrations of tunicamycin for compound IDs 1901, 1906, 1912, and 1913 and salubrinal Salub.

A description of the cell viability at different concentrations of tunicamycin for compound IDs 1901, 1906, 1912, and 1913 and salubrinal Salub is presented in FIG. 16. The dose of the compounds and control samples are varied between 0 µM and 30 µM. The results are reported after 24 hrs. and 48 hrs. of cell grow concentration and after 30 min and 60 min of WST-1 development.

Figure 17:
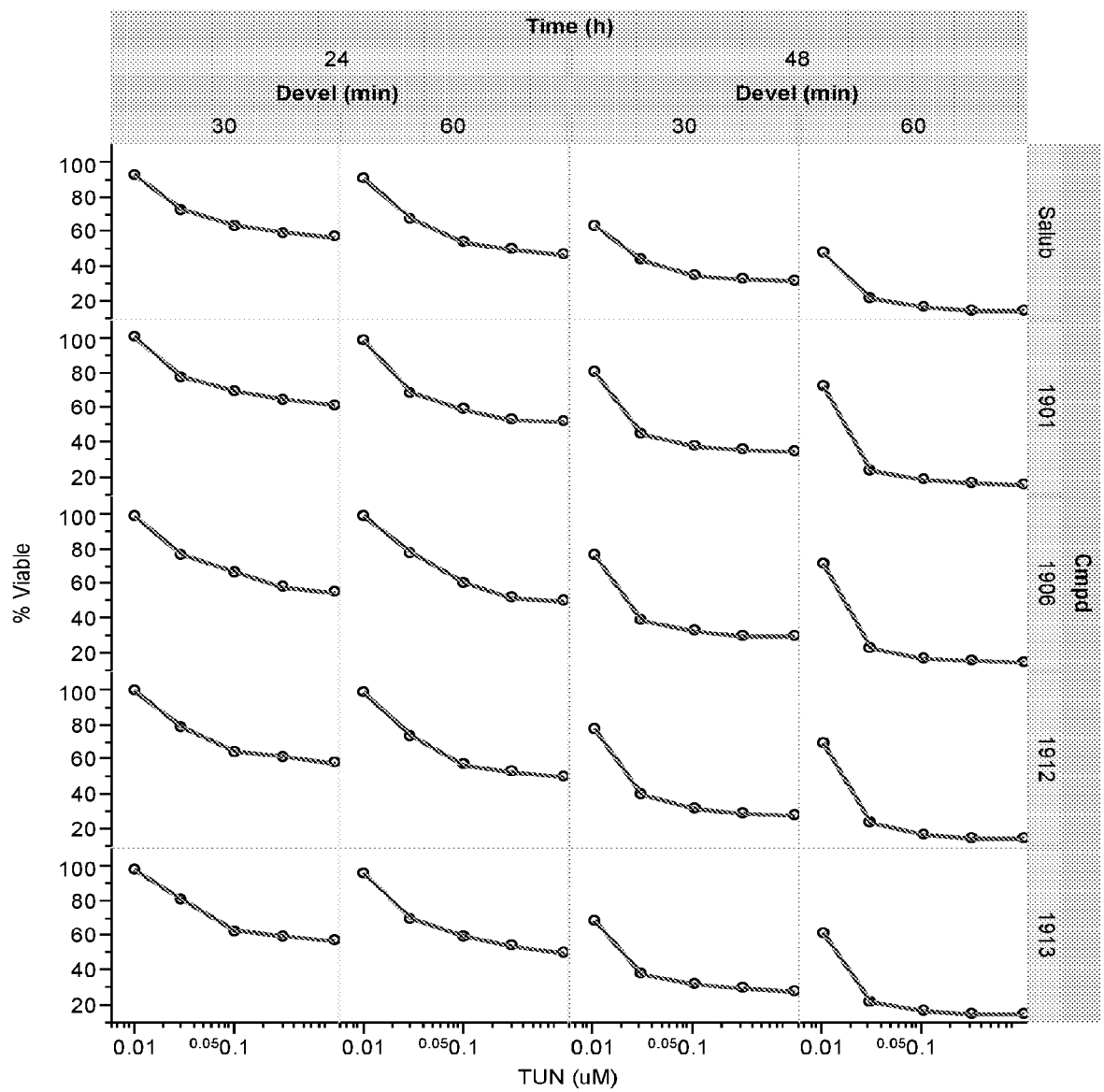
FIG. 17 is a drawing showing the cell viability at different concentrations of tunicamycin without compound or salubrinal.

A description of the cell viability at different concentrations of tunicamycin without compound or salubrinal is presented in FIG. 17. The results are reported after 24 hrs. and 48 hrs. of cell grow concentration and after 30 min and 60 min of WST-1 development.

Figure 18:
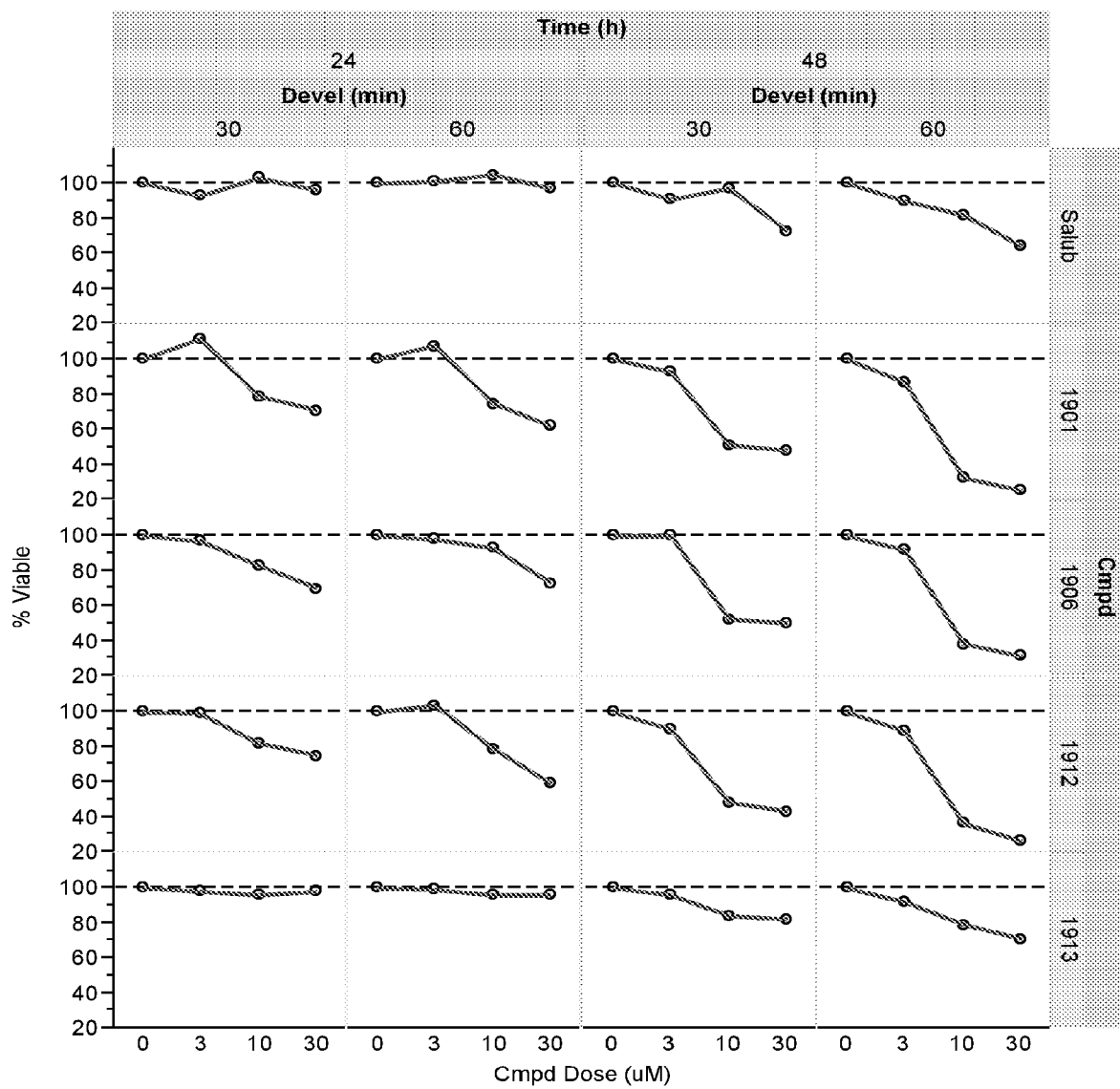
FIG. 18 is a drawing showing the cell viability in the absence of tunicamycin for compound IDs 1901, 1906, 1912, and 1913 and salubrinal Salub.

A description of the cell viability in the absence of tunicamycin for compound IDs 1901, 1906, 1912, and 1913 and salubrinal Salub is presented in FIG. 18. The results are reported after 24 hrs. and 48 hrs. of cell grow concentration and after 30 min and 60 min of WST-1 development.

Figure 19:
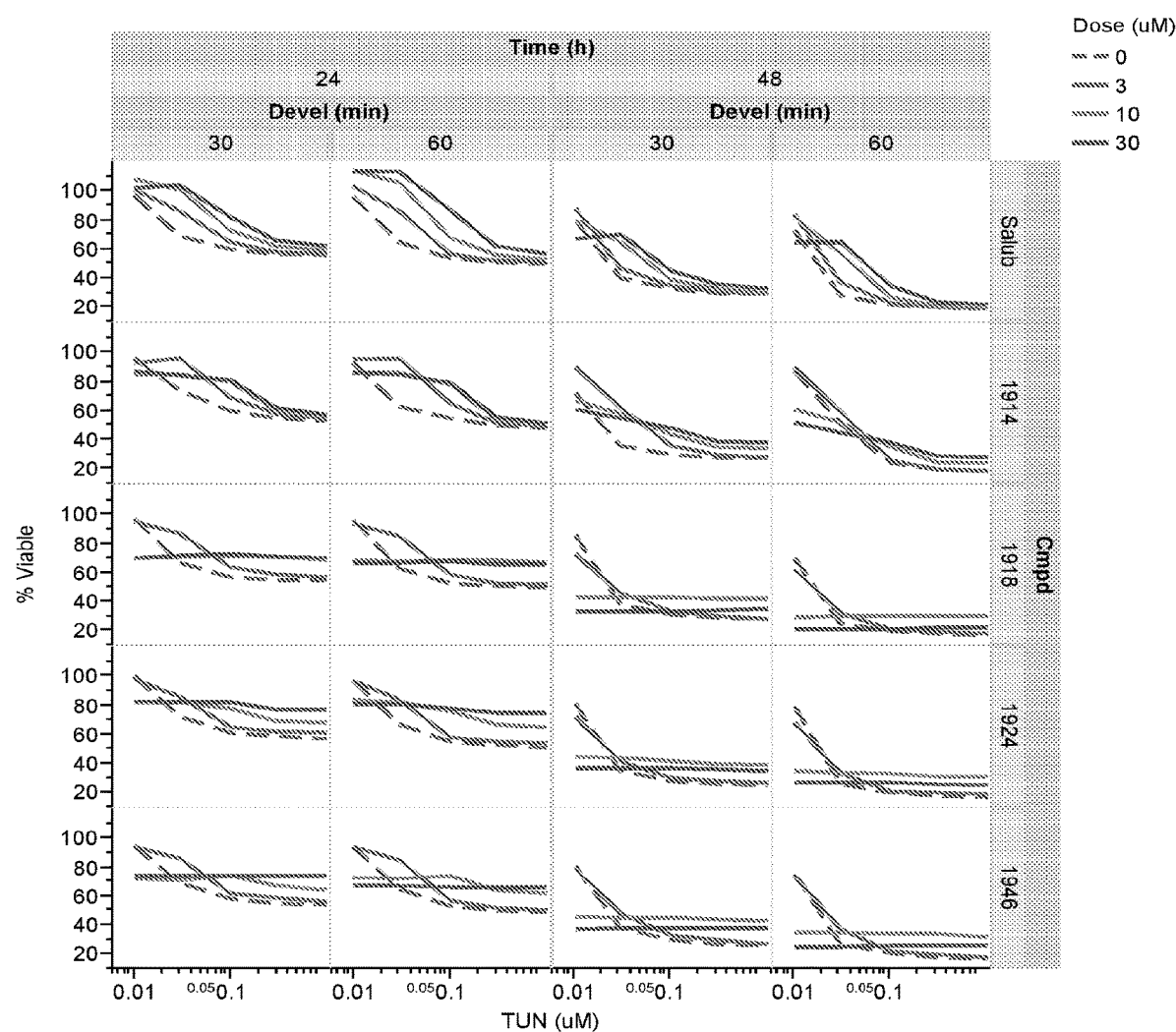
FIG. 19 is a drawing showing the cell viability at different concentrations of tunicamycin for compound IDs 1914, 1918, 1924, and 1946 and salubrinal Salub.

A description of the cell viability at different concentrations of tunicamycin for compound IDs 1914, 1918, 1924, and 1946 and salubrinal Salub is presented in FIG. 19. The dose of the compounds and control samples are varied between 0 µM and 30 µM. The results are reported after 24 hrs. and 48 hrs. of cell grow concentration and after 30 min and 60 min of WST-1 development.

Figure 20:
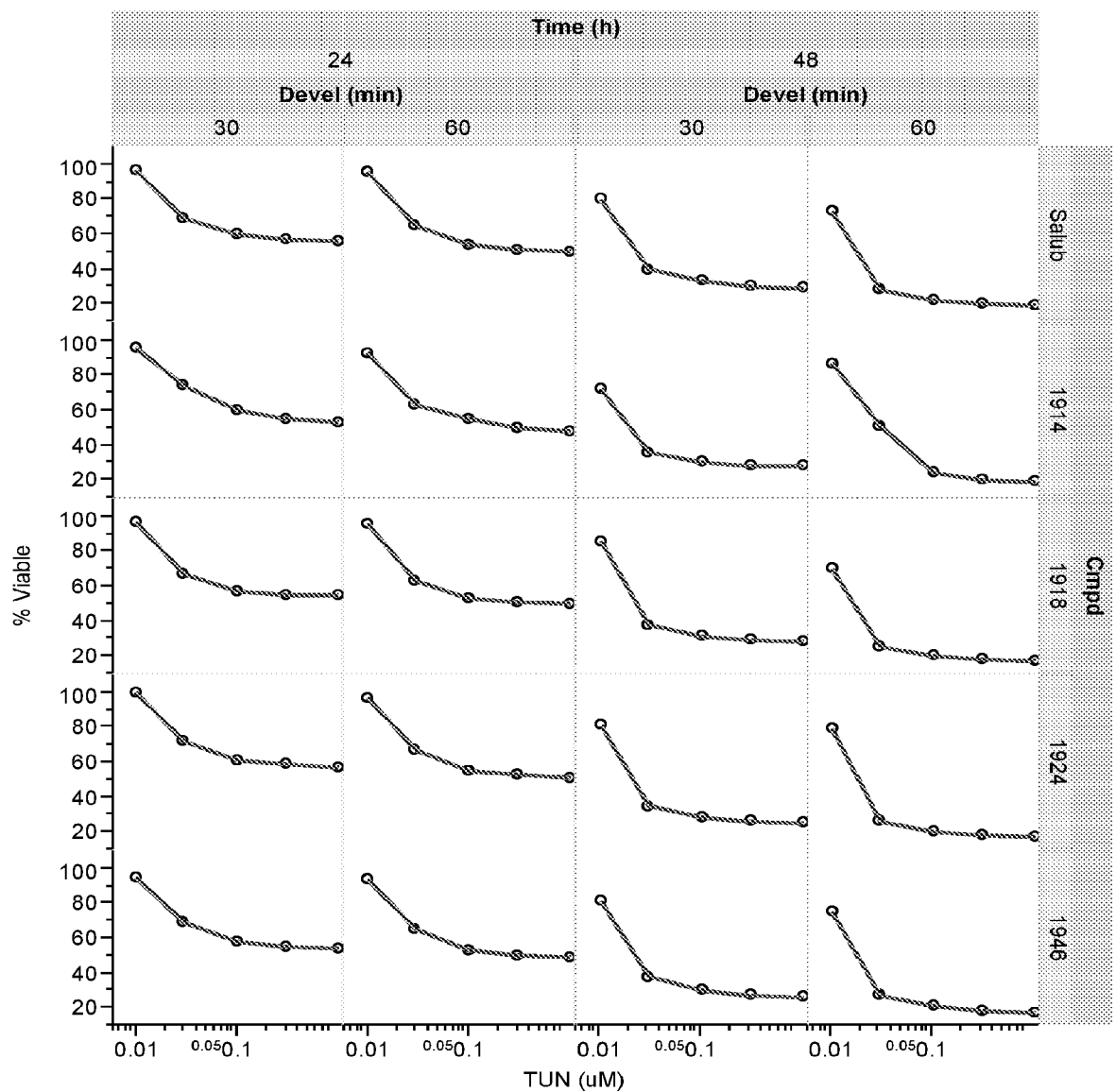
FIG. 20 is a drawing showing the cell viability at different concentrations of tunicamycin without compound or salubrinal.

A description of the cell viability at different concentrations of tunicamycin without compound or salubrinal is presented in FIG. 20. The results are reported after 24 hrs. and 48 hrs. of cell grow concentration and after 30 min and 60 min of WST-1 development.

Figure 21:
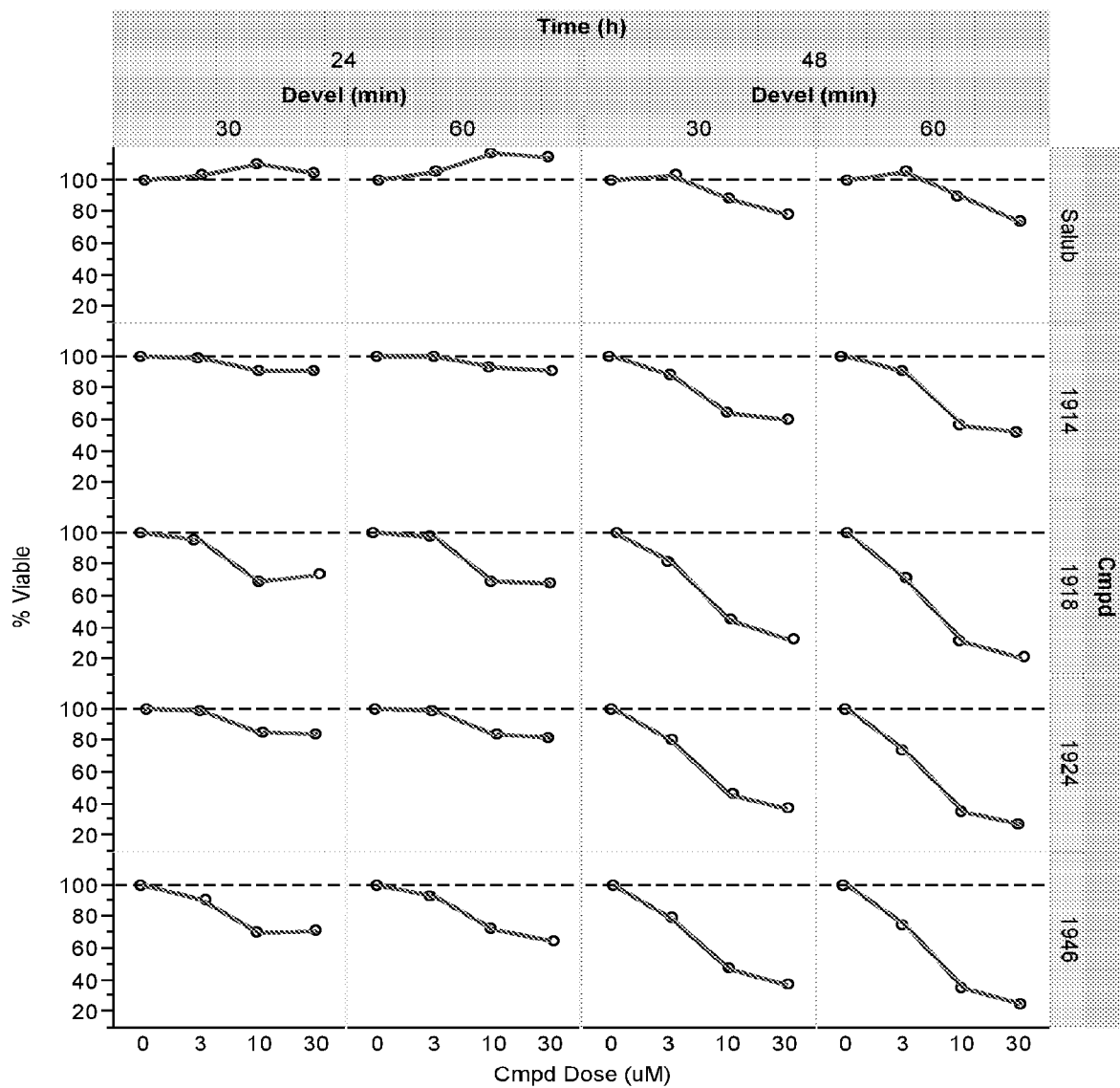
FIG. 21 is a drawing showing the cell viability in the absence of tunicamycin for compound IDs 1914, 1918, 1924, and 1946 and salubrinal Salub.

A description of the cell viability in the absence of tunicamycin for compound IDs 1914, 1918, 1924, and 1946 and salubrinal Salub is presented in FIG. 21. The results are reported after 24 hrs. and 48 hrs. of cell grow concentration and after 30 min and 60 min of WST-1 development.

Figure 22:
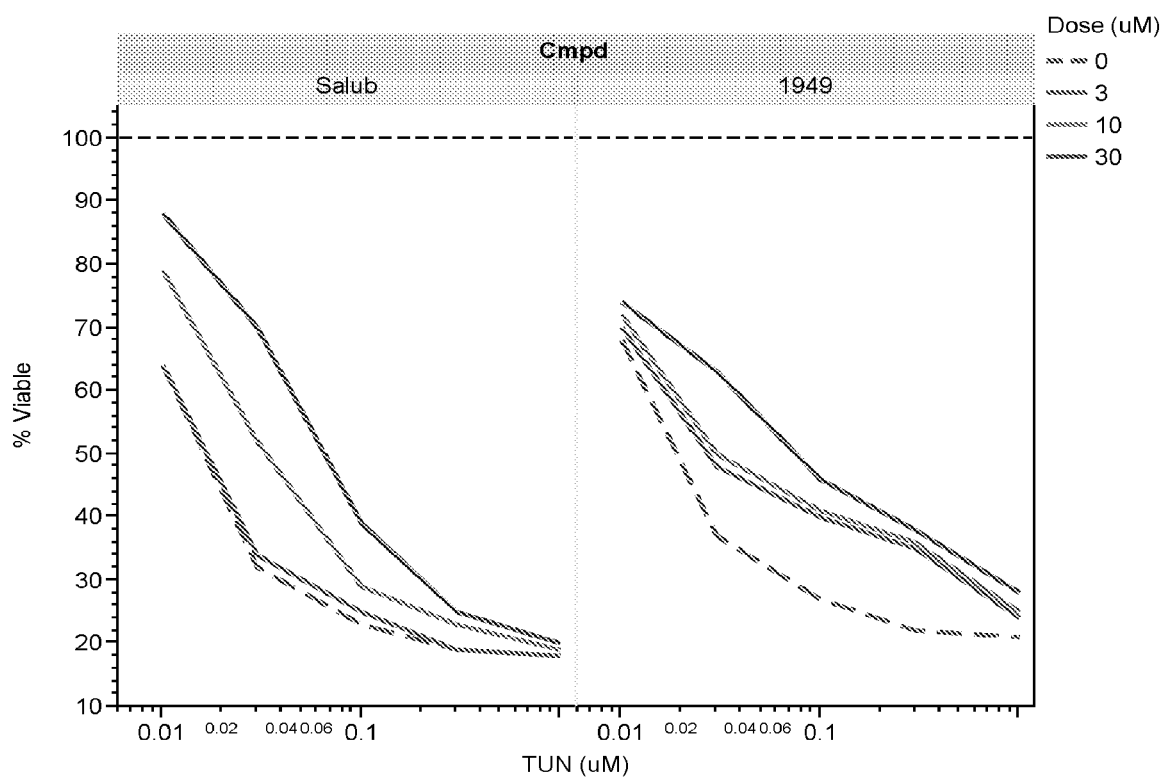
FIG. 22 is a drawing showing the cell viability at different concentrations of tunicamycin for compound ID 1949 and salubrinal.

A description of the cell viability at different concentrations of tunicamycin for compound ID 1949 and salubrinal Salub is presented in FIG. 22. The dose of the compound and control sample are varied between 0 µM and 30 µM.

Figure 23:
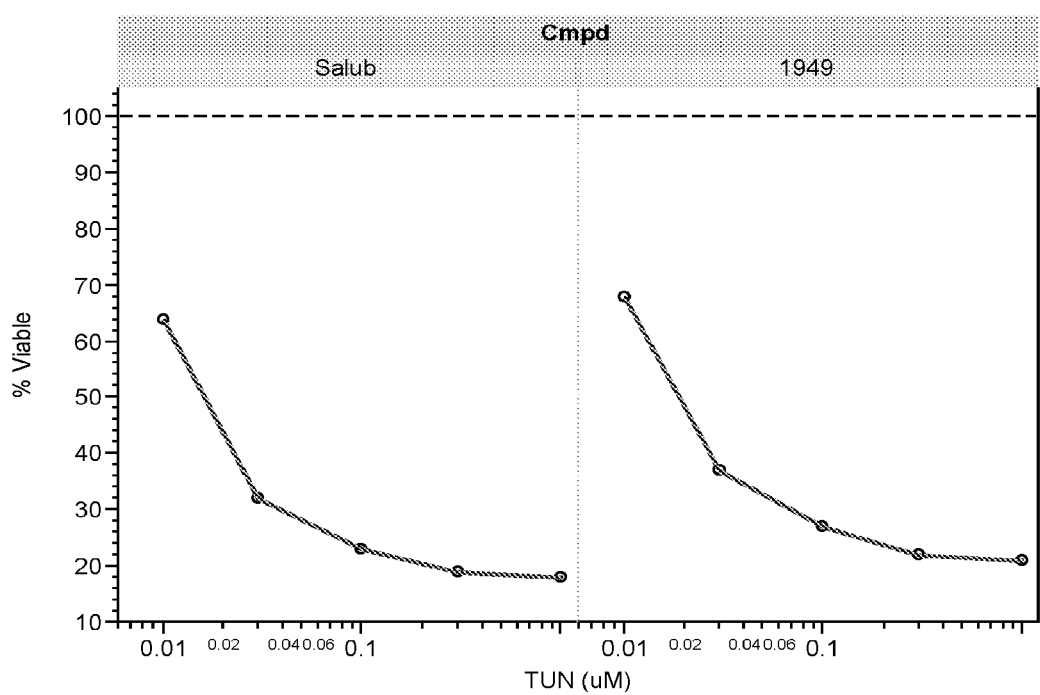
FIG. 23 is a drawing showing the cell viability at different concentrations of tunicamycin without compound or salubrinal.

A description of the cell viability at different concentrations of tunicamycin without compound or salubrinal is presented in FIG. 23.

Figure 24:
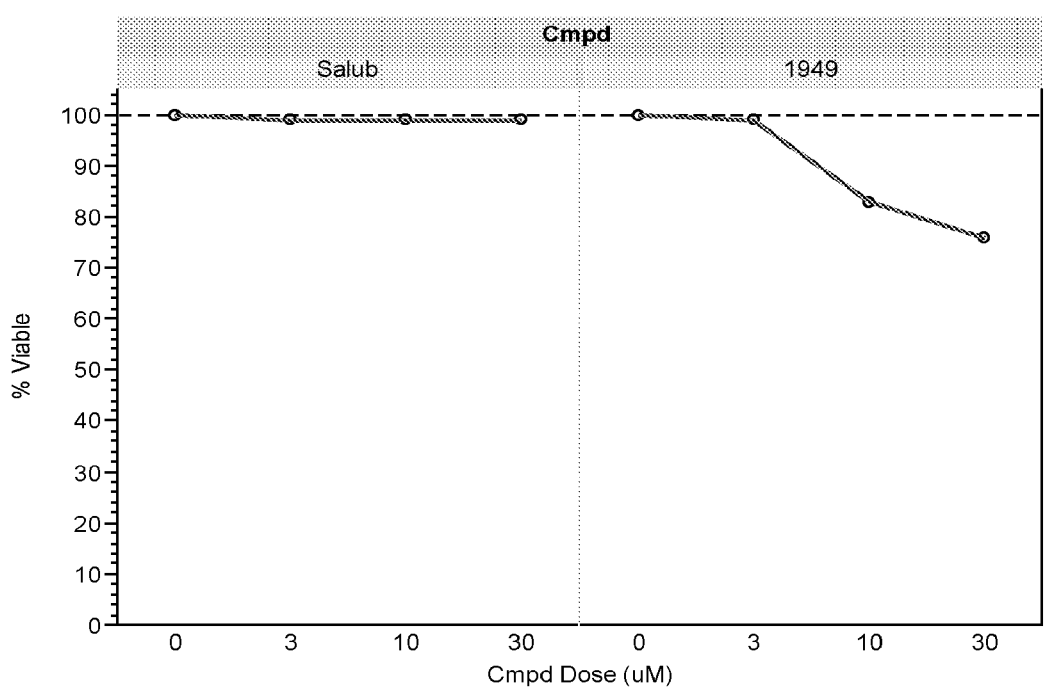
FIG. 24 is a drawing showing the cell viability in the absence of tunicamycin for compound ID 1949 and salubrinal.

A description of the cell viability in the absence of tunicamycin for compound ID 1949 and salubrinal is presented in FIG. 24.

A description of the properties of compound IDs 1901, 1903, 1905, 1906, 1912, 1913, 1914, 1918, 1924, and 1946 is presented in FIG. 25. The properties include the total increase in cell viability (AUC) in the presence of tunicamycin dose-response-induced proteostasis (ViaIncTot), the total change in cell viability (AUC) caused by compound alone in the absence of tunicamycin (CmpViaTot), the percent of parent compound lost when incubated in phosphate buffer (PlossBuff), the percent of parent compound converted to salubrinal when incubated in phosphate buffer (SgainBuff), the percent of parent compound lost when incubated in mouse plasma (PlossPlas), the percent of parent compound converted to salubrinal when incubated in mouse plasma (SgainPlas), the percent of parent compound lost when incubated in mouse liver microsomes without NADPH cofactor (Liver−), and the percent of parent compound lost when incubated in mouse liver microsomes with NADPH cofactor present (Liver+).

Pharmaceutical Compositions of Dephosphorylation Inhibitors

The dephosphorylation inhibitor may be administered as a pharmaceutically acceptable salt, hydrate, or solvate thereof. As used herein, a "pharmaceutically acceptable salt" or "salt" refers to a salt of one or more compounds. Suitable pharmaceutically acceptable salts of compounds include acid addition salts which may, for example, be formed by mixing a solution of the compound with a solution of a pharmaceutically acceptable acid, such as hydrochloric acid, hydrobromic acid, sulfuric acid, fumaric acid, maleic acid, succinic acid, benzoic acid, acetic acid, citric acid, tartaric acid, phosphoric acid, carbonic acid, or the like. Where the compounds carry one or more acidic moieties, pharmaceutically acceptable salts may be formed by treatment of a solution of the compound with a solution of a pharmaceutically acceptable base, such as lithium hydroxide, sodium hydroxide, potassium hydroxide, tetraalkylammonium hydroxide, lithium carbonate, sodium carbonate, potassium carbonate, ammonia, alkylamines, or the like. As used herein, a "hydrate" refers to a crystal form where a stoichiometric or non-stochiometric amount of water is bound by non-covalent intermolecular forces into the crystal structure. As used herein, a "solvate" refers to a crystal form where a stoichiometric or non-stoichiometric amount of solvent, or mixture of solvents, is incorporated into the crystal structure. Examples of solvents are water, acetone, ethanol, methanol, propanol, dichloromethane, etc.

In an exemplary embodiment, the compound can be administered in a pharmaceutically acceptable carrier. The phrase "pharmaceutically acceptable carrier" as used herein means a pharmaceutically-acceptable material, composition or vehicle, such as a liquid or solid filler, diluent, excipient, solvent or encapsulating material, involved in carrying or transporting a chemical agent. Pharmaceutically acceptable carriers include pharmaceutically acceptable salts, where the term "pharmaceutically acceptable salts" includes salts of the active compounds which are prepared with relatively nontoxic acids or bases, depending on the particular substituents found on the compounds described herein. Examples of pharmaceutically acceptable carriers are solvents, diluents, dispersion media, suspension aids, surface active agents, preservatives, solid binders, stabilizers, fillers, binding agents, lubricants, coatings, antibacterial and antifungal agents, isotonic and absorption delaying agents, and the like that are physiologically compatible. Various vehicles and carriers used in formulating pharmaceutical compositions and known techniques for the preparation thereof are disclosed in Remington's Pharmaceutical Sciences (A. Osol et al. eds., 15th ed. 1975). Pharmaceutically acceptable carriers may further comprise minor amounts of auxiliary substances such as wetting or emulsifying agents, preservatives or buffers, which enhance the shelf life or effectiveness of the pharmacological agent Such carriers enable the compounds to be formulated as tablets, pills, dragees, capsules, liquids, gels, syrups, slurries, suspensions and the like, for oral ingestion by a patient to be treated. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. In one embodiment, mannitol and magnesium stearate are used as pharmaceutically acceptable carriers.

The pharmaceutical compositions may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. In one embodiment, the mode of administration is oral delivery.

Various solid oral dosage forms can be used for administering compounds including such solid forms as tablets, gelcaps, capsules, caplets, granules, lozenges and bulk powders. The compounds can be administered alone or combined with various pharmaceutically acceptable carriers, diluents (such as sucrose, mannitol, lactose, starches) and excipients known in the art, including but not limited to suspending agents, solubilizers, buffering agents, binders, disintegrants, preservatives, colorants, flavorants, lubricants and the like. Time release capsules, tablets and gels are also advantageous in administering the compounds. In one embodiment, the dephosphorylation inhibitor is administered in a hard gelatin capsule.

Various liquid oral dosage forms can also be used for administering compounds, including aqueous and non-aqueous solutions, emulsions, suspensions, syrups, and elixirs. Such dosage forms can also contain suitable inert diluents known in the art such as water and suitable excipients known in the art such as preservatives, wetting agents, sweeteners, flavorants, as well as agents for emulsifying and/or suspending the compounds. The compounds may be injected, for example, intravenously, in the form of an isotonic sterile solution. Other preparations are also possible. Fingolimod hydrochloride is soluble in water (>10%) as well as 0.9% saline and aqueous buffers at or below pH 2.0. It is very slightly soluble or practically insoluble in aqueous buffers at or above pH 3.0. A variety of methods are known in the art to improve the solubility of the pharmacological agent in water and other aqueous solutions. For example, U.S. Pat. No. 6,008,192 to Al-Razzak et al. teaches a hydrophilic binary system comprising a hydrophilic phase and a surfactant, or mixture of surfactants, for improving the administration of lipophilic compounds such as the pharmacological agent.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., the pharmacological agent) in the required amount in an appropriate solvent with one or a combination of ingredients enumerated above, as required, followed by filtered sterilization.

Generally, dispersions are prepared by incorporating the active compound into a sterile vehicle that contains a basic dispersion medium and the required other ingredients from those enumerated above. In the case of sterile, lyophilized powders for the preparation of sterile injectable solutions, the method of preparation can include vacuum drying and/or spray-drying to yield a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts or gelatin.

The pharmaceutical compositions of the invention may include a "therapeutically effective amount" or a "prophylactically effective amount" of a pharmacological agent of the invention. A "therapeutically effective amount" refers to an amount effective, at dosages and for periods of time necessary, to achieve the desired therapeutic result. A therapeutically effective amount of the pharmacological agent may vary according to factors such as the disease state, age, sex, and weight of the individual, and the ability of the pharmacological agent to elicit a desired response in the individual. A therapeutically effective amount is also one in which any toxic or detrimental effects of the pharmacological agent are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of a pharmacological agent according to the invention is between 5 mg/day to about 2000 mg/day or about 50 mg/day to about 1000 mg/day, or in some instances about 100 mg/day to 500 mg/day. Preferably, administration of a therapeutically effective amount of pharmacological agent, results in a concentration of pharmacological agent in the bloodstream in the range of 1 nanomolar (nM) to 100 millimolar (mM) concentration. For example, a concentration range of about 10 nM to about 10 mM, about, 1 nM to about 1 mM, about 1 mM to about 100 micromolar (μM), about 1 μM to about 500 μM, about 1 μM to about 200 μM, preferably about 10 μM to about 50 μM. It is to be noted that the dose may be given in divided doses and dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

One skilled in the art will appreciate further features and advantages based on the above-described embodiments. Accordingly, the methods and compositions disclosed herein are not to be limited by what has been particularly shown and described, except as indicated by the appended claims. All references, patents, patent applications and other publications cited herein are expressly incorporated herein in their entirety.

While the applicant's teachings are described in conjunction with various embodiments, it is not intended that the applicant's teachings be limited to such embodiments. On the contrary, the applicant's teachings encompass various alternatives, modifications, and equivalents, as will be appreciated by those of skill in the art.

The invention claimed is:

1. A composition comprising a compound of Formula (II) having a structure as follows:

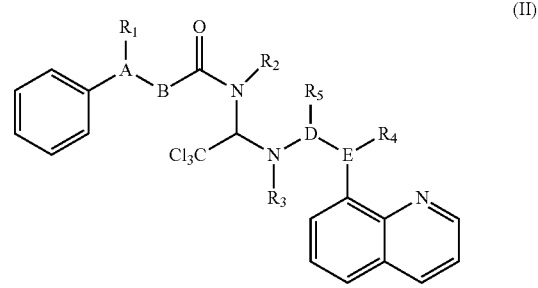

or an isomer, pharmaceutically acceptable salt or solvate thereof, wherein $R^1$ is H, $R^2$ is H, $R^3$ is H, $R^4$ is H or null, $R^5$ is —$SR^6$, $R^6$ is $CH_2$ ($C_{3-6}$ cycloheteroalkyl), $C_{3-6}$ cycloheteroalkyl, amino acid, amino acid derivative, $C_{1-20}$ alkyl, or $C_{1-20}$ heteroalkyl, A-B is C=CH, and D-E is CH—N or C=N and a pharmaceutically acceptable carrier.

2. The composition of claim 1 wherein the pharmaceutically acceptable carrier is selected from the group consisting of a lipid, lipid derivative, liposome, protein, albumin, synthetic polymer, natural polymer, synthetic oligomer, natural oligomer, cyclodextrin, cyclodextrin derivative, cellulose, and cellulose derivative.

3. The composition of claim 2, wherein the composition is formulated for oral administration.

4. The composition of claim 2, wherein the compound is formulated as a single daily dose.

5. The composition of claim 2, wherein the compound is formulated in a dosage between about 5 mg and about 2000 mg.

6. The composition of claim 1, wherein the compound is selected from the group consisting of:
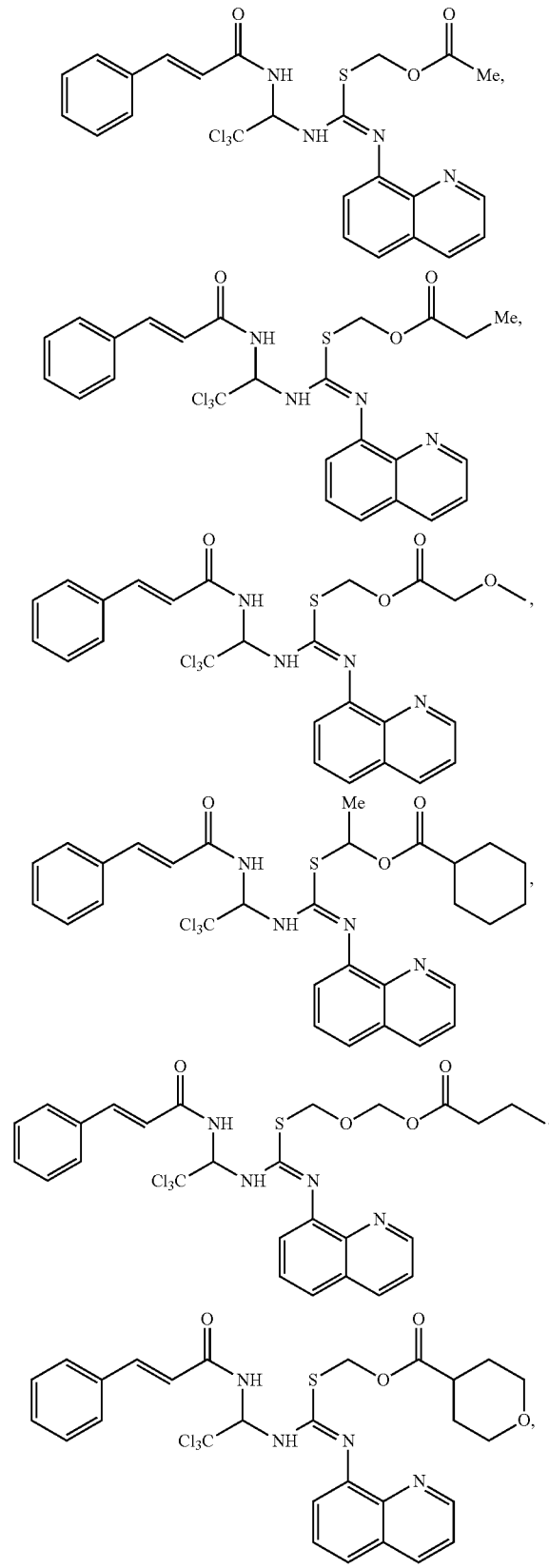
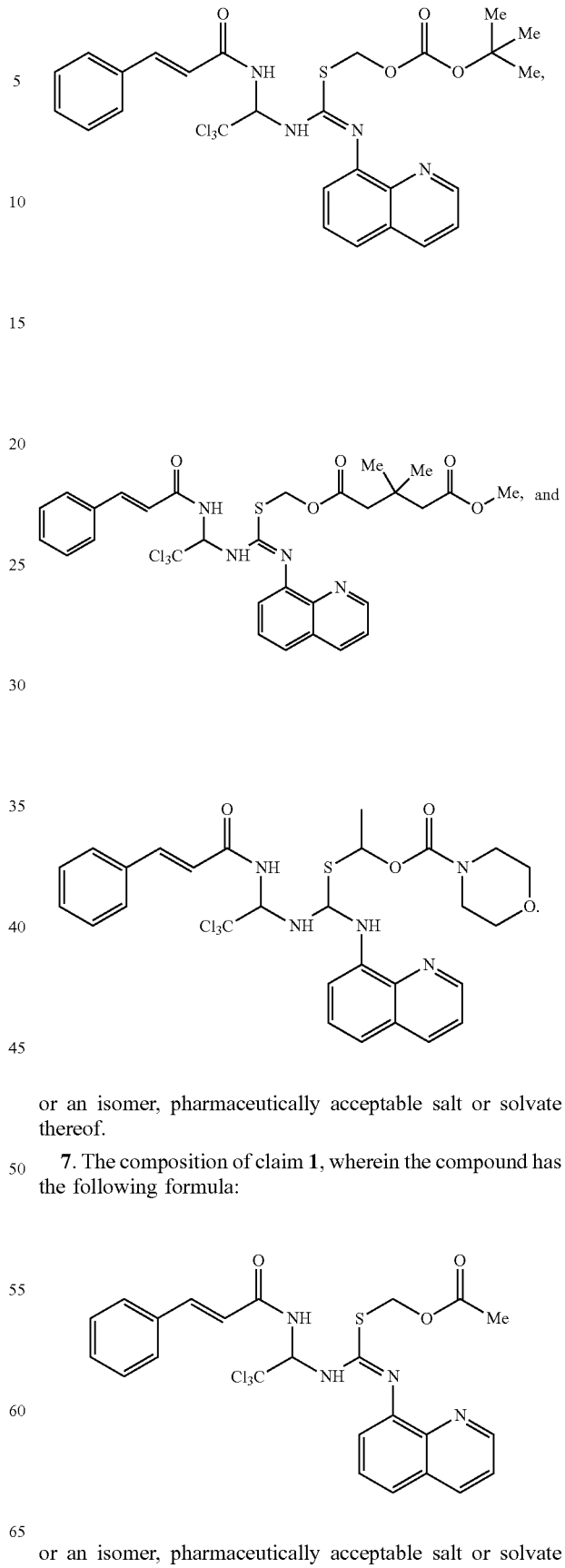
or an isomer, pharmaceutically acceptable salt or solvate thereof.
7. The composition of claim 1, wherein the compound has the following formula:
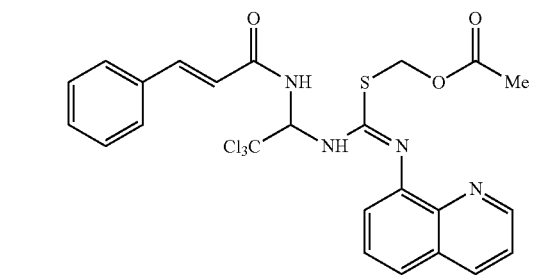
or an isomer, pharmaceutically acceptable salt or solvate thereof.

8. The composition of claim 1, wherein the compound has the following formula:

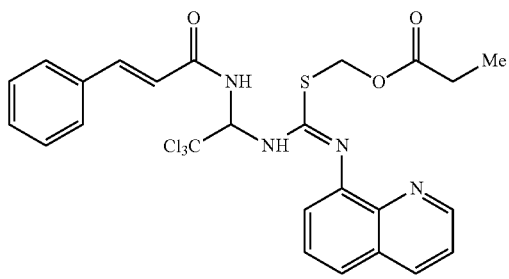

or an isomer, pharmaceutically acceptable salt and solvate thereof.

9. The composition of claim 1, wherein the compound has the following formula:

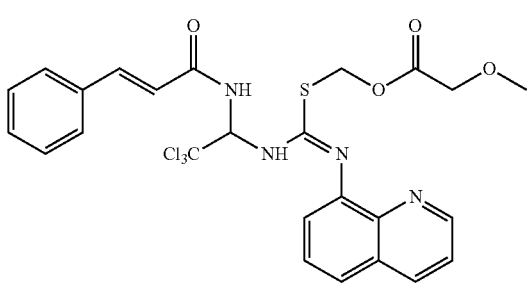

or an isomer, pharmaceutically acceptable salt or solvate thereof.

10. The composition of claim 1, wherein the compound has the following formula:

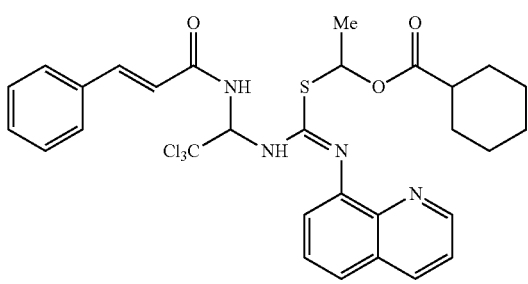

or an isomer, pharmaceutically acceptable salt or solvate thereof.

11. The composition of claim 1, wherein the compound has the following formula:

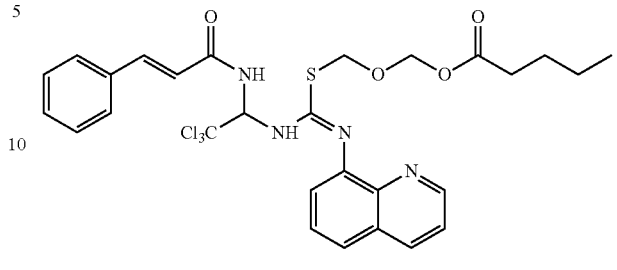

or an isomer, pharmaceutically acceptable salt or solvate thereof.

12. The composition of claim 1, wherein the compound has the following formula:

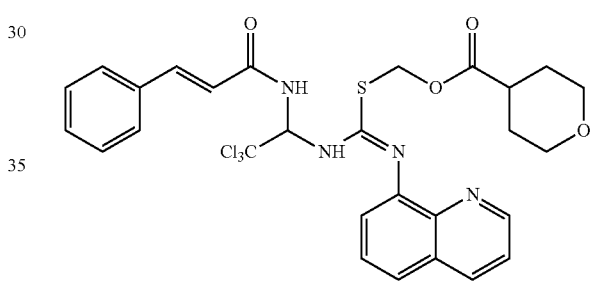

or an isomer, pharmaceutically acceptable salt or solvate thereof.

13. The composition of claim 1, wherein the compound has the following formula:

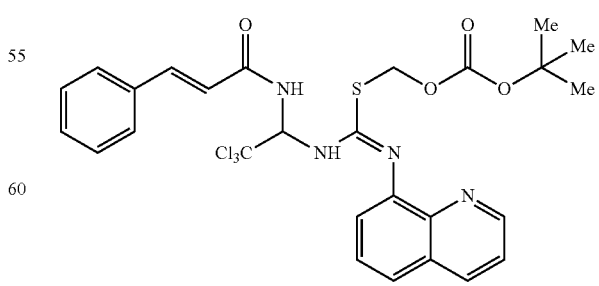

or an isomer, pharmaceutically acceptable salt or solvate thereof.

14. The composition of claim 1, wherein the compound has the following formula:
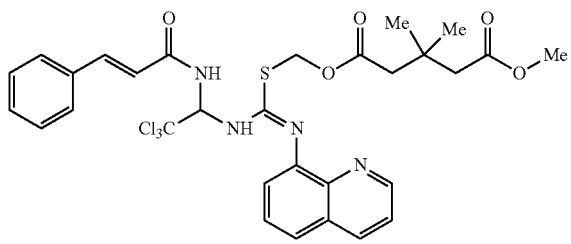
or an isomer, pharmaceutically acceptable salt or solvate thereof.
15. The composition of claim 1, wherein the compound has the following formula:
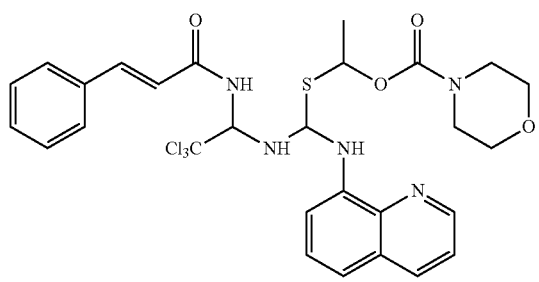
or an isomer, pharmaceutically acceptable salt or solvate thereof.
* * * * *